United States Patent
Jantos et al.

(10) Patent No.: US 9,200,005 B2
(45) Date of Patent: Dec. 1, 2015

(54) INHIBITOR COMPOUNDS OF PHOSPHODIESTERASE TYPE 10A

(71) Applicants: AbbVie Deutschland GmbH & Co. KG, Wiesbaden (DE); AbbVie Inc., North Chicago, IL (US)

(72) Inventors: Katja Jantos, Ludwigshafen (DE); Michael Ochse, Ludwigshafen (DE); Hervé Geneste, Ludwigshafen (DE); Jayne Froggett, Ludwigshafen (DE); Clarissa Jakob, North Chicago, IL (US); Karla Drescher, Ludwigshafen (DE); Jürgen Dinges, North Chicago, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 14/189,961

(22) Filed: Feb. 25, 2014

(65) Prior Publication Data

US 2014/0275069 A1    Sep. 18, 2014

Related U.S. Application Data

(60) Provisional application No. 61/779,141, filed on Mar. 13, 2013.

(51) Int. Cl.
*C07D 495/04* (2006.01)

(52) U.S. Cl.
CPC .................................... *C07D 495/04* (2013.01)

(58) Field of Classification Search
CPC .................................................. C07D 495/04
USPC ....................................... 514/234.2; 544/235
See application file for complete search history.

(56) References Cited

U.S. PATENT DOCUMENTS

| 7,064,126 B2 * | 6/2006 | Cooper et al. ................ 514/248 |
| 8,389,567 B2 * | 3/2013 | Velicelebi et al. ............ 514/447 |
| 2006/0052380 A1 * | 3/2006 | Cooper et al. ................ 514/248 |
| 2007/0155779 A1 | 7/2007 | Verhoest et al. |

FOREIGN PATENT DOCUMENTS

| WO | 99/29695 | 6/1999 |
| WO | 03/093499 | 11/2003 |
| WO | 2004/065393 | 8/2004 |
| WO | 2005/012485 | 2/2005 |
| WO | 2005/120514 | 12/2005 |
| WO | 2006/028957 | 3/2006 |
| WO | 2007/022280 | 2/2007 |
| WO | 2007/082546 | 7/2007 |
| WO | 2007/085954 | 8/2007 |
| WO | 2007/096743 | 8/2007 |
| WO | 2007/098169 | 8/2007 |
| WO | 2007/098214 | 8/2007 |
| WO | 2007/100880 | 9/2007 |
| WO | 2007/103370 | 9/2007 |
| WO | 2007/103554 | 9/2007 |
| WO | 2007/137819 | 12/2007 |
| WO | 2007/137820 | 12/2007 |
| WO | 2008/001182 | 1/2008 |
| WO | 2008/004117 | 1/2008 |
| WO | 2008/006372 | 1/2008 |
| WO | 2008/020302 | 2/2008 |
| WO | 2009/025823 | 2/2009 |
| WO | 2009/025839 | 2/2009 |
| WO | 2009/029214 | 3/2009 |
| WO | 2009/036766 | 3/2009 |
| WO | 2009/068246 | 6/2009 |

(Continued)

OTHER PUBLICATIONS

Vippagunta (2001).*
Banker et al. (1997).*
Wolff et al. (1997).*
Kehler, J., "Phosphodiesterase 10A inhibitors: a 2009-2012 patent update," Expert Opin. Therapeutic Patents (2013) 23(1):31-45.
Kehler, J. et al., "Patented PDE10A inhibitors: novel compounds since 2007," Expert Opinion on Therapeutic Patents, Informa Healthcare (2009) 19(12):1715-1725.
International Search Report and Written Opinion for Application No. PCT/EP2014/054810 dated Apr. 3, 2014 (12 pages).
Cantin, L-D. et al., "PDE-10A inhibitors as insulin secretagogues," Bioorg. Med. Chem. Lett. (2007) 17:2869-2873.

(Continued)

*Primary Examiner* — Paul V Ward
(74) *Attorney, Agent, or Firm* — Lisa V. Mueller; Michael Best & Friedrich LLP

(57) ABSTRACT

The present invention relates to compounds of the formula I, the N-oxides, tautomers, the prodrugs and the pharmaceutically acceptable salts thereof:

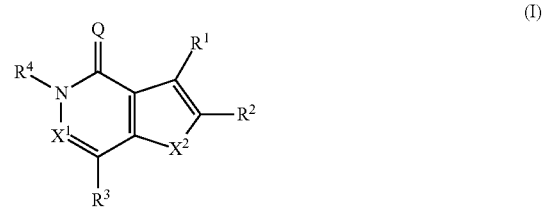

(I)

In formula I the variables X1 is CH or N, X2 is O or S and where R1, R2, R3, R4 and Q are as defined in the claims.
The compounds of the formula I, the N-oxides, tautomers, the prodrugs and the pharmaceutically acceptable salts thereof are inhibitors of phosphodiesterase type 10A. Thus, the invention also relates to the use of the compounds of the formula I, the N-oxides, tautomers, the prodrugs and the pharmaceutically acceptable salts thereof for the manufacture of a medicament and which thus are suitable for treating or controlling of medical disorders selected from neurological disorders and psychiatric disorders, for ameliorating the symptoms associated with such disorders and for reducing the risk of such disorders.

23 Claims, No Drawings

(56) References Cited

FOREIGN PATENT DOCUMENTS

| WO | 2009/068320 | 6/2009 |
| --- | --- | --- |
| WO | 2009/070583 | 6/2009 |
| WO | 2009/070584 | 6/2009 |
| WO | 2012/058133 | 5/2012 |
| WO | 2013/000994 | 1/2013 |
| WO | 2013/068470 | 5/2013 |

OTHER PUBLICATIONS

Chappie, T. et al., "PDE10A inhibitors: an assessment of the current CNS drug discovery landscape," Curr. Opin. in Drug Discovery & Development (2009) 12(4):438-467.

Diaz, G.J. et al., "The [3H]dofetilide binding assay is a predictive screening tool for hERG blockade and proarrhythmia: comparison of intact cell and membrane preparations and effects of altering [K+}o," J. Pharm. Toxicol. Meth. (2004) 50:187-199.

Francis, S.H. et al., "Mammalian cyclic nucleotide phosphodiesterases: molecular mechanisms and physiological functions," Physiol. Rev. (2011) 91:651-690.

Grauer, S.M. et al., "PDE10A inhibitor activity in preclinical models of the postive, cognitive and negative symptoms of schizophrenia," JPET Fast Forward (2006) 66 pages.

Nishi, A. et al., "Distinct roles of PDE4 and PDE10A in the regulation of cAMP/PKA signaling in the striatum," J. Neurosci. (2008) 28(42):10460-10471.

Rodefer, J.S. et al., "PDE10A inhibition reverses subchronic PCP-induced deficits in attentional set-shifting in rats," Eur. J. Neurosci. (2005) 21:1070-1076.

Schmidt, C.J. et al., "Preclinical characterization of selective phosphodiesterase 10A inhibitors: a new therapeutic approach to the treatment of schizophrenia," J. Pharm. Exp. Ther. (2008) 325(2):681-690.

Seeger, T.F. et al., "Immunohistochemical localization of PDE10A in the rat brain," Brain Res. (2003) 985:113-126.

Sotty, F. et al., "Phosphodiesterase 10A inhibition modulates the sensitivity of the mesolimbic dopaminergic system to D-amphetamine: involvement of the D1-regulated feedback control of midbrain dopamine neurons," J. Neurochem. (2009) 109:766-775.

\* cited by examiner

INHIBITOR COMPOUNDS OF PHOSPHODIESTERASE TYPE 10A

CROSS-REFERENCE TO RELATED APPLICATIONS

This claims priority to U.S. Patent Application No. 61/779,141, filed on Mar. 13, 2013, the contents of all of which are fully incorporated herein by reference.

The present invention relates to novel compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

BACKGROUND OF THE INVENTION

Phosphodiesterase type 10A (hereinafter PDE10A) is a dual-substrate phosphodiesterase that can convert both cAMP to AMP and cGMP to GMP. PDE10A is highly prominent in the mammalian brain. In the rat, as well as in other mammalian species, PDE10A and the mRNA of PDE10A are highly enriched in the GABAergic medium spiny projection neurons (MSNs) of the striatal complex (caudate nucleus, nucleus accumbens, and olfactory tubercle) where the output is regulated by the effect of PDE10A on cAMP and cGMP signalling cascades (see e.g. C. J. Schmidt et al, The Journal of Pharmacology and Experimental Therapeutics 325 (2008) 681-690, A. Nishi, The Journal of Neuroscience 2008, 28, 10450-10471).

MSNs express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. Brain Research, 2003, 985, 1 13-126) Inhibition of PDE10A results in striatal activation and behavioral suppression such as dampened locomotion, inhibition of conditioned avoidance response (CAR), and activity in the rat auditory gating model, suggesting that inhibitors of phosphodiesterase type 10A represent a novel class of antipsychotic agents.

The hypotheses around the physiological role of PDE10A and the therapeutic utility of PDE10A inhibitors derive in part from studies with papaverine (J. A. Siuciak et al. loc. cit.), the first extensively profiled pharmacological tool compound for this target. The PDE10A inhibitor papaverine was shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. (Rodefer et al., Eur. J. Neurosci., 4 (2005) 1070-1076).

The discovery of a new class of PDE10A inhibitors with improved potency, selectivity, and pharmacokinetic properties, provided an opportunity to further explore the physiology of PDE10A and the potential therapeutic utility of inhibiting this enzyme. The new class of inhibitors are exemplified by MP-10 (PF-2545920: 2-{-4-[1-methylpyridine-4-yl-1-H-pyrazol-3-3ly]phenoxymethyl}-quinoline) and TP-10, i.e. 2-{4-[pyridine-4-yl-1-(2,2,2-trifluoroethyl)-1-H-pyrazol-3-3ly]phenoxymethyl}-quinoline. The compounds offer a therapeutic approach to the treatment of schizophrenia (see C. J. Schmidt et al., loc cit.; S. M. Grauer et al., Journal of Pharmacology and Experimental Therapeutics, fast forward DOI 10.1124 JPET 109.155994). Positive signals in rodent models of schizophrenia include the: attenuation of conditioned avoidance response (CAR), inhibition of hyperactivity caused by amphetamine-induced dopamine release or phencyclidine (PCP) mediated NMDA receptor blockade, attenuation of pharmacologically impaired social or object recognition, and antagonism of apomorphine-induced climbing. Taken together, these data suggest a broad suppression of all 3 symptoms clusters (positive symptoms, negative symptoms & cognitive dysfunctions) linked to schizophrenia (see C. J. Schmidt et al., loc cit.; S. M. Grauer et al., loc. cit).

Beyond schizophrenia, selective PDE10 inhibitiors may have the potential for the treatment of Huntington's disease (S. H. Francis et al., Physiol. Rev., 91 (2011) 651-690) and they may be a therapeutic option for substance abuse disorders (F. Softy et al., J. Neurochem., 109 (2009) 766-775). Furthermore, it has been suggested that PDE10A inhibitors may be useful for treatment of obesity and non-insulin dependent diabetes (see e.g. WO 2005/120514, WO 2005/012485, Cantin et al, Bioorganic & Medicinal Chemistry Letters 17 (2007) 2869-2873).

In summary, inhibitors of PDE10A offer a promising therapeutic approach to the treatment or prevention of neurological and psychiatric disorders, in particular schizophrenia and related disorders, including symptoms linked to schizophrenia such as cognitive dysfunction.

Several classes of compounds which are inhibitors of PDE10A have been described in the art, the recent compound groups are:

Pyrido[3,2-e]pyridazines—see WO 2007/137819, WO 2007/137820, WO 2009/068246, WO 2009/068320, WO 2009/070583 and WO 2009/070584;

4-substituted phthalazines and quinazolines WO 2007/085954, WO 2007/022280, WO 2007/096743, WO 2007/103370, WO 2008/020302, WO 2008/006372 and WO 2009/036766;

4-substituted cinnazolines—see WO 2006/028957, WO 2007/098169, WO 2007/098214, WO 2007/103554, WO 2009/025823 and WO 2009/025839;

Isoquinolines and isoquinolinones—see WO 2007/100880 and WO 2009/029214

MP10 and MP10 like compounds: US 2007/0155779, WO 2008/001182 and WO 2008/004117; and Isoindolinones—see WO 2012/058133 and WO 2013/000994;

Pyrrolopyridin-5-ones—see WO 2013/000994;

Benzodiazepines—see WO 2007/082546.

For a further review see also T. Chappie et al. Current Opinion in Drug Discovery & Development 12(4), (2009) 458-467) and the literature cited therein as well as Jan Kehler, Phosphodiesterase 10A inhibitors: a 2009-2012 patent update, Expert Opin. Ther. Patents (2013) 23(1).

Although some of the compounds of prior art are known to inhibit PDE10A effectively having $IC_{50}$ values of less than 50 nM, there is still an ongoing need for compounds which inhibit PDE10A. In particular, there is an ongoing need for compounds which have one of the following characteristics:

i. Selective inhibition of PDE10A, in particular vis-à-vis inhibition of the other ten phosphodiesterase families PDE1-9, 11 and their different gene variants; suitable selectivity with regard to molecular receptors, transporters channels, enzymes or other biomolecules whose interaction with the PDE10A ligand might cause undesired side effects;

ii. metabolic stability, in particular microsomal stability, e.g. measured in vitro, in liver microsomes from various species (e.g. rat or human) in human cells, such as hepatocytes;

iii. no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

iv. a suitable solubility in water (in mg/ml);

v. suitable pharmacokinetics (time course of the concentration of the compound of the invention in plasma or in tissue, for example brain). The pharmacokinetics can be described by the following parameters: half-life, volume of distribution (in $l \cdot kg^{-1}$), plasma clearance (in $l \cdot h^{-1} \cdot kg^{-1}$), AUC (area under the curve, area under the concentration-time curve (in $1 \cdot ng \cdot h \cdot l^{-1}$), oral bioavailability, (the dose-normalized ratio of AUC after oral administration and AUC after intravenous administration), the so-called brain-plasma ratio (the ratio of AUC in brain tissue and AUC in plasma);

vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

vii. high free fraction in brain, i.e. the fraction of the compound bound to proteins should be low.

viii. low lipophilicity.

BRIEF DESCRIPTION OF THE INVENTION

The present invention is thus based on the object of providing compounds which inhibit PDE10A at low concentrations.

The compounds are further intended to display at least one of the properties i. to viii. mentioned above, in particular high selectivity with regard to inhibition of PDE10A, high selectivity vis-à-vis other phosphodiesterases such as, enhanced metabolic stability, in particular microsomal and/or cytosolic stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides, the prodrugs, the hydrates and the tautomers thereof and the pharmaceutically suitable salts thereof:

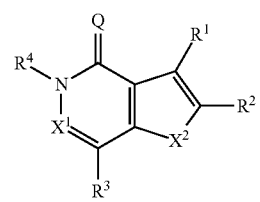

(I)

wherein
Q is O or S;
$X^1$ is N or CH;
$X^2$ is O or S;
$R^1$ is a moiety $Y^1$-$Cyc^1$;
$R^2$ is selected from the group consisting of hydrogen, halogen, OH, $C_1$-$C_4$-alkyl, trimethylsilyl, hydroxy-$C_1$-$C_4$-alkyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_2$-$C_4$-alkenyloxy, $C_1$-$C_4$-fluoroalkyl, $C_1$-$C_4$-fluoroalkoxy, $C_3$-$C_7$-cycloalkyl, optionally substituted by 1, 2 or 3 methyl groups, fluorinated $C_3$-$C_7$-cycloalkyl, $C_3$-$C_7$-cycloalkyloxy, CN and $NR^{x1}R^{x2}$;

$R^{x1}$ and $R^{x2}$, independently of each other are selected from the group consisting of hydrogen, $C_1$-$C_4$-alkyl, $C_1$-$C_4$-fluoroalkyl, $C_1$-$C_4$-alkoxy-$C_1$-$C_4$-alkyl, hydroxy-$C_1$-$C_4$-alkyl, and $C_3$-$C_6$-cycloalkyl;
$R^3$ is a moiety $Y^3$-$Cyc^3$;
$R^4$ is unsubstituted $C_1$-$C_4$-alkyl, $C_1$-$C_4$-fluoroalkyl, $C_3$-$C_6$-cycloalkyl, fluorinated $C_3$-$C_7$-cycloalkyl, or $C_1$-$C_4$-alkyl which carries one or two radicals $R^{44}$ $R^{44}$ is selected from the group consisting of $C_1$-$C_4$-alkoxy, $C_1$-$C_4$-fluoroalkoxy, CN, OH, $NR^{x3}R^{x4}$, $C_3$-$C_6$-cycloalkyl, $C_3$-$C_6$-cycloalkoxy, a 3- to 10-membered saturated, C-bound mono- or bicyclic heterocyclyl, 3- to 10-membered saturated, C-bound mono- or bicyclic heterocyclyloxy, where the last four groups of radicals are unsubstituted, partially or completely fluorinated and/or carry 1, 2, or 4 radicals selected from the group consisting of OH, $C_1$-$C_4$-alkyl, $C_1$-$C_4$-fluoroalkyl, $C_1$-$C_4$-alkoxy and $C_1$-$C_4$-fluoroalkoxy, and where C-bound heterocyclyl and C-bound heterocyclyloxy has 1, 2, 3 or 4 heteroatoms or heteroatom containing groups selected from the group consisting of O, N, S, SO and $SO_2$ as ring members;

where $R^{x3}$ and $R^{x4}$, independently of each other, are selected from the group consisting of hydrogen, $C_1$-$C_4$-alkyl, $C_1$-$C_4$-fluoroalkyl, $C_1$-$C_4$-alkoxy-$C_1$-$C_4$-alkyl, hydroxy-$C_1$-$C_4$-alkyl, and $C_3$-$C_6$-cycloalkyl, or $NR^{x3}R^{x4}$ is a saturated N-bound 3- to 7-membered, nitrogen heterocycle which may have 1, 2 or 3 further different or identical heteroatoms or heteroatom containing groups selected from the group consisting of O, N, S, SO and $SO_2$ as ring members and which may carry 1, 2, 3, 4, 5 or 6 substituents selected from the group consisting of halogen, OH, $C_1$-$C_4$-alkyl and $C_1$-$C_4$-alkoxy;

$Y^1$, $Y^3$ independently of each other are selected from the group consisting of a chemical bond, $CH_2$, O, O—$CH_2$, O—$CH(CH_3)$, O—$CH_2$—C(O)—NH, C(O)O, C(O), $NR^y$, $NR^y$—$CH_2$, $S(O)_2$—$NR^y$, C(O)—$NR^y$, S, S(O), $S(O)_2$, C(O)—O—$CH_2$, C(O)—$NR^y$—$CH_2$, 1,2-ethanediyl, 1,2-ethenediyl or 1,2-ethynediyl, where $R^y$ is selected from the group consisting of hydrogen, $C_1$-$C_4$-alkyl, $C_1$-$C_4$-alkylcarbonyl, $C_1$-$C_4$-alkylsulfonyl, $C_1$-$C_4$-fluoroalkylsulfonyl;

$Cyc^1$, $Cyc^3$ independently of each other are selected from the group consisting of phenyl, naphthyl, $C_3$-$C_8$-cycloalkyl, 3- to 8-membered saturated or partially unsaturated heteromonocyclic radicals, saturated or partially unsaturated 7- to 10 membered heterobicyclic radicals, 5- or 6-membered monocyclic hetaryl, and 8- to 10 membered bicyclic hetaryl, where the saturated or partially unsaturated heteromonocyclic and heterobicyclic radicals have 1, 2, 3 or 4 heteroatoms or heteroatom containing groups as ring members, which are selected from the group consisting of O, S, SO, $SO_2$ and N, and where the 5- or 6-membered monocyclic hetaryl and the 8- to 10-membered bicyclic hetaryl have 1, 2, 3 or 4 heteroatoms as ring members, which are selected from the group consisting of O, S and N, where $C_3$-$C_8$-cycloalkyl, the saturated or partially unsaturated heteromonocyclic and heterobicyclic radicals are unsubstituted or carry 1, 2, 3, 4 or 5 radicals $R^{C1}$ or one radical Y'—$R^{C2}$ and 0, 1, 2, 3 or 4 radicals $R^{C1}$;

where phenyl, naphthyl, the saturated or partially unsaturated heteromonocyclic and heterobicyclic radicals and the mono and bicyclic heteroaromatic radicals are unsubstituted or carry 1, 2, 3, 4 or 5 radicals $R^{C3}$ or one radical Y'—$R^{C2}$ and 0, 1, 2, 3 or 4 radicals $R^{C3}$;

where
$R^{C1}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^a$, Z—$C(O)OR^b$, Z—$C(O)NR^cR^d$, $NR^gSO_2R^h$, $S(O)_2NR^cR^d$ and Z—$NR^eR^f$, where
$R^a$, $R^h$ independently of each other are selected from the group consisting of hydrogen, $C_1$-$C_4$-alkyl and $C_1$-$C_4$-fluoroalkyl,
$R^b$, $R^g$ independently of each other are selected from the group consisting of hydrogen, $C_1$-$C_4$-alkyl, $C_2$-$C_4$-alkenyl and $C_1$-$C_4$-fluoroalkyl,
$R^c$, $R^d$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, $R^e$, $R^f$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy,
Z is a covalent bond or $C_1$-$C_4$-alkanediyl,
or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from the group consisting of O, S and N;
or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are selected from the group consisting of O, S and N,
or two radicals $R^{C1}$ which are bound at the same carbon atom may form an oxygen atom,
where the fused and the spiro radicals are unsubstituted or carry 1, 2, 3 or 4 radicals $R^{C4}$;

Y' is a chemical bond, $CH_2$, O, O—$CH_2$, C(O), $S(O)_2$, $NR^{y'}$, $NR^{y'}$—$CH_2$ or $NR^{y'}$—$S(O)_2$, where $R^{y'}$ is selected from the group consisting of hydrogen, $C_1$-$C_4$-alkyl, $C_1$-$C_4$-alkylcarbonyl, $C_1$-$C_4$-alkylsulfonyl, and $C_1$-$C_4$-fluoroalkylsulfonyl;

$R^{C2}$ is a carbocyclic or heterocyclic radical selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from the group consisting of O, S and N, and 5- or 6-membered heteroaromatic radicals, having 1, 2 or 3 heteroatoms as ring members, which are selected from the group consisting of O, S and N, where the carbocyclic and the heterocyclic radicals are unsubstituted or carry 1, 2, 3, 4 or 5 radicals $R^{C4}$;

$R^{C3}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^a$, Z—$C(O)OR^b$, Z—$C(O)NR^cR^d$, $NR^gSO_2R^h$, $S(O)_2NR^cR^d$ and Z≠$NR^eR^f$, wherein $R^a$, $R^b$, $R^c$, $R^d$, $R^e$, $R^f$, $R^g$ and $R^h$ have the same meaning as defined above,
or two radicals $R^{C3}$ which are bound at adjacent carbon atoms may form a saturated or partially unsaturated fused 5- or 6-membered carbocyclic radical or a saturated or partially unsaturated fused 5- or 6-membered heterocyclic radical having 1, 2 or 3 heteroatoms as ring members, which are selected from the group consisting of O, S and N, where the carbocyclic and the heterocyclic radical are unsubstituted or carry 1, 2, 3, 4 or 5 radicals $R^{C4}$;

$R^{C4}$ is selected from the group consisting of hydrogen, halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, $C(O)R^a$, benzyl, Z—$C(O)OR^b$, Z—$C(O)NR^cR^d$, $S(O)_2NR^cR^d$ and Z—$NR^eR^f$, where, Z, $R^a$, $R^b$, $R^c$, $R^d$, $R^e$ and $R^f$ are as defined above or two radicals $R^{C4}$ which are bound at the same atom may form an oxygen atom.

The present invention therefore relates to the compounds of the general formula I, their tautomers, the hydrates thereof, the pharmaceutically suitable salts of the compounds of formula I, the prodrugs of the compounds of formula I and the pharmaceutically suitable salts of said prodrugs, tautomers or hydrates of the compounds of formula I.

The compounds of the formula I, their salts, their prodrugs, their hydrates and their tautomers effectively inhibit PDE10A even at low concentrations. They are additionally distinguished by a high selectivity in relation to the inhibition of the PDE10A vis-à-vis inhibition of other phosphodiesterease, such as PDE3 or PDE4. The compounds of the invention may additionally have one or more of the properties ii. to viii. mentioned above.

The compounds of the formula I, their salts, their prodrugs, their hydrates and their tautomers are therefore particularly suitable for treating disorders and conditions in creatures, especially human creatures, which can be treated or controlled by inhibition of phosphodiesterase type 10A.

The invention therefore also relates to the use of carboxamide compounds of the formula I, their tautomers, their hydrates and their pharmaceutically suitable salts for the manufacture of a medicament, in particular of a medicament which is suitable for the treatment of a disorder or a condition which can be treated by inhibition of phosphodiesterase type 10A.

The invention further relates to a medicament, in particular a medicament which is suitable for the treatment of a disorder or a condition which can be treated by inhibition of phosphodiesterase type 10A. The medicament comprises at least one compound of the formula I, as described herein, or a tautomer, or a hydrate or a prodrug of said compound I, or a pharmaceutically suitable salt of the compound of the formula I or a pharmaceutically suitable salt of the tautomer, the hydrate or the prodrug of compound of the formula I.

DETAILED DESCRIPTION OF THE INVENTION

The terms "compound of the formula I" and "compounds I" are used as synonyms.

The term "prodrugs" means compounds which are metabolized in vivo to the compounds I of the invention. Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH or $NH_2$-group, where the OH or $NH_2$-group forms an ester/amide/peptide linkage, i.e. where one of the hydrogen atoms of the OH or $NH_2$-group is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an acyl group derived from an amino acid, e.g. glycine, alanine, serine, phenylalanine and the like, which is linked to the oxygen or nitrogen of the OH or $NH_2$-group via the carbonyl group of the amino acid. Further suitable prodrugs are alkylcarbonyloxyalkyl carbonates or carbamates of compounds I carrying an OH- or $NH_2$-group in which one of the hydrogen atoms of the OH- or $NH_2$-group has been replaced by a group of the formula —C(=O)—O—$CHR^p$—O—C(=O)—$R^q$ in which $R^p$ and $R^q$ are independently of one another $C_1$-$C_4$-alkyl. Such carbonates and carbamates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I or its prodrug or N-oxide is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylamino-ethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of formula I or its prodrug or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). It is preferred to employ the compounds enantiomerically pure or diastereomerically pure.

The present invention moreover relates to compounds as defined herein, wherein one or more of the atoms depicted in formula I have been replaced by its stable, preferably non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "alkenyl", "alkoxy", "alkenyloxy", "fluoroalkyl", "fluoroalkoxy", "cycloalkyl", "fluorinated cycloalkyl", "alkylene", "alkanediyl", "hetaryl" and radicals derived therefrom, such as "alkylcarbonyl", "alkylsulfanyl", "alkylsulfonyl", "fluoroalkylsulfonyl", "hydroxylalkyl", "cyanoalkyl", "alkoxylalkyl", "alkoxyalkoxy", "alkylsulfanylalkyl", "alkylsulfanylalkoxy" and "hetarylmethyl" represent groups of individual radicals. The groups of noncyclic radicals "alkyl", "alkenyl", "alkoxy", "alkenyloxy", "fluoroalkyl", "fluoroalkoxy", "alkylene", "alkanediyl", and the groups of radicals derived therefrom always include both unbranched and branched "alkyl", "alkenyl", "alkoxy", "alkenyloxy", "fluoroalkyl", "fluoroalkoxy", "alkylene" and "alkanediyl", respectively.

The prefix $C_n$-$C_m$-indicates the respective number of carbons in the hydrocarbon unit. Unless indicated otherwise, fluorinated substituents preferably have one to five identical or different fluorine atoms.

The term "halogen" designates in each case, fluorine, bromine, chlorine or iodine, specifically fluorine, chlorine or bromine Examples of other meanings are:

Alkyl, and the alkyl moieties for example in alkylcarbonyl, alkylsulfanyl, alkylsulfonyl, alkylsulfanylalkyl and alkylsulfaylalkoxy: saturated, straight-chain or branched hydrocarbon radicals having one or more C atoms, e.g. 1 to 4 carbon atoms, e.g. $C_1$-$C_4$-alkyl such as methyl, ethyl, propyl, 1-methylethyl, n-butyl, 1-methylpropyl, 2-methylpropyl and 1,1-dimethylethyl.

Fluoroalkyl and the fluoroalkyl moieties for example in fluoroalkylsulfonyl: an alkyl radical having ordinarily 1 to 4 C atoms, in particular 1 or 2 C-atoms ($C_1$-$C_2$-fluoroalkyl) as mentioned above, whose hydrogen atoms are partly or completely replaced by fluorine atoms such as fluoromethyl, difluoromethyl, trifluoromethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2-trifluoro-1-methylethyl, 2-fluoropropyl, 3-fluoropropyl, 2,2-difluoropropyl, 2,3-difluoropropyl, 3,3,3-trifluoropropyl, 2,3,3,3-pentafluoropropyl, heptafluoropropyl, 1-(fluoromethyl)-2-fluoroethyl, 4-fluorobutyl, and nonafluorobutyl.

Cycloalkyl, and the cycloalkyl moieties for example in cycloalkoxy or cycloalkyl-$C_1$-$C_4$-alkyl: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl, cycloheptyl and cyclooctyl.

Fluorinated cycloalkyl: monocyclic, saturated hydrocarbon groups having three or more C atoms, e.g. 3, 4, 5, 6 or 7 carbon ring members, such as cyclopropyl, cyclobutyl, cyclopentyl, cyclohexyl and cycloheptyl, wherein at least one, e.g. 1, 2, 3, 4, 5 or 6 of the hydrogen atoms are replaced by fluorine atoms, examples including 1-fluorocyclopropyl, 2-fluorocyclopropyl, 2,2-difluorocyclopropyl, 1,2-difluorocyclopropyl, 2,3-difluorocyclopropyl, etc.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl or cyclohexylmethyl.

Alkenyl, and alkenyl moieties for example in alkenyloxy: monounsaturated, straight-chain or branched hydrocarbon radicals having two or more C atoms, e.g. 2 to 6, 2 to 4 carbon atoms and one C=C-double bond in any position, e.g. $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl.

Alkoxy or alkoxy moieties for example in alkoxyalkyl and alkoxyalkoxy:

an alkyl radical as defined above having preferably 1 to 4 C atoms, which is connected to the remainder of the molecule via an O atom: e.g. methoxy, ethoxy, n-propoxy, 1-methylethoxy, butoxy, 1-methylpropoxy, 2-methylpropoxy or 1,1-dimethylethoxy.

Fluoroalkoxy: alkoxy as described above, in which the hydrogen atoms of these groups are partly or completely replaced by fluorine atoms, i.e. for example $C_1$-$C_4$-fluoroalkoxy, in particular $C_1$-$C_2$-fluoroalkoxy, such as fluoromethoxy, difluoromethoxy, trifluoromethoxy, 2-fluoroethoxy, 2,2-difluoroethoxy, 2,2,2-trifluoroethoxy, pentafluoroethoxy, 2-fluoropropoxy, 3-fluoropropoxy, 2,2-difluoropropoxy, 2,3-difluoropropoxy, 3,3,3-trifluoropropoxy, 2,2,3,3,3-pentafluoropropoxy, heptafluoropropoxy, 1-(fluoromethyl)-2-fluoroethoxy, specifically fluoromethoxy, difluoromethoxy, trifluoromethoxy, 2-fluoroethoxy, or 2,2,2-trifluoroethoxy.

Hydroxyalkyl: an alkyl radical ordinarily having 1 to 4 C atoms, in which one hydrogen atom is replaced by an OH radical. Examples thereof are $CH_2$—OH, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyetyl, 1-methyl-1-hydroxypropyl etc.

Cyanoalkyl: an alkyl radical ordinarily having 1 to 4 C atoms, in which one hydrogen atom is replaced by a CN radical. Examples thereof are $CH_2$—CN, 1-cyanoethyl, 2-cyanoethyl, 1-cyanopropyl, 2-cyanopropyl, 1-methyl-1-cyanoethyl, 1-methyl-2-cyanoethyl, 3-cyanopropyl, 2-cyanobutyl, 3-cyanobutyl, 4-cyanobutyl, 1-methyl-2-cyanopropyl, 1,1-dimethyl-2-cyanoetyl, 1-methyl-1-cyanopropyl etc.

Alkoxyalkyl: an alkyl radical ordinarily having 1 to 4 C atoms, in which one hydrogen atom is replaced by an alkoxy radical ordinarily having 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkoxyalkoxy: an alkoxyalkyl radical as defined above ordinarily having 1 to 4 C atoms both in the alkoxy and the alkyl moiety which is connected to the remainder of the molecule via an O atom: Examples thereof are OCH$_2$—OCH$_3$, OCH$_2$—OC$_2$H$_5$, n-propoxymethoxy, OCH$_2$—OCH(CH$_3$)$_2$, n-butoxymethoxy, (1-methylpropoxy)methoxy, (2-methylpropoxy)methoxy, OCH$_2$—OC(CH$_3$)$_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, etc.

Alkylcarbonyl: alkyl as defined above preferably having 1 to 4 C atoms, which is connected via a carbonyl group to the remainder of the molecule, e.g. acetyl, propionyl, butyryl, isobutyryl, pentanoyl, pivaloyl and the like.

Alkylsulfanyl and the alkylsulfanyl radicals in alkylsulfanylalkyl and alkylsulfanylalkoxy: alkyl as defined above preferably having 1 to 4 C atoms, which is connected via an S atom to the remainder of the molecule, e.g. methylsulfanyl, ethylsulfanyl, n-propylsulfanyl and the like.

Alkylsulfonyl: alkyl as defined above preferably having 1 to 4 C atoms, which is connected via an SO$_2$ group to the remainder of the molecule, e.g. methylsulfonyl, ethylsulfonyl, n-propylsulfonyl and the like.

Fluoroalkylsulfanyl: fluoroalkyl as defined above preferably having 1 to 4 C atoms, which is connected via an S atom to the remainder of the molecule, e.g. fluoromethylsulfanyl, difluoromethylsulfanyl, trifluoromethylsulfanyl, 2-fluoroethylsulfanyl, 2,2-difluoroethylsulfanyl, 2,2,2-trifluoroethylsulfanyl, pentafluoroethylsulfanyl, 2-fluoropropylsulfanyl, 3-fluoropropylsulfanyl, 2,2-difluoropropylsulfanyl, 2,3-difluoropropylsulfanyl, and heptafluoropropylsulfanyl.

Fluoroalkylsulfonyl: fluoroalkyl as defined above preferably having 1 to 4 C atoms, which is connected via an SO$_2$ group to the remainder of the molecule, e.g. fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl, pentafluoroethylsulfonyl, 2-fluoropropylsulfonyl, 3-fluoropropylsulfonyl, 2,2-difluoropropylsulfonyl, 2,3-difluoropropylsulfonyl, and heptafluoropropylsulfonyl.

Alkylsulfanylalkyl: an alkyl radical ordinarily having 1 to 4 C atoms, in which one hydrogen atom is replaced by an alkylsulfanyl radical ordinarily having 1 to 4 C atoms. Examples thereof are CH$_2$—SCH$_3$, CH$_2$—SC$_2$H$_5$, n-propylsulfanylmethyl, CH$_2$—SCH(CH$_3$)$_2$, n-butylsulfanylmethyl, (1-methylpropsulfanyl)methyl, (2-methylpropsulfanyl)methyl, CH$_2$—OC(CH$_3$)$_3$, 2-(methylsulfanyl)ethyl, 2-(ethylsulfanyl)ethyl, 2-(n-propylsulfanyl)ethyl, 2-(1-methylethylsulfanyl)ethyl, 2-(n-butylsulfanyl)ethyl, 2-(1-methylpropylsulfanyl)ethyl, 2-(2-methylpropylsulfanyl)ethyl, 2-(1,1-dimethylethylsulfanyl)ethyl, 2-(methylsulfanyl)propyl, 2-(ethylsulfanyl)propyl, 2-(n-propylsulfanyl)propyl, 2-(1-methylethylsulfanyl)propyl, 2-(n-butylsulfanyl)propyl, 2-(1-methylpropylsulfanyl)propyl, 2-(2-methylpropylsulfanyl)propyl, 2-(1,1-dimethylethylsulfanyl)propyl, 3-(methylsulfanyl)propyl, 3-(ethylsulfanyl)propyl, 3-(n-propylsulfanyl)propyl, 3-(1-methylethylsulfanyl)propyl, 3-(n-butylsulfanyl)propyl, 3-(1-methylpropylsulfanyl)propyl, 3-(2-methylpropylsulfanyl)propyl, 3-(1,1-dimethylethylsulfanyl)propyl, 2-(methylsulfanyl)butyl, 2-(ethylsulfanyl)butyl, 2-(n-propylsulfanyl)butyl, 2-(1-methylethylsulfanyl)butyl, 2-(n-butylsulfanyl)butyl, 2-(1-methylpropylsulfanyl)butyl, 2-(2-methylpropylsulfanyl)butyl, 2-(1,1-dimethylethylsulfanyl)butyl, 3-(methylsulfanyl)butyl, 3-(ethylsulfanyl)butyl, 3-(n-propylsulfanyl)butyl, 3-(1-methylethylsulfanyl)butyl, 3-(n-butylsulfanyl)butyl, 3-(1-methylpropylsulfanyl)butyl, 3-(2-methylpropylsulfanyl)butyl, 3-(1,1-dimethyl-ethylsulfanyl)butyl, 4-(methylsulfanyl)butyl, 4-(ethylsulfanyl)butyl, 4-(n-propylsulfanyl)butyl, 4-(1-methylethylsulfanyl)butyl, 4-(n-butylsulfanyl)butyl, 4-(1-methylpropylsulfanyl)butyl, 4-(2-methylpropylsulfanyl)butyl, 4-(1,1-dimethylethylsulfanyl)butyl, etc.

"Alkylen" or "Alkanediyl": a saturated hydrocarbon chain having ordinarily from 1 to 4 carbon atoms, such as methylen (—CH$_2$—), 1,2-ethylen (—CH$_2$CH$_2$—), 1,1-ethanediyl (—CH(CH$_3$)—), 1,2-propanediyl, 1,3-propanediyl, 1,4-butanediyl, 1,2-butanediyl, 1,3-butanediyl, 1-methyl-1,2-propanediyl, 2-methyl-1,3-propanediyl, 1-methyl-1,1-ethanediyl, 1-methyl-1,2-propanediyl etc.

Saturated or partially unsaturated 4- to 7-membered monocarbocyclic radicals include cycloalkyl as defined above and cycloalkenyl having ordinarily from 4 to 7 carbon atoms as ring members, e.g. 1-cyclobuten-1-yl, 2-cyclobutenyl, 1-cyclopentenyl, 2-cyclopentenyl, 1-cyclohexenyl, 2-cyclohexenyl, 3-cyclohexenyl, 1-cycloheptenyl, 2-cycloheptenyl, 3-cycloheptenyl.

Saturated or partially unsaturated 7- to 10-membered bicarbocyclic radicals include bicyclic carbocyclic radicals which ordinarily have from 7 to 10 carbon atoms as ring members and which are saturated or which have one or more, e.g. one or two C=C double bonds, or which include a monounsaturated carbocycle where the double bond is part of a fused benzene ring, e.g. bicyclo[2,2,1]-1-heptyl, bicyclo[2,2,1]-2-heptyl, bicyclo[2,2,1]-7-heptyl, bicyclo[3,3,0]-1-octyl, bicyclo[3,3,0]-2-octyl, bicyclo[3,3,0]-3-octyl, bicyclo[2,2,2]-1-octyl, bicyclo[2,2,2]-2-octyl, bicyclo[3,2,1]-1-octyl, bicyclo[3,2,1]-2-octyl, bicyclo[3,2,1]-6-octyl, bicyclo[3,2,1]-8-octyl, bicyclo[4,3,0]-1-nonyl, bicyclo[4,3,0]-2-nonyl, bicyclo[4,3,0]-3-nonyl, bicyclo[4,3,0]-7-nonyl, bicyclo[4,3,0]-8-nonyl, bicyclo[4,4,0]-1-decyl, bicyclo[4,4,0]-2-decyl, bicyclo[4,4,0]-3-decyl, bicyclo[2,2,1]-hept-2-en-1-yl, bicyclo[2,2,1]-hept-2-en-2-yl, bicyclo[2,2,1]-hept-2-en-5-yl, bicyclo[2,2,1]-hept-2-en-7-yl, bicyclo[2,2,2]-oct-2-en-1-yl, bicyclo[2,2,2]-oct-2-en-2-yl, bicyclo[2,2,2]-oct-2-en-5-yl, bicyclo[2,2,2]-oct-2-en-7-yl, bicyclo[3,3,0]-2-octen-1-yl, bicyclo[3,3,0]-2-octen-2-yl, bicyclo[3,3,0]-2-octen-3-yl, bicyclo[3,3,0]-2-octen-4-yl, bicyclo[3,3,0]-2-octen-5-yl, bicyclo[3,3,0]-2-octen-6-yl, bicyclo[3,3,0]-2-octen-7-yl, bicyclo[3,3,0]-2-octen-8-yl, inden-1-yl, inden-2-yl, inden-4-yl, inden-6-yl, tetrahydro-1-naphthyl, tetrahydro-2-naphthyl, tetrahydro-5-naphthyl, tetrahydro-6-naphthyl, etc.

Heterocyclyl: a heterocyclic radical which may be saturated or partly unsaturated and which may be a monocyclic heterocyclic radical ordinarily having 3, 4, 5, 6, 7 or 8 ring atoms or a heterobicyclic radical ordinarily having 7, 8, 9 or 10 ring atoms, where ordinarily 1, 2, 3 or 4, in particular 1, 2 or 3, of the ring atoms are heteroatoms such as N, S or O, or heteroatom groups such as S(=O) or S(=O)$_2$ besides carbon atoms as ring members.

Examples of saturated heteromonocycles are in particular:

Saturated heteromonocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3- or 4-membered saturated rings such as 2-oxiranyl, 2-oxetanyl, 3-oxetanyl, 2-aziridinyl, 3-thiethanyl, 1-azetidinyl, 2-azetidinyl.

C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2- oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:
piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heteromonocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6- dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:
2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:
1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Examples of saturated or partially unsaturated heterobicycles are in particular radicals corresponding to saturated or partially unsaturated bicarbocyclic radicals, wherein 1, 2 or 3 CH or $CH_2$ moieties have been replaced by N, NH, O, S, S(=O) or $S(=O)_2$, such as 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, dihydroindolyl, dihydroindolizynyl, dihydroisoindolyl, dihydroquinolinyl, dihydroisoquinolinyl, chromenyl and chromanyl.

Hetaryl: a 5- or 6-membered aromatic heteromonocyclic radical (also termed 5- or 6-membered monocyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members and a 8- to 10-membered aromatic heterobicyclic radical (also termed 8- to 10-membered bicyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members: for example C-bonded, 5-membered monocyclic hetaryl having 1, 2 or 3 or 4 nitrogen atoms or a heteroatom selected from oxygen and sulfur and, if appropriate, having 1, 2 or 3 nitrogen atoms as ring members, such as:
2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered monocyclic hetaryl having 1, 2 or 3 nitrogen atoms as ring members, such as:
pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:
pyrrol-1-yl, pyrazol-1-yl, imidazol-1-yl, 1,2,3-triazol-1-yl, 1,2,4-triazol-1-yl, tetrazol-1-yl.
bicyclic 8- to 10-membered hetaryl, hetaryl which has one of the aforementioned 5- or 6-membered heteroaromatic rings and a further aromatic carbocycle or 5- or 6-membered heterocycle fused thereto, for example a fused benzene, thiophene, furane, pyrrole, pyrazole, imidazole, pyridine or pyrimidine ring. These bicyclic hetaryl include for example quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Hetarylalkyl: a hetaryl radical as defined above which is linked via an alkylene group, in particular via a methylene, 1,1-ethylene or 1,2-ethylene group, to the remainder of the molecule.

The expression "optionally substituted" in the context of the present invention means that the respective moiety is unsubstituted or has 1, 2 or 3, in particular 1, substituents which are selected from halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

One embodiment of the invention relates to compounds of formula I, where

Q is O or S;
$X^1$ is N or CH;
$X^2$ is O or S;
$R^1$ is a moiety $Y^1$-$Cyc^1$;
$R^2$ is selected from the group consisting of hydrogen, halogen, OH, $C_1$-$C_4$-alkyl, trimethylsilyl, hydroxy-$C_1$-$C_4$-alkyl, $C_1$-$C_4$ alkoxy $C_1$-$C_4$ alkyl $C_1$-$C_4$-alkoxy, $C_1$-$C_4$-alkoxy-$C_1$-$C_4$-alkoxy, $C_2$-$C_4$-alkenyloxy, $C_1$-$C_4$-fluoroalkyl, $C_1$-$C_4$-fluoroalkoxy, $C_3$-$C_2$-cycloalkyl, optionally substituted by 1, 2 or 3 methyl groups, fluorinated $C_3$-$C_2$-cycloalkyl, $C_3$-$C_2$-cycloalkyloxy, CN and $NR^{x1}R^{x2}$;
$R^{x1}$ and $R^{x2}$, independently of each other are selected from the group consisting of hydrogen, $C_1$-$C_4$-alkyl, $C_1$-$C_4$-fluoroalkyl, $C_1$-$C_4$-alkoxy-$C_1$-$C_4$-alkyl, hydroxy-$C_1$-$C_4$-alkyl, and $C_3$-$C_6$-cycloalkyl;
$R^3$ is a moiety $Y^3$-$Cyc^3$;
$R^4$ is unsubstituted $C_1$-$C_4$ alkyl $C_1$-$C_4$-fluoroalkyl, $C_3$-$C_6$-cycloalkyl, fluorinated $C_3$-$C_7$-cycloalkyl, or $C_1$-$C_4$-alkyl which carries one or two radicals $R^{44}$
$R^{44}$ is selected from the group consisting of $C_1$-$C_4$-alkoxy, $C_1$-$C_4$-fluoroalkoxy, CN, OH, $NR^{x3}R^{x4}$, $C_3$-$C_6$-cycloalkyl, $C_3$-$C_6$-cycloalkyloxy, a 3- to 10-membered saturated, C-bound mono- or bicyclic heterocyclyl, 3- to 10-membered saturated, C-bound mono- or bicyclic heterocyclyloxy, where the last for groups of radicals are unsubstituted, partially or completely fluorinated and/or carry 1, 2, or 4 radicals selected from the group consisting of OH, $C_1$-$C_4$-alkyl, $C_1$-$C_4$-fluoroalkyl, $C_1$-$C_4$-alkoxy and $C_1$-$C_4$-fluoroalkoxy, and where C-bound heterocyclyl and C-bound heterocyclyloxy has 1, 2, 3 or 4 heteroatoms or heteroatom containing groups selected from the group consisting of O, N, S, SO and $SO_2$ as ring members;

where $R^{x3}$ and $R^{x4}$, independently of each other, are selected from the group consisting of hydrogen, $C_1$-$C_4$-alkyl, $C_1$-$C_4$-fluoroalkyl, $C_1$-$C_4$ alkoxy $C_1$-$C_4$ alkyl hydroxy-$C_1$-$C_4$-alkyl, and $C_3$-$C_6$-cycloalkyl, or $NR^{x3}R^{x4}$ is a saturated N-bound 3- to 7-membered, nitrogen heterocycle which may have 1, 2 or 3 further different or identical heteroatoms or heteroatom containing groups selected from the group consisting of O, N, S, SO and $SO_2$ as ring members and which may carry 1, 2, 3, 4, 5 or 6 substituents selected from the group consisting of halogen, OH, $C_1$-$C_4$-alkyl and $C_1$-$C_4$-alkoxy;

$Y^1$, $Y^3$ independently of each other are selected from the group consisting of a chemical bond, $CH_2$, O, O—$CH_2$, C(O)O, C(O), $NR^y$, $NR^y$—$CH_2$, $S(O)_2$—$NR^y$, C(O)—$NR^y$, S, S(O), $S(O)_2$, C(O)—O—$CH_2$, C(O)—$NR^y$—$CH_2$, 1,2-ethanediyl, 1,2-ethenediyl or 1,2-ethynediyl, where $R^y$ is selected from the group consisting of hydrogen, $C_1$-$C_4$-alkyl, $C_1$-$C_4$-alkylcarbonyl, $C_1$-$C_4$-alkylsulfonyl, $C_1$-$C_4$-fluoroalkylsulfonyl;

$Cyc^1$, $Cyc^3$ independently of each other are selected from the group consisting of phenyl, naphthyl, $C_3$-$C_8$-cycloalkyl, 3- to 8-membered saturated or partially unsaturated heteromonocyclic radicals, saturated or partially unsaturated 7- to 10 membered heterobicyclic radicals, 5- or 6-membered monocyclic hetaryl, and 8- to 10 membered bicyclic hetaryl, where the saturated or partially unsaturated heteromonocyclic and heterobicyclic radicals have 1, 2, 3 or 4 heteroatoms or heteroatom containing groups as ring members, which are selected from the group consisting of O, S, SO, $SO_2$ and N, and where the 5- or 6-membered monocyclic hetaryl and the 8- to 10-membered bicyclic hetaryl have 1, 2, 3 or 4 heteroatoms as ring members, which are selected from the group consisting of O, S and N, where $C_3$-$C_8$-cycloalkyl, the saturated or partially unsaturated heteromonocyclic and heterobicyclic radicals are unsubstituted or carry 1, 2, 3, 4 or 5 radicals $R^{C1}$ or one radical $Y'$—$R^{C2}$ and 0, 1, 2, 3 or 4 radicals $R^{C1}$;

where phenyl, naphthyl, the saturated or partially unsaturated heteromonocyclic and heterobicyclic radicals and the mono and bicyclic heteroaromatic radicals are unsubstituted or carry 1, 2, 3, 4 or 5 radicals $R^{C3}$ or one radical $Y'$—$R^{C2}$ and 0, 1, 2, 3 or 4 radicals $R^{C3}$;

where $R^{C1}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^a$, Z—$C(O)OR^b$, Z—$C(O)NR^cR^d$, $NR^gSO_2R^h$, $S(O)_2NR^cR^d$ and Z—$NR^eR^f$, where $R^a$, $R^h$ independently of each other are selected from the group consisting of hydrogen, $C_1$-$C_4$-alkyl and $C_1$-$C_4$-fluoroalkyl, $R^b$, $R^g$ independently of each other are selected from the group consisting of hydrogen, $C_1$-$C_4$-alkyl, $C_2$-$C_4$-alkenyl and $C_1$-$C_4$-fluoroalkyl, $R^c$, $R^d$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, $R^e$, $R^f$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, Z is a covalent bond or $C_1$-$C_4$-alkanediyl, or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from the group consisting of O, S and N;

or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are selected from the group consisting of O, S and N, or two radicals $R^{C1}$ which are bound at the same carbon atom may form an oxygen atom, where the fused and the spiro radicals are unsubstituted or carry 1, 2, 3 or 4 radicals $R^{C4}$;

Y' is a chemical bond, $CH_2$, O, O—$CH_2$, C(O), $S(O)_2$, $NR^{y'}$, $NR^{y'}$—$CH_2$ or $NR^{y'}$—$S(O)_2$, where $R^{y'}$ is selected from the group consisting of hydrogen, $C_1$-$C_4$-alkyl, $C_1$-$C_4$-alkylcarbonyl, $C_1$-$C_4$-alkylsulfonyl, $C_1$-$C_4$-fluoroalkylsulfonyl;

$R^{C2}$ is a carbocyclic or heterocyclic radical selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from the group consisting of O, S and N, and 5- or 6-membered heteroaromatic radicals, having 1, 2 or 3 heteroatoms as ring members, which are selected from the group consisting of O, S and N, where the carbocyclic and the heterocyclic radical are unsubstituted or carry 1, 2, 3, 4 or 5 radicals $R^{C4}$;

$R^{C3}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, C(O)$R^a$, Z—C(O)O$R^b$, Z—C(O)N$R^cR^d$, $NR^gSO_2R^h$, $S(O)_2NR^cR^d$ and Z—$NR^eR^f$, wherein $R^a$, $R^b$, $R^c$, $R^d$, $R^e$, $R^f$, $R^g$ and $R^h$ have the same meaning as defined above, or two radicals $R^{C3}$ which are bound at adjacent carbon atoms may form a saturated or partially unsaturated fused 5- or 6-membered carbocyclic radical or a saturated or partially unsaturated fused 5- or 6-membered heterocyclic radical having 1, 2 or 3 heteroatoms as ring members, which are selected from the group consisting of O, S and N, where the carbocyclic and the heterocyclic radical are unsubstituted or carry 1, 2, 3, 4 or 5 radicals $R^{C4}$;

$R^{C4}$ is selected from the group consisting of hydrogen, halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, C(O)$R^a$, benzyl, Z—C(O)O$R^b$, Z—C(O)N$R^cR^d$, $S(O)_2NR^cR^d$ and Z—$NR^eR^f$, where, Z, $R^a$, $R^b$, $R^c$, $R^d$, $R^e$ and $R^f$ are as defined above or two radicals $R^{C4}$ which are bound at the same atom may form an oxygen atom;

and the N-oxides, the prodrugs, the tautomers and the hydrates thereof, and the pharmaceutically acceptable salts thereof.

In relation to their use as inhibitors of PDE10A, the variables Q, $X^1$, $X^2$, $Y^1$, $Y^3$, $R^1$, $R^2$, $R^3$, $R^4$, $Cyc^1$ and $Cyc^3$ preferably have the following meanings, where these represent, both considered on their own and in combination with at least one other or all, special configurations of the compounds of the formula I:

In particular embodiments of the invention, the variable $X^1$ is CH.

In further particular embodiments of the invention, the variable $X^1$ is N.

In further particular embodiments of the invention, the variable $X^3$ is S.

In further particular embodiments of the invention, the variable Q is O.

In further particular embodiments of the invention, $X^1$ is N and $X^2$ is S.

In yet further particular preferred embodiments, $X^1$ is N and $X^2$ is O.

In particularly preferred embodiments of the invention, $X^1$ is N, $X^2$ is S and Q is O, i.e. formula I can be described by the following formula I.A:

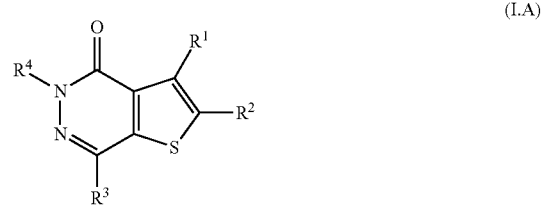

(I.A)

where $R^1$, $R^2$, $R^3$ and $R^4$ are as described herein.

In yet further particularly preferred embodiments of the invention, $X^1$ is N, $X^2$ is O and Q is O, i.e. formula I can be described by the following formula I.B:

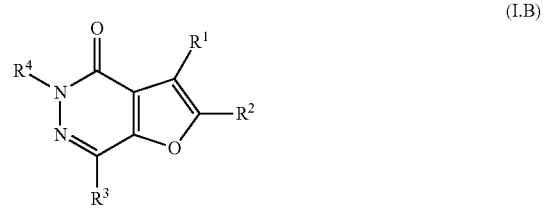

(I.B)

where $R^1$, $R^2$, $R^3$ and $R^4$ are as described herein.

In yet further particularly preferred embodiments of the invention, $X^1$ is CH, $X^2$ is S and Q is O, i.e. formula I can be described by the following formula I.C:

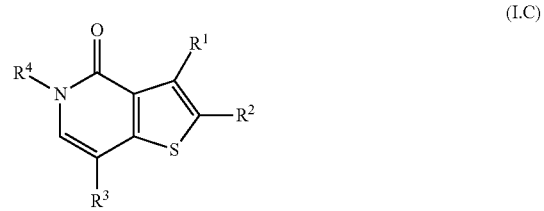

(I.C)

where $R^1$, $R^2$, $R^3$ and $R^4$ are as described herein.

In yet further particularly preferred embodiments of the invention, $X^1$ is CH, $X^2$ is O and Q is O, i.e. formula I can be described by the following formula I.D:

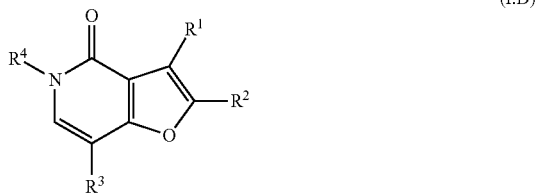

(I.D)

where $R^1$, $R^2$, $R^3$ and $R^4$ are as described herein.

In the moiety $Y^1$-$Cyc^1$, i.e. in the radical $R^1$ of formulae I, I.A, I.B, I.C and I.D, the bivalent radical $Y^1$ is in particular selected from the group consisting of a chemical bond, O, NH, $CH_2$, 1,2-ethenyl, ethynyl, C(O), $NHCH_2$, C(O)NH and C(O)$NHCH_2$, more particularly selected from the group consisting of O, NH and a chemical bond. Especially, $Y^1$ is a chemical bond.

In the moiety $Y^1$-$Cyc^1$, i.e. in the radical $R^1$ of formulae I, I.A, I.B, I.C and I.D, the cyclic radical $Cyc^1$ is in particular selected from the radicals of the following groups (i) and (ii):

(i) Group (i) radicals are selected from the group consisting of saturated 4-, 5-, 6-, 7- or 8-membered heteromonocycles and saturated 7-, 8-, 9- or 10-membered heterobicycles, where the heteromonocycles and the heterobicycles have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5 radicals $R^{C1}$, in particular 1, 2, or 3 radicals $R^{C1}$, or one radical Y'—$R^{C2}$ and 0, 1, 2, 3 or 4 radicals $R^{C1}$, in particular 0, 1, or 2 radicals $R^{C1}$, where $R^{C1}$, $R^{C2}$ and Y' are as defined herein and wherein Y' is in particular a chemical bond;

(ii) Group (ii) radicals are selected from the group consisting of phenyl, 5- or 6-membered monocyclic hetaryl, and 9- or 10 membered bicyclic hetaryl, where hetaryl has one heteroatom, selected from O, S and N as ring member and optionally one or two further nitrogen atoms as ring members, where phenyl and the hetaryl radical are unsubstituted or either carry, independently of each other, 1, 2, 3, 4 or 5 radicals $R^{C3}$, in particular 1, 2, or 3 radicals $R^{C3}$, or one radical Y'—$R^{C2}$ and 0, 1, 2, 3 or 4 radicals $R^{C3}$, in particular 0, 1, or 2 radicals $R^{C3}$.

In a first particular group of embodiments, $Cyc^1$ is a group (i) radical.

If $Cyc^1$ is a group (i) radical, $Y^1$ is in particular selected from a single bond, O and NH. In this regard, $R^{C1}$ is preferably selected from the group consisting of fluorine, chlorine, CN, methyl, difluoromethyl, trifluoromethyl, methoxy and $NH_2$. In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals $R^{C4}$, which are preferably selected from fluorine, chlorine, CN, methyl, difluoromethyl, trifluoromethyl, methoxy and $NH_2$.

If $Cyc^1$ is a group (i) radical, the moiety $Cyc^1$ is in particular an unsubstituted cyclic radical or a cyclic radical which carries 1 or 2 radicals $R^{C1}$.

If $Cyc^1$ is a group (i) radical, $Cyc^1$ is in particular a saturated 4-, 5-, 6- or 7-membered heteromonocycle, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle is unsubstituted or carries 1, 2, or 3 radicals $R^{C1}$, where $R^{C1}$ is as defined herein If $Cyc^1$ is a group (i) radical, the moiety $Y^1$-$Cyc^1$ is in more particularly selected from the group consisting of 1-piperidinyl, 4,4-difluoro-1-piperidinyl, 4-hydroxylpiperidin-1-yl, 4-piperidinyl, 1-methyl-4-piperidinyl, 1-piperazinyl, 4-methyl-1-piperazinyl, 4-(tert.-butyloxycarbonyl)piperazin-1-yl, 1-piperazinylmethyl, 4-methyl-1-piperazinylmethyl, 1-piperazinylcarbonyl, 4-methyl-1-piperazinylcarbonyl, morpholin-4-yl, morpholin-4-ylmethyl, morpholin-4-ylcarbonyl, azepane-1-yl, 1,4-oxazepan-4-yl, thiomorpholin-4-yl, 1-oxothiomorpholin-4-yl, N-(oxetan-3-yl)amino, 1,1-dioxothiomorpholin-4-yl and oxetan-3-ylamino.

If $Cyc^1$ is a group (i) radical, the moiety $Y^1$-$Cyc^1$ is especially 4-morpholinyl, oxetan-3-ylamino or 4-morpholinylmethyl.

In a further particular group of embodiments, $Cyc^1$ is a group (ii) radical.

If $Cyc^1$ is a group (ii) radical, $Y^1$ is in particular a single bond.

In this regard, $R^{C3}$ is preferably selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, C(O)$NH_2$ and $NH_2$, especially from the group consisting of fluorine, chlorine, OH, CN, methyl, difluoromethyl, trifluoromethyl, methoxy, 2-methoxyethyl, C(O)$NH_2$, C(O)$OCH_3$ and $NH_2$, or, if $Cyc^1$ is phenyl, two radicals $R^{C3}$ which are bound to adjacent carbon atoms, together with the phenyl ring to which they are bound, form a bicyclic heterocyclic radical, which is selected from the group consisting of 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl. In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated or aromatic heteromonocyclic radicals, having 1, 2 or 3 heteroatoms as ring members, which are selected from O, S and N, such as 1-piperidinyl, 1-piperazinyl, 4-methyl-1-piperazinyl, 4-morpholinyl, pyridyl, pyrimidinyl, 1-pyrazolyl, or 1-imidazolyl, where phenyl the saturated or aromatic heteromonocyclic radical are unsubstituted or carry 1, 2 or 3 radicals $R^{C4}$, which are as defined above and which are preferably selected from the group consisting of fluorine, chlorine, CN, methyl, difluoromethyl, trifluoromethyl, methoxy and $NH_2$.

If $Cyc^1$ is a group (ii) radical, the moiety $Y^1$-$Cyc^1$ is in particular selected from the group consisting of phenyl, 5- or 6-membered monocyclic hetaryl selected from the group consisting of pyridyl, pyrimidinyl, furyl, thienyl, pyrrolyl, imidazolyl, pyrazolyl, oxazolyl and thiazolyl, 9- or 10-membered bicyclic hetaryl selected from the group consisting of indolyl, quinolinyl, isoquinolinyl, quinazolinyl, benzimidazolyl, 1,3-bezoxazolyl, 1,3-benzothiazolyl, benzotriazolyl, benzopyrazolyl, benzothienyl and benzofuryl, where phenyl, the monocyclic and bicyclic hetaryl are unsubstituted or carry 1, 2 or 3 radicals $R^{C3}$ which are in particular selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, C(O)NH$_2$ and NH$_2$, especially from the group consisting of fluorine, chlorine, OH, CN, methyl, difluoromethyl, trifluoromethyl, methoxy, 2-methoxyethyl, C(O)NH$_2$, C(O)OCH$_3$ and NH$_2$, or carry one radical Y'—$R^{C2}$, where Y is a bond, CH$_2$ or C(O) and $R^{C2}$ is in particular 1-piperidinyl, 1-piperazinyl, 4-methyl-1-piperazinyl, 4-morpholinyl, pyridyl, pyrimidinyl, 1-pyrazolyl, or 1-imidazolyl, or, if Cyc$^1$ is phenyl, two radicals $R^{C3}$ which are bound to adjacent carbon atoms, together with the phenyl ring to which they are bound, form a bicyclic heterocyclic radical, which is in particular selected from 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

If Cyc$^1$ is a group (ii) radical, Cyc$^1$ is more particularly selected from the group consisting of phenyl and 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C3}$, where $R^{C3}$, $R^{C2}$ and Y' are as defined herein and where Y', if present, is preferably a chemical bond.

If Cyc$^1$ is a group (ii) radical, Cyc$^1$ is especially selected from the group consisting of 4-pyridyl, 3-pyridyl, pyrimidin-5-yl, 3-methoxyphenyl, 3-(1H-pyrazol-1-yl)phenyl, pyridazin-4-yl, 2-methylpyrimidin-5-yl, 2-hydroxyphenyl and 4-hydroxyphenyl.

If Cyc$^1$ is a group (ii) radical, $R^1$ is especially selected from the group consisting of 4-pyridyl, 3-pyridyl, pyrimidin-5-yl, 3-methoxyphenyl, 3-(1H-pyrazol-1-yl)phenyl, pyridazin-4-yl, 2-methylpyrimidin-5-yl, 2-hydroxyphenyl and 4-hydroxyphenyl.

In formulae I, I.A, I.B, I.C and I.D, the variable $R^2$ is in particular selected from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl. In formulae I, I.A, I.B, I.C and I.D, $R^2$ is especially hydrogen.

In the moiety Y$^3$-Cyc$^3$, i.e. in the radical $R^3$ of formulae I, I.A, I.B, I.C and I.D, the bivalent radical Y$^3$ is in particular selected from the group consisting of a O, NH, CH$_2$, C(O), OCH$_2$, NHCH$_2$, C(O)NH and C(O)NHCH$_2$, more particularly selected from the group consisting of O, NH, OCH$_2$, NHCH$_2$ and a chemical bond. Likewise preference is given to compounds of formulae I, I.A, I.B, I.C and I.D, where the bivalent radical Y$^3$ is selected from OCH(CH$_3$) and OCH$_2$C(O)NH.

In the moiety Y$^3$-Cyc$^3$, i.e. in the radical $R^3$ of formulae I, I.A, I.B, I.C and I.D, the cyclic radical Cyc$^3$ is in particular selected from the radicals of the following groups (i) and (ii):

(i) Group (i) radicals are selected from the group consisting of $C_3$-$C_7$-cycloalkyl, saturated 4-, 5-, 6-, 7- or 8-membered heteromonocycles and saturated 7-, 8-, 9- or 10-membered heterobicycles, where the heteromonocycles and the heterobicycles have one nitrogen or oxygen atom as ring member and may have one further heteroatom or heteroatom group as ring member, which is selected from the group consisting of O, S, S(=O), S(=O)$_2$ and N, where $C_3$-$C_2$-cycloalkyl, the saturated heteromonocycle and the saturated heterobicycle are unsubstituted or carry 1, 2, 3, 4 or 5 radicals $R^{C1}$, in particular 1, 2, or 3 radicals $R^{C1}$, or one radical Y'—$R^{C2}$ and 0, 1, 2, 3 or 4 radicals $R^{C1}$, in particular 0, 1, or 2 radicals $R^{C1}$, where $R^{C1}$, $R^{C2}$ and Y' are as defined herein and wherein Y' is in particular a chemical bond;

(ii) Group (ii) radicals are selected from the group consisting of phenyl, 5- or 6 membered monocyclic hetaryl, and 9- or 10 membered bicyclic hetaryl, where hetaryl has one heteroatom, selected from O, S and N as ring member and optionally one or two further nitrogen atoms as ring members, where phenyl and the hetaryl radical are unsubstituted or either carry, independently of each other, 1, 2, 3, 4 or 5 radicals $R^{C3}$, in particular 1, 2, or 3 radicals $R^{C3}$, or one radical Y'—$R^{C2}$ and 0, 1, 2, 3 or 4 radicals $R^{C3}$, in particular 0, 1, or 2 radicals $R^{C3}$.

In a first particular group of embodiments, Cyc$^3$ is a group (i) radical.

If Cyc$^3$ is a group (i) radical, Y$^1$ is in particular selected from a single bond, O and NH. In this regard, $R^{C1}$ is preferably selected from the group consisting of fluorine, chlorine, CN, methyl, difluoromethyl, trifluoromethyl, methoxy and NH$_2$. In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals $R^{C3}$, which are preferably selected from fluorine, chlorine, CN, methyl, difluoromethyl, trifluoromethyl, methoxy and NH$_2$.

If Cyc$^3$ is a group (i) radical, the moiety Cyc$^3$ is in particular an unsubstituted radical or carries 1 or 2 radicals $R^{C1}$.

If Cyc$^3$ is a group (i) radical, Cyc$^3$ is in particular a saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein If Cyc$^3$ is a group (i) radical, the moiety Y$^3$-Cyc$^3$ is in more particularly selected from the group consisting of cyclohexyloxy, cyclohexylmethyloxy, 4,4-difluoro-1-cyclohexyloxy, 4,4-difluoro-1-cyclohexylmethyloxy, 1-piperidinyl, 4,4-difluoro-1-piperidinyl, 4-hydroxylpiperidin-1-yl, 4-piperidinyl, 1-methyl-4-piperidinyl, 1-piperidinylmethyl, 4,4-difluoro-1-piperidinylmethyl, 4-hydroxylpiperidin-1-ylmethyl, 4-piperidinylmethyloxy, 1-methyl-4-piperidinylmethyloxy, 1-piperazinyl, 4-methyl-1-piperazinyl, 4-(tert.-butyloxycarbonyl)piperazin-1-yl, 1-piperazinylmethyl, 4-methyl-1-piperazinylmethyl, 1-piperazinylmethyloxy, 4-methyl-1-piperazinylmethyloxy, 1-piperazinylcarbonyl, 4-methyl-1-piperazinylcarbonyl, morpholin-4-yl, morpholin-4-ylmethyl, morpholin-4-ylcarbonyl, azepane-1-yl, 1,4-oxazepan-4-yl, thiomorpholin-4-yl, 1-oxothiomorpholin-4-yl, N-(oxetan-3-yl)amino, 1,1-dioxothiomorpholin-4-yl and oxetan-3-ylamino, even more particularly from the group consisting of 1-piperidinyl, 4,4-difluoro-1-piperidinyl, 4-hydroxylpiperidin-1-yl, 4-piperidinyl, 1-methyl-4-piperidinyl, 1-piperazinyl, 4-methyl-1-piperazinyl, 4-(tert.-butyloxycarbonyl)piperazin-1-yl, 1-piperazinylmethyl, 4-methyl-1-piperazinylmethyl, 1-piperazinylcarbonyl, 4-methyl-1-piperazinylcarbonyl, morpholin-4-yl, morpholin-4-ylmethyl, morpholin-4-ylcarbonyl, azepane-1-yl, 1,4-oxazepan-4-yl, thiomorpholin-4-yl, 1-oxothiomorpholin-4-yl, N-(oxetan-3-yl)amino, 1,1-dioxothiomorpholin-4-yl and oxetan-3-ylamino In a further particular group of embodiments, $Cyc^3$ is a group (ii) radical.

If $Cyc^3$ is a group (ii) radical, $Y^3$ is in particular a single bond, O, NH, $OCH_2$, $OCH(CH_3)$, or $NHCH_2$ and more particularly a a single bond, 0, $OCH_2$ or $NHCH_2$. Likewise, $Y^3$ is in particular $OCH_2C(O)NH$.

In this regard, $R^{C3}$ is preferably selected from the group consisting of $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, $C(O)O$—$C_1$-$C_4$-alkyl, $C(O)NH_2$ and $NH_2$, especially from the group consisting of fluorine, chlorine, OH, CN, methyl, difluoromethyl, trifluoromethyl, methoxy, 2-methoxyethyl, $C(O)NH_2$, $C(O)OCH_3$ and $NH_2$, or, if $Cyc^3$ is phenyl, two radicals $R^{C3}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl. In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated or aromatic heteromonocyclic radicals, having 1, 2 or 3 heteroatoms as ring members, which are selected from O, S and N, where phenyl, the saturated or aromatic heteromonocyclic radical is unsubstituted or carries 1, 2 or 3 radicals $R^{C4}$, which are as defined above and which are preferably selected from fluorine, chlorine, CN, methyl, difluoromethyl, trifluoromethyl, methoxy and $NH_2$.

If $Cyc^3$ is a group (ii) radical, the moiety $Cyc^3$ is in particular selected from the group consisting of phenyl, 5- or 6-membered monocyclic hetaryl selected from the group consisting of pyridyl, pyrimidinyl, furyl, thienyl, pyrrolyl, imidazolyl, pyrazolyl, oxazolyl and thiazolyl, 9- or 10-membered bicyclic hetaryl selected from the group consisting of indolyl, quinolinyl, isoquinolinyl, quinazolinyl, benzimidazolyl, 1,3-benzoxazolyl, 1,3-benzthiazolyl, benzotriazolyl, benzopyrazolyl, benzothienyl and benzofuryl, where phenyl and hetaryl are unsubstituted or carry 1, 2 or 3 radicals $R^{C3}$ which are in particular selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, $C(O)O$—$C_1$-$C_4$-alkyl, $C(O)NH_2$ and $NH_2$, or carry one radical $Y'$—$R^{C2}$, where Y is a bond, $CH_2$ or $C(O)$ and $R^{C2}$ is in particular phenyl, pyridyl, pyrimidinyl, 1-pyrazolyl, 1-imidazolyl, 1-piperidinyl, 1-piperazinyl, 4-methyl-1-piperazinly or 4-morpholinyl, or, if $Cyc^1$ is phenyl, two radicals $R^{C3}$ which are bound to adjacent carbon atoms, together with the phenyl ring to which they are bound, form a bicyclic heterocyclic radical, which is in particular selected from
2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

If $Cyc^3$ is a group (ii) radical, $Cyc^3$ is more particularly selected from the group consisting of phenyl and 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical $Y'$—$R^{C2}$ and 0, 1, 2, 3 or 4, in particular 0, 1 or 2 radicals $R^{C3}$, where $R^{C3}$, $R^{C2}$ and $Y'$ are as defined herein and where $Y'$, if present, is preferably a chemical bond.

If $Cyc^3$ is a group (ii) radical, the radical $Y^3$ is in particular a chemical bond, O, $OCH_2$, $OCH(CH_3)$ or $NHCH_2$ and $Cyc^3$ is selected from the group consisting of phenyl, 5- or 6-membered monocyclic hetaryl selected from the group consisting of pyridyl, pyrimidinyl, furyl, thienyl, pyrrolyl, imidazolyl, pyrazolyl, oxazolyl and thiazolyl, 9- or 10-membered bicyclic hetaryl selected from the group consisting of indolyl, quinolinyl, isoquinolinyl, quinazolinyl, 1,3-benzothiazolyl, 1,3-benzoxazolyl, benzimidazolyl, benzotriazolyl, benzopyrazolyl, benzothienyl and benzofuryl, where phenyl, monocyclic hetaryl and bicyclic hetaryl are unsubstituted or carry 1, 2 or 3 radicals $R^{C3}$ which are selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, $C(O)O$—$C_1$-$C_4$-alkyl, $C(O)NH_2$ and $NH_2$, or carry one radical $Y'$—$R^{C2}$, where Y' is a bond, $CH_2$ or $C(O)$ and $R^{C2}$ is phenyl, pyridyl, pyrimidinyl, 1-pyrazolyl, 1-imidazolyl, 1-piperidinyl, 1-piperazinyl, 4-methyl-1-piperazinly or 4-morpholinyl, or, if $Cyc^3$ is phenyl, two radicals $R^{C3}$ which are bound to adjacent carbon atoms, together with the phenyl ring to which they are bound, form a bicyclic heterocyclic radical, which is selected from 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

If $Cyc^3$ is a group (ii) radical, $Cyc^3$ is especially phenyl, 4-pyridyl, 3,4-dimethoxyphenyl, 1-methyl-1H-imidzaol-4-yl, 1-(2,2,2-trifluoroethyl)-1H-pyrazol-4-yl, 1,3-benzthiazol-2-yl, 3,5-dimethoxyphenyl, 3,4-dimethoxyphenyl, 3-cyanophenyl, 4-cyanophenyl, 1-(2-methoxyethyl)-1-H-pyrazol-4-yl, 5-methoxypridin-3-yl, 3-(difluoromethoxy)phenyl, 4-(difluoromethoxy)phenyl, 3-hydroxyphenyl, 1,3-benzoxazol-6-yl, pyridin-3-yl, thiazol-2-yl, 1-methylbenzimidazol-2-yl, pyridin-2-yl, 2-fluoropyridin-4-yl, 3-(methoxycarbonyl)phenyl, 3-(aminocarbonyl)phenyl or 2-chloro-6-methylpyridin-3-yl.

$R^3$ is especially selected from the group consisting of 4-pyridyl, 3,4-dimethoxyphenyl, 1-methyl-1H-imidzaol-4-yl, benzylamino, 1-(2,2,2-trifluoroethyl)-1H-pyrazol-4-yl, 1,3-benzthiazol-2-ylmethoxy, 3,5-dimethoxybenzyloxy, 3,4-dimethoxybenzyloxy, 3-cyanobenzyloxy, 4-cyanobenzyloxy, 3,5-dimethoxyphenoxy, 3,4-dimethoxyphenoxy, 3-cyanophenoxy, 4-cyanophenoxy, 1-(2-methoxyethyl)-1-H-pyrazol-4-yl, 5-methoxypridin-3-yl, 3-(difluoromethoxy)benzyloxy, 4-(difluoromethoxy)benzyloxy, 3-hydroxyphenyl, 1,3-benzoxazol-6-yl, pyridin-3-ylmethoxy, pyridin-2-ylmethoxy, 2-fluoropyridin-4-yl, 3-(methoxycarbonyl)benyzloxy, 3-(aminocarbonyl)benzyloxy, 2-chloro-6-methylpyridin-3-yloxy, thiazol-2-ylmethoxy, 1-methylbenzimidazol-2-ylmethoxy, 1-piperidinyl, 4-morpholinyl and 4-methypiperazin-1-yl.

In formulae I, I.A, I.B, I.C and I.D, $R^4$ is in particular different from hydrogen. In formulae I, I.A, I.B, I.C and I.D, $R^4$ is more particularly selected from the group consisting of $C_1$-$C_3$-alkyl, $C_1$-$C_2$-fluoroalkyl, or $C_1$-$C_2$-alkyl, which carries one of the radicals $R^{44}$, where $R^{44}$ is as defined above and where $R^{44}$ is in particular selected from the group consisting of methoxy, ethoxy, CN, OH, $C_3$-$C_6$-cycloalkyl and $NR^{x3}R^{x4}$, where $R^{x3}$ and $R^{x4}$ are as defined above. In particular $R^{x3}$ and $R^{x4}$ are independently of each other selected from hydrogen, $C_1$-$C_2$-alkyl, hydroxyl-$C_1$-$C_2$-alkyl, $C_1$-$C_2$-alkoxy-$C_1$-$C_2$-alkyl or $NR^{x3}R^{x4}$ is a saturated N-bound 4- or 6-membered heterocycle such as 1-piperidinyl, 1-pyrrolidinyl, 4-morpholinyl, 1-piperazinyl or 4-methyl-1-piperazinyl. $R^4$ is even more particularly selected from the group consisting of $C_1$-$C_3$-alkyl, $C_1$-$C_2$-fluoroalkyl, or $C_1$-$C_2$-alkyl, which carries one of the radicals $R^{44}$, where $R^{44}$ is selected from the group consisting of $C_3$-$C_6$-cycloalkyl. Especially, $R^4$ is selected from the group consisting of methyl, ethyl, 2,2,2-trifluoroethyl and cyclopropylmethyl.

Apart from that, the variables $R^{x1}$, $R^{x2}$, $Y'$, $R^{C1}$, $R^{C2}$, $R^{C3}$, $R^{C4}$, $R^a$, $R^b$, $R^c$, $R^d$, $R^e$, $R^f$, $R^g$, $R^h$, $R^y$, $R^{y'}$ and Z have in particular the following meanings, if not stated otherwise.

$R^{x1}$ and $R^{x2}$ are independently of each other selected from hydrogen, $C_1$-$C_2$-alkyl, hydroxyl-$C_1$-$C_2$-alkyl, $C_1$-$C_2$-alkoxy-$C_1$-$C_2$-alkyl or $NR^{x1}R^{x2}$ is a saturated N-bound 4- or 6-membered heterocycle such as 1-piperidinyl, 1-pyrrolidinyl, 4-morpholinyl, 1-piperazinyl or 4-methyl-1-piperazinyl;

Y' is a bond, $CH_2$ or C(O);

$R^{C1}$ is selected from the group consisting of fluorine, chlorine, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, $C(O)NH_2$ and $NH_2$, or if $R^{C1}$ is bound to phenyl, two radicals $R^{C1}$ which are bound to adjacent carbon atoms or phenyl, together with the phenyl ring to which they are bound, form a bicyclic heterocyclic radical, which is selected from 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

$R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated or aromatic heteromonocyclic radicals, having 1, 2 or 3 heteroatoms as ring members, which are selected from O, S and N, where phenyl the saturated or aromatic heteromonocyclic radical is unsubstituted or carries 1, 2 or 3 radicals $R^{C4}$. $R^{C2}$ is in particular phenyl, pyridyl, pyrimidinyl, 1-pyrazolyl, 1-imidazolyl, 1-piperidinyl, 1-piperazinyl, 4-methyl-1-piperazinly or 4-morpholinyl.

$R^{C3}$ is selected from the group consisting of $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, $C(O)NH_2$ and $NH_2$, especially from the group consisting of fluorine, chlorine, OH, CN, methyl, difluoromethyl, trifluoromethyl, methoxy, 2-methoxyethyl, $C(O)NH_2$, $C(O)OCH_3$ and $NH_2$, or, if $Cyc^3$ is phenyl, two radicals $R^{C3}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

$R^{C4}$ is selected from fluorine, chlorine, CN, methyl, difluoromethyl, trifluoromethyl, methoxy, OH and $NH_2$.

$R^a$ is $C_1$-$C_4$-alkyl or fluorinated $C_1$-$C_2$-alkyl, in particular methyl or trifluoromethyl;

$R^b$ is hydrogen, $C_1$-$C_4$-alkyl or fluorinated $C_1$-$C_2$-alkyl, $R^c$ and $R^d$ are independently of each other selected from hydrogen, and $C_1$-$C_2$-alkyl;

$R^e$ and $R^f$ are independently of each other selected from hydrogen, $C_1$-$C_2$-alkyl;

$R^g$ is hydrogen or $C_1$-$C_4$-alkyl, in particular hydrogen or methyl, $R^h$ is $C_1$-$C_4$-alkyl or fluorinated $C_1$-$C_2$-alkyl, in particular methyl or trifluoromethyl;

$R^y$, $R^{y'}$ are indepentyl hydrogen or methyl;

Z is a bond, $CH_2$ or $CH_2CH_2$.

Particular embodiment of the invention relates to the compounds of formula I, to the N-oxides, the prodrugs, the hydrates and the tautomers thereof and to the pharmaceutically suitable salts thereof, where the compounds of the formula I are selected from the group consisting of:

5-methyl-3-(oxetan-3-ylamino)-7-(pyridin-4-yl)thieno[2,3-d]pyridazin-4(5H)-one;

5-methyl-3-(morpholin-4-yl)-7-(pyridin-4-yl)thieno[2,3-d]pyridazin-4(5H)-one;

3-(4-hydroxypiperidin-1-yl)-5-methyl-7-(pyridin-4-yl)thieno[2,3-d]pyridazin-4(5H)-one;

tert-butyl 4-[5-methyl-4-oxo-7-(pyridin-4-yl)-4,5-dihydrothieno[2,3-d]pyridazin-3-yl]piperazine-1-carboxylate;

5-methyl-7-(pyridin-4-yl)-3-(pyrimidin-5-yl)thieno[2,3-d]pyridazin-4(5H)-one;

5-methyl-3-(pyridazin-4-yl)-7-(pyridin-4-yl)thieno[2,3-d]pyridazin-4(5H)-one;

3-(4-fluorophenyl)-5-methyl-7-(pyridin-4-yl)thieno[2,3-d]pyridazin-4(5H)-one;

3-[5-methyl-4-oxo-7-(pyridin-4-yl)-4,5-dihydrothieno[2,3-d]pyridazin-3-yl]benzonitrile;

3-(2-methoxypyrimidin-5-yl)-5-methyl-7-(pyridin-4-yl)thieno[2,3-d]pyridazin-4(5H)-one;

5-methyl-3-(piperazin-1-yl)-7-(pyridin-4-yl)thieno[2,3-d]pyridazin-4(5H)-one;

5-methyl-3-(morpholin-4-ylmethyl)-7-(pyridin-4-yl)thieno[2,3-d]pyridazin-4(5H)-one;

5-methyl-3-(pyridin-3-yl)-7-(pyridin-4-yl)thieno[2,3-d]pyridazin-4(5H)-one;

3-(1H-indol-5-yl)-5-methyl-7-(pyridin-4-yl)thieno[2,3-d]pyridazin-4(5H)-one;

5-methyl-3-[(E)-2-phenylethenyl]-7-(pyridin-4-yl)thieno[2,3-d]pyridazin-4(5H)-one;

5-methyl-7-(pyridin-4-yl)-3-(pyridin-3-ylethynyl)thieno[2,3-d]pyridazin-4(5H)-one;

N-benzyl-5-methyl-4-oxo-7-(pyridin-4-yl)-4,5-dihydrothieno[2,3-d]pyridazine-3-carboxamide;

5-methyl-3-[(4-methylpiperazin-1-yl)carbonyl]-7-(pyridin-4-yl)thieno[2,3-d]pyridazin-4(5H)-one;

N-benzyl-N-ethyl-5-methyl-4-oxo-7-(pyridin-4-yl)-4,5-dihydrothieno[2,3-d]pyridazine-3-carboxamide;

3-(4-methoxyphenyl)-5-methyl-7-(pyridin-4-yl)thieno[2,3-d]pyridazin-4(5H)-one;

3-(1-benzothiophen-2-yl)-5-methyl-7-(pyridin-4-yl)thieno[2,3-d]pyridazin-4(5H)-one;

5-methyl-3-[3-(1H-pyrazol-1-yl)phenyl]-7-(pyridin-4-yl)thieno[2,3-d]pyridazin-4(5H)-one;

4-[5-methyl-4-oxo-7-(pyridin-4-yl)-4,5-dihydrothieno[2,3-d]pyridazin-3-yl]benzonitrile;

3-(1-benzothiophen-3-yl)-5-methyl-7-(pyridin-4-yl)thieno[2,3-d]pyridazin-4(5H)-one;

3-(6-fluoropyridin-3-yl)-5-methyl-7-(pyridin-4-yl)thieno[2,3-d]pyridazin-4(5H)-one;

3-(4-hydroxyphenyl)-5-methyl-7-(pyridin-4-yl)thieno[2,3-d]pyridazin-4(5H)-one;

3-[5-methyl-4-oxo-7-(pyridin-4-yl)-4,5-dihydrothieno[2,3-d]pyridazin-3-yl]benzonitrile;

3-(3-methoxyphenyl)-5-methyl-7-(pyridin-4-yl)thieno[2,3-d]pyridazin-4(5H)-one;
3-(3-fluorophenyl)-5-methyl-7-(pyridin-4-yl)thieno[2,3-d]pyridazin-4(5H)-one;
5-methyl-3-[3-(morpholin-4-ylcarbonyl)phenyl]-7-(pyridin-4-yl)thieno[2,3-d]pyridazin-4(5H)-one;
N-{4-[5-methyl-4-oxo-7-(pyridin-4-yl)-4,5-dihydrothieno[2,3-d]pyridazin-3-yl]phenyl}methanesulfonamide;
5-methyl-7-(pyridin-4-yl)-3-(thiophen-3-yl)thieno[2,3-d]pyridazin-4(5H)-one;
3-(2,3-dihydro-1-benzofuran-5-yl)-5-methyl-7-(pyridin-4-yl)thieno[2,3-d]pyridazin-4(5H)-one;
3-(2-fluorophenyl)-5-methyl-7-(pyridin-4-yl)thieno[2,3-d]pyridazin-4(5H)-one;
5-methyl-3-(1-methyl-1H-pyrazol-4-yl)-7-(pyridin-4-yl)thieno[2,3-d]pyridazin-4(5H)-one;
3-[4-(dimethylamino)phenyl]-5-methyl-7-(pyridin-4-yl)thieno[2,3-d]pyridazin-4(5H)-one;
3-(2-methoxyphenyl)-5-methyl-7-(pyridin-4-yl)thieno[2,3-d]pyridazin-4(5H)-one;
N-cyclopropyl-4-[5-methyl-4-oxo-7-(pyridin-4-yl)-4,5-dihydrothieno[2,3-d]pyridazin-3-yl]benzamide;
3-(1-benzyl-1H-pyrazol-4-yl)-5-methyl-7-(pyridin-4-yl)thieno[2,3-d]pyridazin-4(5H)-one;
5-methyl-3-{3-[(4-methylpiperazin-1-yl)methyl]phenyl}-7-(pyridin-4-yl)thieno[2,3-d]pyridazin-4(5H)-one;
5-methyl-3-{4-[(4-methylpiperazin-1-yl)methyl]phenyl}-7-(pyridin-4-yl)thieno[2,3-d]pyridazin-4(5H)-one;
3-(2-hydroxyphenyl)-5-methyl-7-(pyridin-4-yl)thieno[2,3-d]pyridazin-4(5H)-one;
5-methyl-3-(4-methylphenyl)-7-(pyridin-4-yl)thieno[2,3-d]pyridazin-4(5H)-one;
3-(1,3-benzodioxol-5-yl)-5-methyl-7-(pyridin-4-yl)thieno[2,3-d]pyridazin-4(5H)-one;
5-methyl-7-(piperidin-1-yl)-3-(pyridin-4-yl)thieno[2,3-d]pyridazin-4(5H)-one;
3-(4-fluorophenyl)-5-methyl-7-(pyridin-4-yl)thieno[2,3-d]pyridazin-4(5H)-one;
5-methyl-7-(4-methylpiperazin-1-yl)-3-(pyridin-4-yl)thieno[2,3-d]pyridazin-4(5H)-one;
7-(benzylamino)-5-methyl-3-(pyridin-4-yl)thieno[2,3-d]pyridazin-4(5H)-one;
7-(furan-2-ylmethoxy)-5-methyl-3-(pyridin-4-yl)thieno[2,3-d]pyridazin-4(5H)-one;
7-(cyclohexyloxy)-5-methyl-3-(pyridin-4-yl)thieno[2,3-d]pyridazin-4(5H)-one;
7-(benzyloxy)-5-methyl-3-(pyridin-4-yl)thieno[2,3-d]pyridazin-4(5H)-one;
5-methyl-3-(pyridin-4-yl)-7-(pyridin-2-ylmethoxy)thieno[2,3-d]pyridazin-4(5H)-one;
5-methyl-7-[(1-methyl-1H-imidazol-2-yl)methoxy]-3-(pyridin-4-yl)thieno[2,3-d]pyridazin-4(5H)-one;
7-(cyclohexylmethoxy)-5-methyl-3-(pyridin-4-yl)thieno[2,3-d]pyridazin-4(5H)-one;
5-methyl-3-(pyridin-4-yl)-7-(1,3-thiazol-2-ylmethoxy)thieno[2,3-d]pyridazin-4(5H)-one;
3-({[5-methyl-4-oxo-3-(pyridin-4-yl)-4,5-dihydrothieno[2,3-d]pyridazin-7-yl]oxy}methyl)benzonitrile;
7-(2,3-dihydro-1H-inden-2-yloxy)-5-methyl-3-(pyridin-4-yl)thieno[2,3-d]pyridazin-4(5H)-one;
7-[(3-methoxybenzyl)oxy]-5-methyl-3-(pyridin-4-yl)thieno[2,3-d]pyridazin-4(5H)-one;
7-[(4-chlorobenzyl)oxy]-5-methyl-3-(pyridin-4-yl)thieno[2,3-d]pyridazin-4(5H)-one;
7-(1-benzofuran-3-ylmethoxy)-5-methyl-3-(pyridin-4-yl)thieno[2,3-d]pyridazin-4(5H)-one;
7-(1-benzofuran-7-ylmethoxy)-5-methyl-3-(pyridin-4-yl)thieno[2,3-d]pyridazin-4(5H)-one;
5-methyl-7-{[3-(propan-2-yl)benzyl]oxy}-3-(pyridin-4-yl)thieno[2,3-d]pyridazin-4(5H)-one;
7-[(4,4-difluorocyclohexyl)methoxy]-5-methyl-3-(pyridin-4-yl)thieno[2,3-d]pyridazin-4(5H)-one;
3-({[5-methyl-4-oxo-3-(pyridin-4-yl)-4,5-dihydrothieno[2,3-d]pyridazin-7-yl]oxy}methyl)benzamide;
3-({[5-methyl-4-oxo-3-(pyridin-4-yl)-4,5-dihydrothieno[2,3-d]pyridazin-7-yl]oxy}methyl)benzamide;
7-(1,3-benzodioxol-5-ylmethoxy)-5-methyl-3-(pyridin-4-yl)thieno[2,3-d]pyridazin-4(5H)-one;
5-methyl-7-[(1-methyl-1H-benzimidazol-2-yl)methoxy]-3-(pyridin-4-yl)thieno[2,3-d]pyridazin-4(5H)-one;
7-(1,3-benzothiazol-2-ylmethoxy)-5-methyl-3-(pyridin-4-yl)thieno[2,3-d]pyridazin-4(5H)-one;
methyl 3-({[5-methyl-4-oxo-3-(pyridin-4-yl)-4,5-dihydrothieno[2,3-d]pyridazin-7-yl]oxy}methyl)benzoate;
5-methyl-7-{[3-(propan-2-yloxy)benzyl]oxy}-3-(pyridin-4-yl)thieno[2,3-d]pyridazin-4(5H)-one;
N-(2-hydroxyphenyl)-2-{[5-methyl-4-oxo-3-(pyridin-4-yl)-4,5-dihydrothieno[2,3-d]pyridazin-7-yl]oxy}acetamide;
7-[(3,5-dimethoxybenzyl)oxy]-5-methyl-3-(pyridin-4-yl)thieno[2,3-d]pyridazin-4(5H)-one;
7-{[3-(difluoromethoxy)benzyl]oxy}-5-methyl-3-(pyridin-4-yl)thieno[2,3-d]pyridazin-4(5H)-one;
7-[(3,4-dichlorobenzyl)oxy]-5-methyl-3-(pyridin-4-yl)thieno[2,3-d]pyridazin-4(5H)-one;
5-methyl-7-[1-(1-methyl-1H-benzimidazol-2-yl)ethoxy]-3-(pyridin-4-yl)thieno[2,3-d]pyridazin-4(5H)-one;
tert-butyl 4-({[5-methyl-4-oxo-3-(pyridin-4-yl)-4,5-dihydrothieno[2,3-d]pyridazin-7-yl]oxy}methyl)piperidine-1-carboxylate;
tert-butyl 5-({[5-methyl-4-oxo-3-(pyridin-4-yl)-4,5-dihydrothieno[2,3-d]pyridazin-7-yl]oxy}methyl)-1,3-dihydro-2H-isoindole-2-carboxylate;
5-methyl-7-phenoxy-3-(pyridin-4-yl)thieno[2,3-d]pyridazin-4(5H)-one;
5-methyl-3-(pyridin-4-yl)-7-(pyridin-3-yloxy)thieno[2,3-d]pyridazin-4(5H)-one;
2-{[5-methyl-4-oxo-3-(pyridin-4-yl)-4,5-dihydrothieno[2,3-d]pyridazin-7-yl]oxy}benzonitrile;
7-(2-methoxyphenoxy)-5-methyl-3-(pyridin-4-yl)thieno[2,3-d]pyridazin-4(5H)-one;
7-(3-methoxyphenoxy)-5-methyl-3-(pyridin-4-yl)thieno[2,3-d]pyridazin-4(5H)-one;
7-(4-methoxyphenoxy)-5-methyl-3-(pyridin-4-yl)thieno[2,3-d]pyridazin-4(5H)-one;
7-(3-hydroxy-5-methoxypyridin-2-yl)-5-methyl-3-(pyridin-4-yl)thieno[2,3-d]pyridazin-4(5H)-one;
7-[(5-methoxypyridin-3-yl)oxy]-5-methyl-3-(pyridin-4-yl)thieno[2,3-d]pyridazin-4(5H)-one;
7-(1,3-benzodioxol-5-yloxy)-5-methyl-3-(pyridin-4-yl)thieno[2,3-d]pyridazin-4(5H)-one;
7-[(2-chloro-5-methylpyridin-3-yl)oxy]-5-methyl-3-(pyridin-4-yl)thieno[2,3-d]pyridazin-4(5H)-one;
7-(3,4-dimethoxyphenoxy)-5-methyl-3-(pyridin-4-yl)thieno[2,3-d]pyridazin-4(5H)-one;
7-(3,5-dimethoxyphenoxy)-5-methyl-3-(pyridin-4-yl)thieno[2,3-d]pyridazin-4(5H)-one;
7-{[6-(benzyloxy)pyridin-3-yl]oxy}-5-methyl-3-(pyridin-4-yl)thieno[2,3-d]pyridazin-4(5H)-one;
3-[5-methyl-4-oxo-3-(pyridin-4-yl)-4,5-dihydrothieno[2,3-d]pyridazin-7-yl]benzonitrile;
4-[5-methyl-4-oxo-3-(pyridin-4-yl)-4,5-dihydrothieno[2,3-d]pyridazin-7-yl]benzonitrile;

7-(4-methoxyphenyl)-5-methyl-3-(pyridin-4-yl)thieno[2,3-d]pyridazin-4(5H)-one;
7-(1,3-benzoxazol-6-yl)-5-methyl-3-(pyridin-4-yl)thieno[2,3-d]pyridazin-4(5H)-one;
2-[5-methyl-4-oxo-3-(pyridin-4-yl)-4,5-dihydrothieno[2,3-d]pyridazin-7-yl]benzamide;
7-[1-(2-methoxyethyl)-1H-pyrazol-4-yl]-5-methyl-3-(pyridin-4-yl)thieno[2,3-d]pyridazin-4(5H)-one;
5-methyl-3-(pyridin-4-yl)-7-[1-(2,2,2-trifluoroethyl)-1H-pyrazol-4-yl]thieno[2,3-d]pyridazin-4(5H)-one;
5-methyl-3-(pyridin-4-yl)-7-[4-(trifluoromethoxy)phenyl]thieno[2,3-d]pyridazin-4(5H)-one;
7-(3,4-dimethoxyphenyl)-5-methyl-3-(pyridin-4-yl)thieno[2,3-d]pyridazin-4(5H)-one;
7-(4-fluorophenyl)-5-methyl-3-(pyridin-4-yl)thieno[2,3-d]pyridazin-4(5H)-one;
7-(2-fluoropyridin-4-yl)-5-methyl-3-(pyridin-4-yl)thieno[2,3-d]pyridazin-4(5H)-one;
7-(3-chlorophenyl)-5-methyl-3-(pyridin-4-yl)thieno[2,3-d]pyridazin-4(5H)-one;
7-(biphenyl-4-yl)-5-methyl-3-(pyridin-4-yl)thieno[2,3-d]pyridazin-4(5H)-one;
7-(3-hydroxyphenyl)-5-methyl-3-(pyridin-4-yl)thieno[2,3-d]pyridazin-4(5H)-one;
5-methyl-7-(4-phenoxyphenyl)-3-(pyridin-4-yl)thieno[2,3-d]pyridazin-4(5H)-one;
7-(2,4-dichlorophenyl)-5-methyl-3-(pyridin-4-yl)thieno[2,3-d]pyridazin-4(5H)-one;
7-(4-chlorophenyl)-5-methyl-3-(pyridin-4-yl)thieno[2,3-d]pyridazin-4(5H)-one;
7-(3,5-dimethoxyphenyl)-5-methyl-3-(pyridin-4-yl)thieno[2,3-d]pyridazin-4(5H)-one;
5-methyl-3-(pyridin-4-yl)-7-[3-(trifluoromethoxy)phenyl]thieno[2,3-d]pyridazin-4(5H)-one;
7-(2-methoxyphenyl)-5-methyl-3-(pyridin-4-yl)thieno[2,3-d]pyridazin-4(5H)-one;
5-methyl-3-(pyridin-4-yl)-7-[3-(trifluoromethyl)phenyl]thieno[2,3-d]pyridazin-4(5H)-one;
7-(2-fluorophenyl)-5-methyl-3-(pyridin-4-yl)thieno[2,3-d]pyridazin-4(5H)-one;
7-(3-fluorophenyl)-5-methyl-3-(pyridin-4-yl)thieno[2,3-d]pyridazin-4(5H)-one;
5-methyl-3-(pyridin-4-yl)-7-[4-(trifluoromethyl)phenyl]thieno[2,3-d]pyridazin-4(5H)-one;
7-(4-hydroxyphenyl)-5-methyl-3-(pyridin-4-yl)thieno[2,3-d]pyridazin-4(5H)-one;
7-[3-(dimethylamino)phenyl]-5-methyl-3-(pyridin-4-yl)thieno[2,3-d]pyridazin-4(5H)-one;
5-methyl-7-(2-methylpyridin-4-yl)-3-(pyridin-4-yl)thieno[2,3-d]pyridazin-4(5H)-one;
5-methyl-7-(4-methylphenyl)-3-(pyridin-4-yl)thieno[2,3-d]pyridazin-4(5H)-one;
5-methyl-3-(pyridin-4-yl)-7-[4-(trifluoromethoxy)phenyl]thieno[2,3-d]pyridazin-4(5H)-one;
7-(3-methoxyphenyl)-5-methyl-3-(pyridin-4-yl)thieno[2,3-d]pyridazin-4(5H)-one;
7-(1,3-benzodioxol-5-yl)-5-methyl-3-(pyridin-4-yl)thieno[2,3-d]pyridazin-4(5H)-one;
5-methyl-7-(piperidin-4-ylmethoxy)-3-(pyridin-4-yl)thieno[2,3-d]pyridazin-4(5H)-one;
7-(2,3-dihydro-1H-isoindol-5-ylmethoxy)-5-methyl-3-(pyridin-4-yl)thieno[2,3-d]pyridazin-4(5H)-one;
3-[4-oxo-7-(pyridin-4-yl)-5-(2,2,2-trifluoroethyl)-4,5-dihydrothieno[2,3-d]pyridazin-3-yl]benzonitrile;
3-(2-methylpyrimidin-5-yl)-7-(pyridin-4-yl)-5-(2,2,2-trifluoroethyl)thieno[2,3-d]pyridazin-4(5H)-one;
3-[4-oxo-7-(pyridin-4-yl)-5-(2,2,2-trifluoroethyl)-4,5-dihydrothieno[2,3-d]pyridazin-3-yl]benzonitrile;
5-methyl-3,7-di(pyridin-4-yl)thieno[2,3-d]pyridazin-4(5H)-one;
3,7-di(pyridin-4-yl)-5-(2,2,2-trifluoroethyl)thieno[2,3-d]pyridazin-4(5H)-one;
5-tert-butyl-3,7-di(pyridin-4-yl)thieno[2,3-d]pyridazin-4(5H)-one;
5-cyclohexyl-3,7-di(pyridin-4-yl)thieno[2,3-d]pyridazin-4(5H)-one;
5-cyclopentyl-3,7-di(pyridin-4-yl)thieno[2,3-d]pyridazin-4(5H)-one;
5-(propan-2-yl)-3,7-di(pyridin-4-yl)thieno[2,3-d]pyridazin-4(5H)-one;
5-ethyl-3,7-di(pyridin-4-yl)thieno[2,3-d]pyridazin-4(5H)-one;
5-(2-methylpropyl)-3,7-di(pyridin-4-yl)thieno[2,3-d]pyridazin-4(5H)-one;
5-(2-methoxyethyl)-3,7-di(pyridin-4-yl)thieno[2,3-d]pyridazin-4(5H)-one;
5-propyl-3,7-di(pyridin-4-yl)thieno[2,3-d]pyridazin-4(5H)-one;
3-[4-oxo-3,7-di(pyridin-4-yl)thieno[2,3-d]pyridazin-5(4H)-yl]propanenitrile;
3,7-di(pyridin-4-yl)-5-(tetrahydrofuran-2-ylmethyl)thieno[2,3-d]pyridazin-4(5H)-one;
3,7-di(pyridin-4-yl)-5-[2-(pyrrolidin-1-yl)ethyl]thieno[2,3-d]pyridazin-4(5H)-one;
5-[2-(dimethylamino)ethyl]-3,7-di(pyridin-4-yl)thieno[2,3-d]pyridazin-4(5H)-one;
5-[2-(morpholin-4-yl)ethyl]-3,7-di(pyridin-4-yl)thieno[2,3-d]pyridazin-4(5H)-one;
5-ethyl-7-(pyridin-4-yl)-3-(pyrimidin-5-yl)thieno[2,3-d]pyridazin-4(5H)-one;
5-(cyclopropylmethyl)-7-(pyridin-4-yl)-3-(pyrimidin-5-yl)thieno[2,3-d]pyridazin-4(5H)-one; and
5-methyl-3-(pyridin-4-yl)-7-(pyridin-3-ylmethoxy)thieno[2,3-d]pyridazin-4(5H)-one.

The compounds of the invention of the general formula I and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", $5^{th}$ edition, Wiley & Sons and the literature cited therein, and R. Larock, "Comprehensive Organic Transformations", $2^{nd}$ edition, Weinheim, 1999 and the literature cited therein. The compounds of the invention of the general formula I are advantageously prepared by the methods described below and/or in the experimental section.

Compounds of the formula I, wherein Q is oxygen, can be prepared e.g. by reacting a compound of the formula IIa or IIb

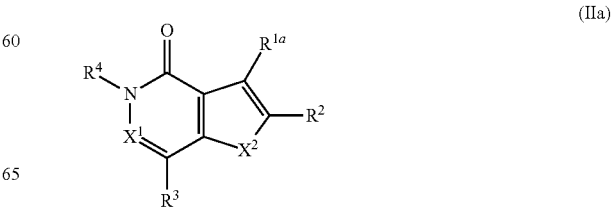

(IIa)

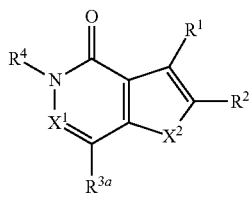

(IIb)

wherein
$X^1, X^2, R^2, R^3$ and $R^4$ are as defined for formulae I, I.A, I.B, I.C and I.D;
$R^{1a}, R^{3a}$ independently of each other, are selected from the group consisting of chlorine, bromine or iodine;
with a compound of formula III, M-Y-Cyc  (III)

where Y has one of the meanings given for $Y^1$ and $Y^3$ and where Y is in particular
$CH_2$, 1,2-ethandiyl, 1,2-ethenediyl or 1,2-ethynediyl or especially a bond, and
Cyc has one of the meanings given herein for $Cyc^1$ and $Cyc^3$ and wherein
M is a Li, $B(OR^{B1})(OR^{B2})$ radical or a $Sn(R^{Sn})_3$ radical, where $R^{B1}$ and $R^{B2}$ are, independently of each other, hydrogen or $C_1$-$C_4$-alkyl or $R^{B1}$ and $R^{B2}$ together form a $C_2$-$C_6$-alkanediyl moietyl, e.g. ethane-1,2-diyl, propane-1,3-diyl or 1,1,2,2-tetramethylethane-1,2-diyl, and wherein $R^{Sn}$ is $C_1$-$C_6$-alkyl or $C_3$-$C_6$-cycloalkyl or phenyl.

Amongst the compounds of formula III, where Y is a chemical bond, particular preference is given to the compounds of formula Ma and, if $R^{B1}$ and $R^{B2}$ are hydrogen, the trimers thereof.

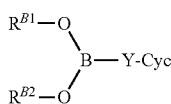

(IIIa)

The reaction of the compounds IIa or IIb with the compound III can be performed by analogy to known coupling reactions in the presence of suitable transition metal catalysts, in particular palladium catalysts. Typical reactions conditions are those of Stille coupling (see e.g. Stille et al. Angew. Chem. Int. Ed. Engl. 1986, 25,508; J. Eluguero et al.; Synthesis 1997, 5, 563-566) or Suzuki coupling (see e.g. A. Suzuki et al, Chem. Rev. 1995, 95, 2457-2483, N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253).

In a similar manner, compounds of the formula I, where $Y^1$ or $Y^3$ is NH or O or were $Cyc^1$-$Y^1$ or $Cyc^3$-$Y^3$ ($Y^1$ and $Y^3$ are single bonds) are an N-bound heterocycle can be prepared by reacting a compound of the formula IIa and IIb, as defined above, with a compound of the formula III'

H—Y-Cyc  (III')

where Y and Cyc are as defined for formula III. The reaction of IIa or IIb with III' is preferably carried out in an aprotic solvent, such as dimethylsulfoxide, acetonitrile, N-methylpyrrolidone, dimethylformamide, dimethylacetamide, tetramethyl urea, or mixtures thereof or mixtures thereof with halogenated hydrocarbons such as dichloromethane. The reaction is preferably carried out in the presence of a suitable base, e.g. an alkalimetal carbonate such as lithium carbonate, sodium carbonate, potassium carbonate or caesium carbonate or an alkalimetal alkoxide.

Compounds of the formula I, where Q is O, can also be prepared e.g. by reacting a compound of the formula IIc or IId

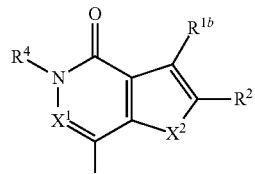

(IIc)

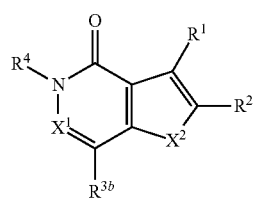

(IId)

wherein
$X^1, X^2, R^2, R^3$ and $R^4$ are as defined for formulae I, I.A, I.B, I.C and I.D;
$R^{1b}, R^{3b}$ independently of each other, are a radical M as defined for formula III and in particular Li, MgHal' or ZnHal' or a $B(OR^{B1})(OR^{B2})$ radical;
with a compound of formula IIIb or IIIc, Hal-Y-Cyc  (IIIb)

H—Y-Cyc  (IIIc)

where Y and Cyc are as defined herein and where Y in formula Mb is in particular a single bond, $CH_2$, 1,2-ethanediyl, ethenediyl and where Y in formula IIIc is in particular a single bond or ethynediyl, and wherein Hal is bromine or iodine. Hal' is halogen, in particular chlorine, bromine or iodine.

The reaction of the compound IIc or IId with the compound IIIb or IIIc can be performed by analogy tot the reaction of compound IIa or IIb with compound III.

The compounds II, IIa, IIb, IIc, IId, III, III', IIIa and IIIb are known or can be prepared by standard methods of organic chemistry.

Compounds of the formula I, where $Y^1$-$Cyc^1$ or $Y^3$-$Cyc^3$ is a N-bound radical can be obtained by a coupling reaction between the compound IIa or IIb and the corresponding amine in the presence of a palladium catalyst in terms of a Buchwald-Hartwig reaction. Suitable palladium catalyst are for example tris-(dibenzylidene-acetone)dipalladium(0) ($Pd_2(dba)_3$), [1,1-bis(diphenylphosphino)ferrocene]dichloro-palladium(II) ($PdCl_2(dppf)$) or palladium acetate ($Pd(OAc)_2$). The reaction is usually carried out in the presence of a tri (substituted)phosphine, e.g. a triarylphosphine such as triphenylphosphine, tritolylphosphine or 2,2'-bis(diphenylphosphino)-1,1'-binaphthalene (BINAP), tri(cyclo)alkylphosphine such as tris-n-butylphosphine, tris(tert-butyl)phosphine or tris(cyclohexylphosphine), or dicyclohexyl-(2', 4',6'-tri-iso-propyl-biphenyl-2-yl)-phosphane (X-Phos). Usually, the reaction is performed in the presence of a base such as an alkaline alkoxide, earth alkine alkoxide, alkaline carbonate or earth alkaline carbonate such as or sodium tert-butoxide or cesium carbonate.

Compounds of the formula I (or likewise the compounds IIa and IIb), where Q is O and $R^4$ is different form hydrogen can be prepared by reacting compounds of the formulae I with $R^4$=hydrogen with a compound of the formula $R^4$-L where L is a suitable leaving group, such as halogen, e.g. chlorine, bromine or iodine, methansulfonate, tosylate etc. or with an alcohol of the formula $R^4$—OH in terms of a Mitsunobu reaction.

Hal is halogen, preferably bromine or iodine. The reaction is usually performed in the presence of a base. Suitable bases are alkali metal carbonates and hydrogen carbonates or earth metal carbonates and hydrogencarbonates such as cesium carbonate.

Apart from that, compounds of the formula I, where Q is S can be prepared by successively reacting compounds of the formula I, where Q is O with a suitable sulfurizing agent, such as Lawenson's reagent or $P_2S_5$.

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

Compounds of the formulae IIc and IId can be prepared from compounds of the formulae IIa and IIb by suitable metal-halogen exchange reactions.

The compounds of the formulae III, III', IIIa and IIIb are well known in the art or can be prepared by anology to well established reactions of organic synthetic chemistry or by analogy to the methods as described in standard works of organic chemistry, e.g. Houben-Weyl, "Methoden der Organischen Chemie", Thieme-Verlag, Stuttgart, Jerry March "Advanced Organic Chemistry", $5^{th}$ edition, Wiley & Sons and the literature cited therein, and R. Larock, "Comprehensive Organic Transformations", $2^{nd}$ edition, Weinheim, 1999 and the literature cited therein.

The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from −10° C. to 100° C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

A particular embodiment of the invention relates to compounds selected from the group consisting of
3-bromo-5-methyl-7-(pyridin-4-yl)thieno[2,3-d]pyridazin-4 (5H)-one;
7-chloro-5-methyl-3-(pyridin-4-yl)thieno[2,3-d]pyridazin-4 (5H)-one;
3-bromo-7-(pyridin-4-yl)-5-(2,2,2-trifluoroethyl)-thieno[2, 3-d]pyridazin-4(5H)-one;
7-hydroxy-5-methyl-3-(pyridin-4-yl)thieno[2,3-d]pyridazin-4(5H)-one; and
the N-oxides, the prodrugs, the tautomers and the hydrates thereof, and the pharmaceutically acceptable salts thereof.

Due to their capability of inhibiting PDE10A at low concentrations, the compounds of the formula I, their N-oxides, their hydrates, their tautomers and their prodrugs and the pharmaceutically acceptable salts thereof, are particularly suitable for treating disorders or conditions, which can be treated by inhibition of phosphodiesterase type 10A. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by inhibition of PDE10A, including curative treatment, control or amelioration and prophylaxis, include CNS disorders, in particular schizophrenia, depression, bipolar disorders, cognitive dysfunctions associated with schizophrenia, cognitive dysfunctions associated with Alzheimer's disease, Huntington's disease (Huntington chorea), anxiety and substance-related disorders, especially substance use disorder, substance tolerance conditions associated with substance withdrawal. Disorders or conditions which can be treated by inhibition of PDE10A, including curative treatment, control or amelioration and prophylaxis, also include treatment of diet induced obesity.

Thus, the invention relates to the use of compounds of formula I, their N-oxides, their hydrates, their tautomers and their prodrugs and the pharmaceutically acceptable salts thereof, for treatment of disorders or conditions, which can be treated by inhibition of phosphodiesterase type 10A, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by inhibition of phosphodiesterase type 10A, said method comprising administering an effective amount of at least one compound, selected from the group of compounds of formula I, their N-oxides, their hydrates, their tautomers, their prodrugs and the pharmaceutically acceptable salts thereof, to a mammal in need thereof.

The present invention in particular relates to:
a method for treating, controlling, ameliorating or reducing the risk of schizophrenia in a mammalian;
a method for treating, controlling, ameliorating or reducing the risk of cognitive disturbances associated with schizophrenia in a mammalian;
a method for treating, controlling, ameliorating or reducing the risk of depression in a mammalian;

a method for treating, controlling, ameliorating or reducing the risk of bipolar disorders in a mammalian;

a method for treating or ameliorating the symptoms associated with substance use disorders in a mammalian;

a method for treating or ameliorating the symptoms associated with diet-induced obesity in a mammalian;

a method for treating, controlling, ameliorating or reducing the risk of cognitive disturbances associated with Alzheimer's disease in a mammalian;

a method for treating, controlling, ameliorating or reducing the risk of behavioral symptoms in Alzheimer's disease;

a method for treating, controlling, ameliorating or reducing the risk of anxiety in a mammalian;

a method for treating, controlling, ameliorating or reducing the risk of Huntington's disease in a mammalian;

which methods comprising administering an effective amount of at least one compound, selected from the group of compounds of formula I, their N-oxides, their hydrates, their tautomers, their prodrugs and the pharmaceutically acceptable salts thereof, to a mammal in need thereof.

The subject treated in the present methods is generally a mammal, preferably a human being, male or female, in whom inhibition of PDE10A is desired. The terms "effective amount" and "therapeutically effective amount" mean the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating cognitive disturbances associated with schizophrenia, comprising:

administering to a patient in need thereof an effective amount of at least one compound, selected from the group of compounds of formula I, their N-oxides, their hydrates, their tautomers, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In the treatment, prevention, control, amelioration, or reduction of risk of conditions which require inhibition of PDE10A an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, in the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The present invention also relates to pharmaceutical compositions (i.e. medicaments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The compounds of the invention also include those compounds in which one or more atoms have been replaced by their stable, non-radioactive isotopes, for example, a hydrogen atom by deuterium.

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The following examples are intended for further illustration of the present invention.

Abbreviations which have been used in the descriptions of the schemes and the Examples that follow are: ACN for acetonitrile; BINAP for 2,2'-bis (diphenylphosphino)-1,1'-binaphthyl; CDI for 1,1'-carbonyldiimidazole; DCM for dichloromethane; DMF for dimethylformamide; EtOAc for ethyl acetate; EtOH for ethanol; Ex. for EXAMPLE; HATU for O-(7-azabenzotriazol-1-yl)-N,N,N',N'-tetramethyluronium hexafluorophosphate; HMPA for hexamethylphosphoramide; i-Pr for isopropyl; MeOH for methanol; $Pd_2(dba)_3$ for tris (dibenzylideneacetone)dipalladium(0); $PdCl_2$(dppf) for 1,1'-bis (diphenylphosphino)ferrocene-palladium (II)-dichloride; $PdCl_2$(dppf).$CH_2Cl_2$ for 1,1'-bis(diphenylphosphino)ferrocene-palladium (II)-dichloride dichloromethane adduct; Pd(PPh$_3$)$_4$ for tetrakis(triphenylphosphine)palladium(0); Pd$_2$(dba)$_3$.CHCl$_3$ for Tris(dibenzylideneacetone)dipalladium(0) chloroform adduct; PE for petroleum ether; R$_t$ for retention time; RT for room temperature; TEA for triethylamine; TFA for trifluoroacetic acid; THF for tetrahydrofuran.

LC-MS measurements were run on an Agilent 1200 HPLC/6100 SQ System. Generally, the following conditions were used:

Method A:
  Mobile Phase: A: Water (0.05% TFA) B: ACN (0.05% TFA);
  Gradient: 5% B for 0.1 min, increase to 95% B within 0.7 min, 95% B for 0.9 min, back to 5% B within 0.01 min;
  Flow Rate: 3.0 mL/min;
  Column: Zorbax SB-C18 Rapid Resolution HT, 4.6*30 mm, 1.8 um;
  Column Temperature: 45° C.

Method B:
  Mobile Phase: A: Water (10 mM NH$_4$HCO$_3$) B: CAN;
  Gradient: 5% B for 0.2 min, increase to 95% B within 1.2 min, 95% B for 1.6 min, back to 5% B within 0.01 min;
  Flow Rate: 1.8 mL/min;
  Column: XBridge C18, 4.6*50 mm, 3.5 um;
  Column Temperature: 50° C.

Method C:
  Mobile Phase: A: Water (10 mM NH$_4$HCO$_3$) B: CAN;
  Gradient: 5% for 0.2 min, increase to 95% B within 1.7 min, 95% B for 1.4 min, back to 5% B within 0.01 min;
  Flow Rate: 2.3 ml/min;
  Column: XBridge C18, 4.6*50 mm, 3.5 um;
  Column Temperature: 50° C.

Method D:
  Mobile Phase: A: Water (0.01% TFA) B: ACN (0.01% TFA);
  Gradient: 5% B for 0.2 min, increase to 95% B within 1.7 min, 95% B for 1.3 min, back to 5% B within 0.01 min;
  Flow Rate: 2.3 ml/min;
  Column: XBridge C18, 4.6*50 mm, 3.5 um;
  Column Temperature: 50° C.

The compounds I of the invention were purified in some cases by preparative HPLC. The compounds I then result as the TFA salts.

All mass spectra were taken using electrospray ionisation methods (ESI+).

$^1$H NMR spectra were recorded on a Bruker AVIII 400 or Bruker AVIII 500 spectrometer. Chemical shifts are expressed in parts of million (ppm, δ units). Coupling constants (J) are in units of hertz (Hz). Splitting patterns describe apparent multiplicities and are designated as s (singlet), d (doublet), t (triplet), q (quadruplet), m (multiplet).

The starting materials used in the examples are either commercially available or can be synthesized by the average skilled person trained in organic chemistry following routine laboratory practice as outlined, for example in the examples below.

PREPARATION EXAMPLES

I. Preparation of Core Building Blocks and Intermediates

I.1 3-bromo-5-methyl-7-(pyridin-4-yl)thieno[2,3-d]pyridazin-4(5H)-one

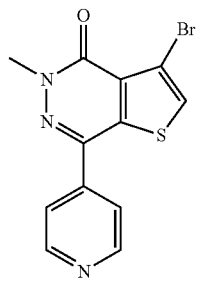 [SMILES: Cn1nc(-c2ccncc2)c2scc(Br)c2c1=O]

I.1.1 4-Bromothiophene-3-carboxylic acid

To a mixture of Mg (1.4 g, 60 mmol) and I$_2$(0.1 g) in anhydrous THF (2 mL) was added dropwise a solution of 2-bromo-propane (7.4 g, 60 mmol) in anhydrous THF (60 mL) at room temperature under nitrogen during a period of 30 min. After the addition, the mixture was refluxed until the most of magnesium was consumed. The resulting Grignard reagent was added dropwise to a solution of 3,4-dibromo-thiophene (12.1 g, 50 mmol) in anhydrous THF (60 mL) at 0° C. under nitrogen within about 30 min. The mixture was allowed to stir at 0° C. for 1.5 h. Then an excess CO$_2$ was purged into the mixture at −30° C. and the reaction mixture was stirred until the temperature rose to room temperature. The reaction was quenched with water (30 mL) and basified with 8% aq. NaOH solution to pH 11 and was washed with ethyl acetate (3×60 mL). The aqueous layer was acidified with 5% aq. HCl to pH 1~2, the precipitate was filtered and was dried to give the desired compound as off-white solid (5.2 g, 50% yield). LC-MS (Method A): m/z 209 (M+H)$^+$, R$_t$: 0.69 min.

I.1.2 N-methoxy-N-methyl-4-pyridinecarboxamide

To a suspension of 4-pyridinecarboxylic acid (12.3 g, 100 mmol) over CH$_2$Cl$_2$ (200 mL) a solution of CDI (18.0 g, 111 mmol) in CH$_2$Cl$_2$ (200 mL) was added. After addition, the mixture was stirred for 2 h at room temperature. Following this, N,O-dimethylhydroxyl-amine hydrochloride (13.9 g, 145 mmol) was added and the mixture was stirred overnight. The reaction mixture was quenched with 1N NaOH and the phases separated. The organic layer was dried over Na$_2$SO$_4$ and concentrated. The crude product was purified by column chromatography (PE/EtOAc=1:1) to give the title compound as orange oil (10.1 g, 61% yield). LC-MS (Method A): m/z 167 (M+H)$^+$, R$_t$: 0.49 min. $^1$H NMR (400 MHz, CDCl$_3$): δ=8.64 (d, J=6.0 Hz, 2H), 7.46 (d, J=6.0 Hz, 2H), 3.47 (s, 3H), 3.30 (s, 3H).

I.1.3
4-Bromo-2-isonicotinoylthiophene-3-carboxylic acid

To a solution of (i-Pr)$_2$NH (5.3 g, 53 mmol) in anhydrous THF (40 mL) at −78° C. was added n-BuLi (23.2 mL, 58 mmol, 2.5M in hexane) dropwise. The mixture was stirred at the same temperature for 0.5 h. Then a solution of 4-Bromothiophene-3-carboxylic acid (5.0 g, 24 mmol) and HMPA (0.86 g, 4.8 mmol) in anhydrous THF (50 mL) was slowly added. The mixture was stirred at the same temperature for 1 h and N-methoxy-N-methyl-4-pyridine carboxamide (8.0 g, 48 mmol) was added dropwise to the stirring mixture at −78° C. The reaction mixture was stirred for another hour at room temperature and was then quenched with H$_2$O. The aqueous layer was acidified with 5% aq. HCl to pH 1~2. The precipitate was removed by filtration and the resulting filtrate extraxted with CH$_2$Cl$_2$ (3×200 mL). The organic layers were dried over Na$_2$SO$_4$ and concentrated under reduced pressure. The crude product was washed with CH$_2$Cl$_2$ to give the title compound (1.6 g, 20% yield) as a yellow solid. LC-MS (Method A): m/z 312 (M+H)$^+$, R$_t$: 0.55 min. $^1$H NMR (400 MHz, DMSO-d6): δ=13.61 (s, 1H), 8.81-8.80 (m, 2H), 8.25 (s, 1H), 7.67-7.65 (m, 2H).

I.1.4 Ethyl 4-bromo-2-isonicotinoylthiophene-3-carboxylate

A mixture of ethyl iodide (3.78 mL, 48.06 mmol), Cs$_2$CO$_3$ (15.66 g, 48.06 mmol) and 4-bromo-2-isonicotinoylthiophene-3-carboxylic acid (5 g, 16.02 mmol) in CH$_3$CN (150 mL) was stirred at room temperature for about 12 h in a 250 mL round-bottomed flask. After completion of the reaction, the solvent was removed under reduced pressure. The reaction mixture was diluted with water and the aqueous layer was back extracted with ethyl acetate (3×100 mL). The combined organic layers were dried with Na$_2$SO$_4$, filtered and concentrated to afford a yellow solution. The resulting mixture was deposited onto silica gel, loaded onto a silica gel column and eluted with 5:1 PE/EtOAc to give the title compound (1.37 g, 25% yield). LC-MS (Method A): m/z 340 (M+H)$^+$, R$_t$: 1.07 min.

I.1.5 3-bromo-5-methyl-7-(pyridin-4-yl)thieno[2,3-d]pyridazin-4(5H)-one

A suspension of ethyl 4-bromo-2-isonicotinoylthiophene-3-carboxylate (5.2 g, 15.94 mmol) and methyl-hydrazine (2.2 g, 47.8 mmol) in EtOH (40 mL) was heated to reflux overnight. After removal of the solvent, the crude product was purified by silica gel column and eluted with 5:1 PE/EtOAc to give the title compound as a white solid (2.3 g, 44.8% yield). LC-MS (Method C): m/z 322 (M+H)$^+$, R$_t$: 1.75 min. $^1$H NMR (400 MHz, DMSO-d6): δ=8.80-8.78 (m, 2H), 8.28 (s, 1H), 7.81-7.80 (m, 1H), 3.81 (s, 3H).

I.2 7-chloro-5-methyl-3-(pyridin-4-yl)thieno[2,3-d]pyridazin-4(5H)-one

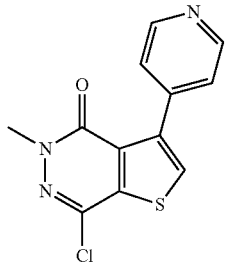 [SMILES: Cn1nc(Cl)c2scc(-c3ccncc3)c2c1=O]

I.2.1 4-Bromothiophene-3-carboxylic acid

The title compound was prepared according to example I.1.1. Yield: 6.2 g (60%). LC-MS (Method B): m/z 209 (M+H)$^+$, R$_t$: 0.672 min.

I.2.2 4-Bromothiophene-2,3-dicarboxylic acid

Diisopropylamine (17.92 mL, 128 mmol) was dissolved in THF (300 mL) and stirred at −30° C. while BuLi (8.91 g, 139 mmol) was added dropwise. The mixture was stirred at the same temperature for 0.5 h. Then the mixture was cooled to −78° C. and 4-bromothiophene-3-carboxylic acid (12 g, 58.0 mmol) and HMPA (2.02 mL, 11.6 mmol) dissolved in anhydrous THF (200 mL) were added slowly. The mixture was stirred at the same temperature for 1 h. Then the reaction mixture was purged with an excess of gaseous CO$_2$ at −40° C. The resulting solution was stirred at RT for about 15 min and then quenched with H$_2$O. 10% aq. NaOH was added. The aqueous layer was separated and washed with EtOAc. The aqueous layer was acidified with 10% aq. HCl to pH 1~2 and extracted with ethyl acetate (3×200 mL). The combined organic layers were washed with brine, dried over Na$_2$SO$_4$, filtered, and concentrated under reduced pressure to give the title compound (11 g, 43.8 mmol, 76% yield) as white solid, which was used in the next step (example 1.2.3) without further purification. LC-MS (Method A): m/z 273 (M+Na)$^+$, R$_t$: 0.58 min.

I.2.3 4-bromothiophene-2,3-dicarbonyl dichloride

A mixture of 4-bromothiophene-2,3-dicarboxylic acid (3.4 g, 13.54 mmol) and DMF (0.049 g, 0.677 mmol) in SOCl$_2$ (50 mL) was stirred at about 80° C. for about 1 h. The solvent was removed under reduced pressure to provide the title compound (3.6 g, 12.50 mmol, 92% yield) as a red oil (crude) which was used in the next step (example I.2.4) without further purification. LC-MS (Method A): m/z 279 (M+MeOH−Cl)$^+$, R$_t$: 0.82 min.

I.2.4 3-bromo-7-hydroxy-5-methyl-thieno[2,3-d]pyridazin-4(5H)-one and 3-bromo-4-hydroxy-6-methyl-thieno[2,3-d]pyridazin-7(5H)-one A mixture of triethylamine (105 mg, 1.042 mmol) and methylhydrazine (32.0 mg, 0.695 mmol) in CH$_2$Cl$_2$ (5 mL) was stirred at RT and 4-bromothiophene-2,3-dicarbonyl dichloride (100 mg, 0.347 mmol) was added. The resulting solution was stirred at about 25° C. for 45 min. Water was added and the resulting mixture extracted with CH$_2$Cl$_2$ (3×15 mL). The combined organic layers were washed with brine, dried over Na$_2$SO$_4$, filtered and concentrated under reduced pressure. The material was transferred in solution onto a silica gel column and eluted with CH$_2$Cl$_2$. Elution fractions containing the desired compounds were collected and the solvent was removed under reduced pressure to provide a mixture of the title compounds (40 mg, 0.153 mmol, 44.1% yield) as an off-white solid. LC-MS (Method A): m/z 261 (M+H)$^+$, R$_t$: 0.63 min.

I.2.5 7-hydroxy-5-methyl-3-(pyridin-4-yl)thieno[2,3-d]pyridazin-4(5)-one and 4-hydroxy-6-methyl-3-(pyridin-4-yl)thieno[2,3-d]pyridazin-7(5H)-one The mixture of 3-bromo-7-hydroxy-5-methyl-thieno[2,3-d]pyridazin-4(5H)-one and 3-bromo-4-hydroxy-6-methyl-thieno[2,3-d]pyridazin-7(5H)-one (100 mg, 0.383 mmol), PdCl$_2$(dppf) (30 mg, 0.041 mmol), pyridine-4-ylboronic acid (56.5 mg, 0.460 mmol) and K$_2$CO$_3$ (106 mg, 0.766 mmol) were disolved in 8 mL dioxane/H$_2$O (3:1) and stirred at 120° C. for about 5 h. Half the amount of solvent was removed under reduced pressure followed by the addition of water. The aqueous layer was extracted with ethyl acetate (3×25 mL). The combined organic layers were washed with brine, dried over Na$_2$SO$_4$, filtered, and concentrated under reduced pressure. The material was transferred in solution onto a silica gel column and eluted with 10% MeOH/CH$_2$Cl$_2$. Elution fractions containing the desired compounds were collected and the solvent was removed under reduced pressure to provide a mixture of the title compounds (60 mg, 0.231 mmol, 60.4% yield) as an off-white solid. LC-MS (Method A): m/z 260 (M+H)$^+$, R$_t$: 0.50 min. $^1$H NMR of 7-hydroxy-5-methyl-3-(4-pyridyl)thieno[2,3-d]pyridazin-4-one (400 MHz, CDCl$_3$): δ=8.69-7.68 (m, 2H), 7.67 (s, 1H), 7.49-7.48 (m, 2H), 3.82 (s, 1H).

I.2.6 7-chloro-5-methyl-3-(pyridin-4-yl)thieno[2,3-d]pyridazin-4(5H)-one

The mixture of 7-hydroxy-5-methyl-3-(pyridin-4-yl)thieno[2,3-d]pyridazin-4(5H)-one and 4-hydroxy-6-methyl-3-(pyridin-4-yl)thieno[2,3-d]pyridazin-7(5H)-one (2.0 g, 7.71 mmol) was dissolved in POCl$_3$ (15 mL) and stirred at 120° C. for about 18 h. Following this, most of the solvent was removed under reduced pressure. Water was added in caution until the POCl$_3$ was consumed. MeOH was added, basified with K$_2$CO$_3$. The suspension was filtered through a Büchner funnel. The filtrate was concentrated to dryness under reduced pressure. The resulting brown oil was purified by preparative HPLC to give the title compound as white solid. Preparative HPLC was performed using a 2767 PHW003 HPLC-system (Waters) equipped with a C18 preparative column (10 um 21*250 mm, Boston). Mobile Phase: A: water (10 mM NH$_4$HCO$_3$), B: CH$_3$CN; Gradient: 30-43% B in 8 min, stop at 14 min; Flow Rate: 30 mL/min; Detective Wavelength: 214\254 nm; R$_t$: 5.77 mM. LC-MS (Method B): m/z 278 (M+H)$^+$, R$_t$: 1.79 min. $^1$H NMR (400 MHz, CDCl$_3$): δ=8.69-7.68 (m, 2H), 7.67 (s, 1H), 7.49-7.48 (m, 2H), 3.82 (s, 1H).

I.3 3-bromo-7-(pyridin-4-yl)-5-(2,2,2-trifluoroethyl)thieno[2,3-d]pyridazin-4(5H)-one

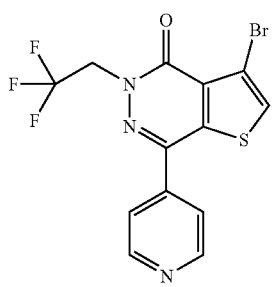 [SMILES: O=c1c2c(Br)csc2c(-c2ccncc2)nn1CC(F)(F)F]

I.3.1 4-Bromothiophene-3-carboxylic acid

The title compound was prepared according to example I.1.1. Yield: 15 g (88%). LC-MS (Method D): m/z 208 (M+H)$^+$, R$_t$: 1.38 min.

I.3.2 N-methoxy-N-methyl-4-pyridinecarboxamide

The title compound was prepared according to example I.1.2. Yield: 24 g (60%). LC-MS (Method C): m/z 167 (M+H)$^+$, R$_t$: 1.18 min.

I.3.3 4-Bromo-2-isonicotinoylthiophene-3-carboxylic acid

The title compound was prepared according to example I.1.3. Yield: 2.0 g (26%). LC-MS (Method A): m/z 313 (M+H)$^+$, R$_t$: 1.37 min.

I.3.4 Ethyl 4-bromo-2-isonicotinoylthiophene-3-carboxylate

The title compound was prepared according to example I.1.4. Yield: 2.5 g (44%). LC-MS (Method A): m/z 341 (M+H)$^+$, R$_t$: 1.67 min.

I.3.5 3-bromo-7-(pyridin-4-yl)-5H-thieno[2,3-d]pyridazin-4(5H)-one

A mixture of ethyl 4-bromo-2-isonicotinoylthiophene-3-carboxylate (5.0 g, 14.7 mmol) and NH$_2$NH$_2$.H$_2$O (3.7 g, 73.5 mmol) in EtOH (40 mL) was heated to 70° C. overnight in a sealed flask. The precipitate was filtered and the filter cake dried under reduced pressure to give the title compound (4.0 g, 88% yield) as white solid. LC-MS (Method C): m/z 309 (M+H)$^+$, R$_t$: 1.42 min.

I.3.6 3-bromo-7-(pyridin-4-yl)-5-(2,2,2-trifluoroethyl)thieno[2,3-d]pyridazin-4(5H)-one 3-bromo-7-(pyridin-4-yl)-5H-thieno[2,3-d]pyridazin-4(5H)-one (3.0 g, 9.74 mmol), K$_2$CO$_3$ (2.69 g, 19.47 mmol) and 1,1,1-trifluoro-2-iodoethane (4.09 g, 19.47 mmol) were each added sequentially to 50 mL of DMF. The mixture was heated to 65° C. for 12 h, 100 mL of water was added slowly and the resulting mixture extracted with EtOAc (3×100 mL). The combined organic phase was washed, dried, concentrated under reduced pressure and purified by silica gel column. The desired product was eluted with PE/EtOAc (3:1) to give the title compound as a white solid (1.5 g, 38% yield). LC-MS (Method A): m/z 391 (M+H)$^+$, R$_t$: 1.60 min. $^1$H NMR (400 MHz, CDCl$_3$): δ=8.82 (d, J=6.0, 2H), 7.73-7.74 (m, 2H), 7.71 (s, 1H), 4.92-4.98 (m, 2H).

I.4 Ethyl 2-(pyridine-4-carbonyl)-4-(pyridin-4-yl)thiophene-3-carboxylate

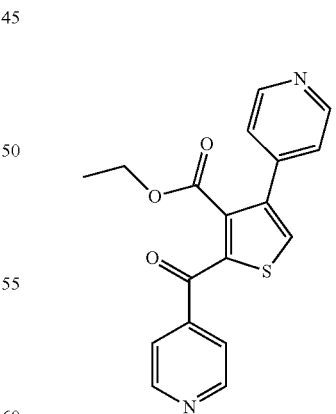

I.4.1 4-Bromothiophene-3-carboxylic acid

The title compound was prepared according to example I.1.1. Yield: 6.2 g (60%). LC-MS (Method A): m/z 207 (M+H)$^+$, R$_t$: 0.72 min.

I.4.2 N-methoxy-N-methyl-4-pyridinecarboxamide

The title compound was prepared according to example I.1.2. Yield: 14.3 g (85%). LC-MS (Method A): m/z 167 (M+H)$^+$, $R_t$: 0.27 min. $^1$H NMR (CDCl$_3$, 400 MHz): δ=8.64 (d, J=6.0 Hz, 2H), 7.46 (d, J=6.0 Hz, 2H), 3.47 (s, 3H), 3.30 (s, 3H).

I.4.3 4-Bromo-2-isonicotinoylthiophene-3-carboxylic acid

The title compound was prepared according to example I.1.3. Yield: 2.6 g (35%). LC-MS (Method A): m/z 312 (M+H)$^+$, $R_t$: 1.23 min. $^1$H NMR (DMSO-d, 400 MHz): δ=13.61 (s, 1H), 8.81-8.80 (m, 2H), 8.25 (s, 1H), 7.67-7.65 (m, 2H).

I.4.4 Ethyl 4-bromo-2-isonicotinoylthiophene-3-carboxylate

A mixture of 4-bromo-2-isonicotinoylthiophene-3-carboxylic acid (311 mg, 1 mmol), ethyl iodide (234 mg, 1.5 mmol), Cs$_2$CO$_3$ (652 mg, 2 mmol) in CH$_3$CN (50 mL) was stirred at 30° C. overnight. After completion of the reaction the solution was filtered and the volatile components removed under reduced pressure to give the title compound (305 mg, 90% yield) as yellow oil. The product was directly used for the next step without further purification. LC-MS (Method A): m/z 340 (M+H)$^+$, $R_t$: 1.95 min.

I.4.5 Ethyl 2-(pyridine-4-carbonyl)-4-(pyridin-4-yl)thiophene-3-carboxylate

The mixture of ethyl 4-bromo-2-isonicotinoylthiophene-3-carboxylate (325 mg, 0.96 mmol), 4-pyridineboronic acid (177 mg, 1.44 mmol), Na$_2$CO$_3$ (254 mg, 2.4 mmol) and PdCl$_2$(dppf) (63 mg, 0.077 mmol) was dissolved in 12 mL dioxane/H$_2$O (3:1). The mixture was stirred at 100° C. for 2 h. After completion of the reaction the resulting mixture was concentrated under reduced pressure. The material was loaded onto a silica gel column and eluted with 20%-50% EtOAc/PE. Elution fractions containing the desired compounds were collected and the solvent was removed under reduced pressure to provide the title compound (260 mg, 80% yield) as an orange oil. LC-MS (Method A): m/z 339 (M+H)$^+$, $R_t$: 1.77 min.

II. Preparation of Compounds of the Formula I

Example 1

5-methyl-7-(pyridin-4-yl)thieno[2,3-d]pyridazin-4(5H)-one (Comparative Example)

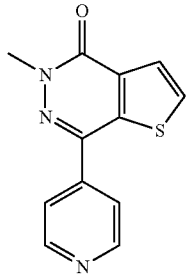 [SMILES: Cn1nc(-c2ccncc2)c2sccc2c1=O]

1.1 2-Isonicotinoylthiophene-3-carboxylic acid n-BuLi (23.2 mL, 56.2 mmol, 2.5M in THF) was added dropwise to a solution of diisopropylamine (5.2 g, 51.5 mmol) in anhydrous THF (40 mL) at −30° C. The mixture was stirred at the same temperature for 0.5 h and then cooled to −78° C. and HMPA (0.8 g, 4.7 mmol) was added slowly. Then a solution of thiophene-3-carboxylic acid (3.0 g, 23.4 mmol) in anhydrous THF (50 mL) was added slowly. The mixture was stirred at the same temperature for 1 h. Then N-methoxy-N-methyl-4-pyridinecarboxamide (5.0 g, 46.9 mmol) was added dropwise to the stirring mixture at −78° C. The reaction mixture was stirred for another 1 h at room temperature and was then quenched with H$_2$O (10 mL). The aqueous layer was acidified with 5% aq. HCl to pH 1-2 and the resulting precipitate collected by filtration. The filter cake was washed with DCM and the filtrate was extracted with DCM (3×200 mL). The organic layers were dried over Na$_2$SO$_4$ and concentrated under reduced pressure. The crude product was washed with DCM to give the title product (2.2 g, 40% yield) as a white solid. LC-MS (Method A): m/z 234 (M+H)$^+$, $R_t$: 0.57 min.

1.2 Ethyl 2-isonicotinoylthiophene-3-carboxylate

To a solution of 2-isonicotinoylthiophene-3-carboxylic acid (2.2 g, 9.4 mmol) from example 2.1 and Cs$_2$CO$_3$ (6.2 g, 18.9 mmol) in CH$_3$CN (500 mL) was added CH$_3$CH$_2$I (2.9 g, 18.9 mmol) dropwise. The mixture was stirred at 30° C. for 48 h. The mixture was filtered and concentrated to give the title compound (2.1 g, 85.5% yield) as yellow oil. LC-MS (Method A): m/z 340 (M+H)$^+$, $R_t$: 0.81 min.

1.3 5-methyl-7-(pyridin-4-yl)thieno[2,3-d]pyridazin-4(5H)-one

The title compound was prepared according to example I.1.5. Yield: 10 mg (14%). LC-MS (Method C): m/z 244 (M+H)$^+$, $R_t$: 2.13 min.

Example 2

5-methyl-3-(oxetan-3-ylamino)-7-(pyridin-4-yl)thieno[2,3-d]pyridazin-4(5H)-one

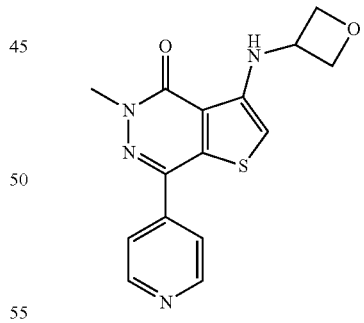

A solution of oxetanamine (23.8 mg, 0.33 mmol) in anhydrous toluene (2 mL) was degassed with argon in a microwave tube for 1.5 h. In parallel, a mixture of 3-bromo-5-methyl-7-(pyridin-4-yl)thieno[2,3-d]pyridazin-4(5H)-one (100 mg, 0.31 mmol—preparation example I.1), Pd$_2$(dba)$_3$·CHCl$_3$ (6.4 mg, 6.2 umol) and Cs$_2$CO$_3$ (202 mg, 0.62 mmol) was stirred under argon in a microwave tube for 1 h. Following this the degassed oxetanamine/toluene solution was added to the stirred mixture of solids and heated in an oil bath to 105° C. (oil bath temperature) for 24 h. After completion of the reaction, the mixture was cooled to RT and water and EtOAc were added. The organic layer was separated and the water phase extracted two times with EtOAc. The combined organic phases were washed once with water, dried over $Mg_2SO_4$ and the solvent removed under reduced pressure to leave a brown gum (~150 mg). The crude product was further purified by preparative HPLC using a combi-flash system equipped with a 4 g column. The product was eluted with a gradient comprising of increasing amounts of EtOAc in DCM. Fractions containing the wanted product were combined and the solvent was removed under reduced pressure to give the title compound (10 mg, 10.3% yield) as a yellow solid after drying in a vacuum oven. LC-MS: m/z 315 (M+H)$^+$, R$_t$: 2.8 min.

The compounds of EXAMPLES 3 to 5 were prepared in analogy to the method described in EXAMPLE 2.

| EX. | Name | LC-MS: m/z (M + H)$^+$/R$_t$ [min] |
|---|---|---|
| 3 | 5-methyl-3-(morpholin-4-yl)-7-(pyridin-4-yl)thieno[2,3-d]pyridazin-4(5H)-one | 329.1/2.69 |
| 4 | 3-(4-hydroxypiperidin-1-yl)-5-methyl-7-(pyridin-4-yl)thieno[2,3-d]pyridazin-4(5H)-one | 343.1/- |
| 5 | tert-butyl 4-[5-methyl-4-oxo-7-(pyridin-4-yl)-4,5-dihydrothieno[2,3-d]pyridazin-3-yl]piperazine-1-carboxylate | 428.1/2.17 |

Example 6

5-methyl-7-(pyridin-4-yl)-3-(pyrimidin-5-yl)thieno[2,3-d]pyridazin-4(5H)-one

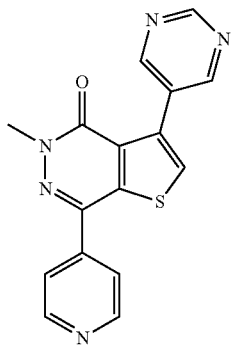 [SMILES: Cn1nc(-c2ccncc2)c2scc(-c3cncnc3)c2c1=O]

To a solution of the product from EXAMPLE 1.1 (50.0 mg, 0.155 mmol) and pyrimidine-5-boronic acid (20.2 mg, 0.163 mmol) in dioxane (1 mL) was added under argon 0.116 mL 2 M aq. $Na_2CO_3$ solution (24.7 mg, 0.233 mmol) and the catalyst Pd(PPh$_3$)$_4$ (35.9 mg, 0.031 mmol). The resulting solution was stirred at 120° C. in the microwave (200 W) for 2 h under argon. After completion of the reaction, the mixture was cooled to RT upon which a large amount of solid was formed. Water and EtOAc were added to the reaction suspension. The insoluble grey solid was filtered off, washed with a little water and EtOAc and the filter cake dissolved in DCM containing a few drops MeOH. The solution was filtered through celite to remove the Pd. The filtrate was concentrated under reduced pressure to give the title compound (10 mg, 19.1% yield) as an off-white solid after drying in a vacuum oven. LC-MS: m/z 322 (M+H)$^+$, R$_t$: 0.17 min.

The compounds of EXAMPLES 7 to 11 were prepared in analogy to the method described in EXAMPLE 6. For EXAMPLE 7, the 4,4,5,5-tetramethyl-1,3,2-dioxaborolane derivative instead of the boronic acids was used as the starting material.

| EX. | Name | LC-MS: m/z (M + H)$^+$/R$_t$ [min] |
|---|---|---|
| 7 | 5-methyl-3-(pyridazin-4-yl)-7-(pyridin-4-yl)thieno[2,3-d]pyridazin-4(5H)-one | 322.1/1.20 |
| 8 | 3-(4-fluorophenyl)-5-methyl-7-(pyridin-4-yl)thieno[2,3-d]pyridazin-4(5H)-one | 338.0/4.01 |
| 9 | 3[5-methyl-4-oxo-7-(pyridin-4-yl)-4,5-dihydrothieno[2,3-d]pyridazin-3-yl]benzonitrile | 345.1/1.54 |
| 10 | 3-(2-methoxypyrimidin-5-yl)-5-methyl-7-(pyridin-4-yl)thieno[2,3-d]pyridazin-4(5H)-one | 352.1/1.55 |

Example 11

5-methyl-7-(pyridin-4-yl)-3-(pyrimidin-5-yl)thieno[2,3-d]pyridazin-4(5H)-one (hydrochloride salt)

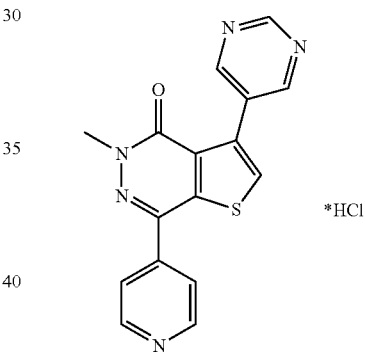

To a solution of the product from EXAMPLE 1.1 (200 mg, 0.621 mmol) and pyrimidine-5-boronic acid (81.0 mg, 0.652 mmol) in dioxin (6 mL) was added 2 M aq. $Na_2CO_3$ solution (99.0 mg, 0.931 mmol) and the catalyst Pd(PPh$_3$)$_4$ (143 mg, 0.124 mmol). The resulting solution was stirred at 120° C. in the microwave (200 W) for 2 h. After completion of the reaction, the mixture was cooled to RT upon which a large amount of solid was formed. Water and EtOAc were added to the reaction suspension. The insoluble grey solid was filtered off, washed with a little water and EtOAc and the filter cake dissolved in MeOH and 2 N HCl. The solution was filtered through celite to remove traces of Pd. Following this, 2 M NaOH was added to the acidic solution until pH 14 was reached. The beige solid which separated from the basic mixture was filtered off and washed with aq. MeOH. The beige solid was suspended in a mixture of diethyl ether (2 mL) and MeOH (4 mL), stirred for 2 h and filtered. Finally, the beige solid was suspended in a mixture of $CH_2Cl_2$ and MeOH, an excess of 1.25 M HCl in MeOH was added and the volatile components were removed under reduced pressure to give the title compound (37 mg, 16.3% yield) as an beige solid. LC-MS: m/z 322.1 (M+H)+, $R_t$: 1.03 min.

Example 12

5-methyl-3-(piperazin-1-yl)-7-(pyridin-4-yl)thieno[2,3-d]pyridazin-4(5H)-one (dihydrochloride salt)

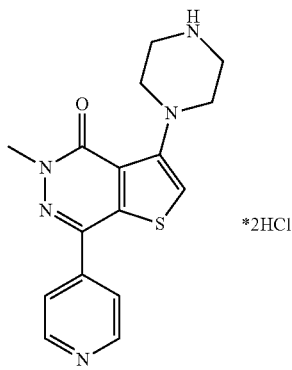 [SMILES: Cn1nc(-c2ccncc2)c2scc(N3CCNCC3)c2c1=O]

The product from EXAMPLE 5 (14.0 mg, 0.033 mmol) was dissolved in DCM (0.2 mL) and 0.21 mL 4 M HCl in dioxane (29.8 mg, 0.819 mmol) was added upon which a white solid was formed. The suspension was stirred for 3 days at RT. The solid was filtered off, washed with DCM and dissolved in MeOH. The solvent was removed under reduced pressure to give 12 mg of the title compound as a yellow solid after drying in a vacuum oven. Yield: 92%, assuming that the product is present as the dihydrochloride salt. LC-MS: m/z 328.1 (M+H)+, $R_t$: 0.23 min.

Example 13

5-methyl-3-(morpholin-4-ylmethyl)-7-(pyridin-4-yl)thieno[2,3-d]pyridazin-4(5H)-one

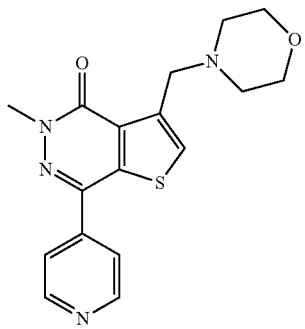 [SMILES: Cn1nc(-c2ccncc2)c2scc(CN3CCOCC3)c2c1=O]

To a solution of the product from EXAMPLE I.1 (80 mg, 0.248 mmol) and potassium (morpholin-4-yl)methyltrifluoroborate (56.6 mg, 0.273 mmol) in THF (3 mL) and water (0.3 mL) was added Cs₂CO₃ (324 mg, 0.993 mmol) and dicyclohexyl(2',4',6',-triisopropyldiphenyl-2-yl)phosphine. Following this, diacetoxypalladium (7.10 mg, 0.015 mmol) was added. The resulting mixture was stirred under argon at 100° C. in the microwave (200 W) for 2 h. After completion of the reaction, an excess of water and EtOAc were added upon which a grey solid was formed. The mixture was extracted two times with EtOAc. The combined extracts were washed once with water and dried over Mg₂SO₄. The organic solvent was removed under reduced pressure to leave a pale yellow semi-solid residue. The raw product was purified using a combi-flash system equipped with a 4 g column. The product was eluted with DCM containing increasing amounts of MeOH (1-15%). Fractions containing the wanted product were combined and the organic solvent was removed under reduced pressure to give the title compound (14 mg, 14.6% yield) as a pale yellow semi-solid residue after drying in a vacuum oven. LC-MS: m/z 343.1 (M+H)+, $R_t$: 0.32 min.

Example 14

5-methyl-3-(pyridin-3-yl)-7-(pyridin-4-yl)thieno[2,3-d]pyridazin-4(5H)-one bis(trifluoroacetate)

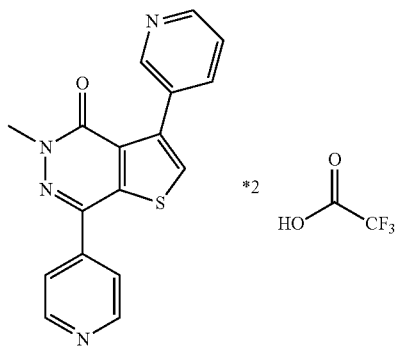 [SMILES: Cn1nc(-c2ccncc2)c2scc(-c3cccnc3)c2c1=O ; O=C(O)C(F)(F)F]

To a solution of the product from EXAMPLE 1.1 (64.5 mg, 0.20 mmol), 3-pyridylboronic acid (42.0 mg, 0.30 mmol) and Na₂CO₃ (50 mg, 0.47) in dioxane/H₂O (3:1) (2 mL) palladium catalyst PdCl₂(dppf) (10 mg, 0.014 mmol) was added. Following this, the mixture was stirred at 110° C. overnight under N₂ atmosphere. After filtration over celite, the filtrate was evaporated to dryness under reduced pressure. The residue was purified by preparative TLC to give the title compound as a white solid. LC-MS: m/z 321.1 (M+H)+, $R_t$: 1.93 min.

The compounds of EXAMPLES 15 to 16 were prepared in analogy to the method described in EXAMPLE 14.

| EX. | Name | LC-MS: m/z (M + H)+/$R_t$ [min] |
|---|---|---|
| 15 | 5-methyl-3-(pyridin-3-yl)-7-(pyridin-4-yl)thieno[2,3-d]pyridazin-4(5H)-one bis(trifluoroacetate) | 359.1/2.63 |
| 16 | 5-methyl-3-[(E)-2-phenylethenyl]-7-(pyridin-4-yl)thieno[2,3-d]pyridazin-4(5H)-one trifluoroacetate | 346.1/1.28 |

Example 17

5-methyl-7-(pyridin-4-yl)-3-(pyridin-3-ylethynyl)thieno[2,3-d]pyridazin-4(5H)-one bis(trifluoroacetate)

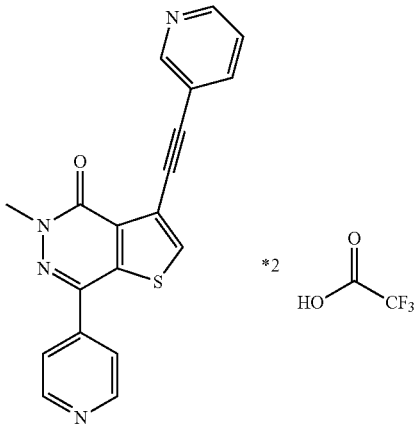 [SMILES: Cn1nc(-c2ccncc2)c2scc(C#Cc3cccnc3)c2c1=O ; O=C(O)C(F)(F)F]

To a solution of the product from EXAMPLE 1.1 (50.0 mg, 0.155 mmol) in THF (3 mL) was added PdCl₂(PPh₃)₂ (13.3 mg, 0.019 mmol) and CuI (7.0 mg, 0.037 mmol) in one portion at room temperature under N₂ atmosphere. The reaction mixture was stirred for 2 h at 30° C., then 3-ethynylpyridine (32.0 mg, 0.31 mmol) and piperidine (52.8 mg, 0.62 mmol) was added. Then the reaction mixture was stirred for 6 h at 60° C. under N₂ atmosphere. After completion of the reaction, the mixture was filtered and the filtrate was evaporation to dryness. The residual solid was purified by preparative HPLC to give the title compound as a white solid. LC-MS: m/z 345.1 (M+H)⁺, R$_t$: 2.24 min.

Example 18

N-benzyl-5-methyl-4-oxo-7-(pyridin-4-yl)-4,5-dihydrothieno[2,3-d]pyridazine-3-carboxamide trifluoroacetate

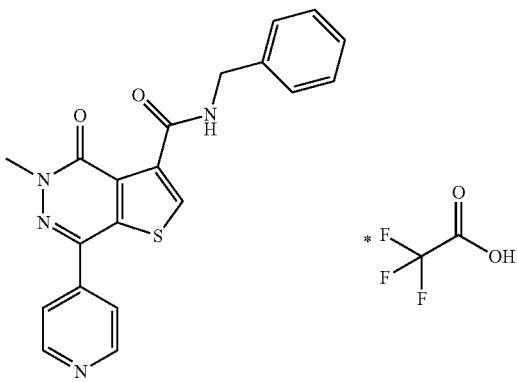 [SMILES: Cn1nc(-c2ccncc2)c2scc(C(=O)NCc3ccccc3)c2c1=O ; O=C(O)C(F)(F)F]

18.1 methyl 5-methyl-4-oxo-7-(pyridin-4-yl)thieno[2,3-d]pyridazine-3-carboxylate The mixture of the product from EXAMPLE 1.1 (1.87 g, 5.8 mmol), PdCl₂ (51 mg, 0.3 mmol), BINAP (385 mg, 0.58 mmol) and TEA (2 mL) in DMF (8 mL) and MeOH (4 mL) was stirred at 100° C. under CO atmosphere at 1.2 MPa for 48 h. The resulting mixture was filtered and the filtrate was concentrated in vacuum to dryness. The raw product was purified by preparative HPLC to give the title compound as a white solid.

18.2 5-methyl-4-oxo-7-(pyridin-4-yl)thieno[2,3-d]pyridazine-3-carboxylic acid The mixture of methyl 5-methyl-4-oxo-7-(pyridin-4-yl)thieno[2,3-d]pyridazine-3-carboxylate (1.70 g, 5.9 mmol) in EtOH (20 mL) and aq. NaOH solution (8%) was heated to reflux for 2 h. After completion of the reaction, the reaction mixture was concentrated in vacuum and the aqueous phase was washed with ether (50 mL). The aqueous layer was neutralized with aq. HCl (5%) to pH 6~7 and filtered. The residual was recrystallized from EtOH to give the title compound as a yellow solid.

18.3 N-benzyl-5-methyl-4-oxo-7-(pyridin-4-yl)-4,5-dihydrothieno[2,3-d]pyridazine-3-carboxamide trifluoroacetate The mixture of 5-methyl-4-oxo-7-(pyridin-4-yl)thieno[2,3-d]pyridazine-3-carboxylic acid (1.1 eq.) and HATU (3 eq.) in DMF (2 mL) was stirred for 30 min at RT. Then DIEA (4 eq.) and phenylmethanamine (1.4 eq.) was added to the above mixture. The reaction mixture was stirred overnight at 55° C. After evaporation, the residue was purified by preparative HPLC to give the title compound as solid. LC-MS: m/z 377.1 (M+H)⁺, R$_t$: 2.90 min.

The compounds of EXAMPLES 19 to 21 were prepared in analogy to the method described in EXAMPLE 18.

| EX. | Name | LC-MS: m/z (M + H)⁺/ R$_t$ [min] |
|---|---|---|
| 19 | 5-methyl-3-[(4-methylpiperazin-1-yl)carbonyl]-7-(pyridin-4-yl)thieno[2,3-d]pyridazin-4(5H)-one bis(trifluoroacetate) | 370.1/2.11 |
| 20 | N-benzyl-N-ethyl-5-methyl-4-oxo-7-(pyridin-4-yl)-4,5-dihydrothieno[2,3-d]pyridazine-3-carboxamide trifluoroacetate | 405.1/2.73 |
| 21 | N,N-diethyl-5-methyl-4-oxo-7-(pyridin-4-yl)-4,5-dihydrothieno[2,3-d]pyridazine-3-carboxamide trifluoroacetate | 343.1/2.46 |

Example 22

3-(4-methoxyphenyl)-5-methyl-7-(pyridin-4-yl)thieno[2,3-d]pyridazin-4(5H)-one trifluoroacetate

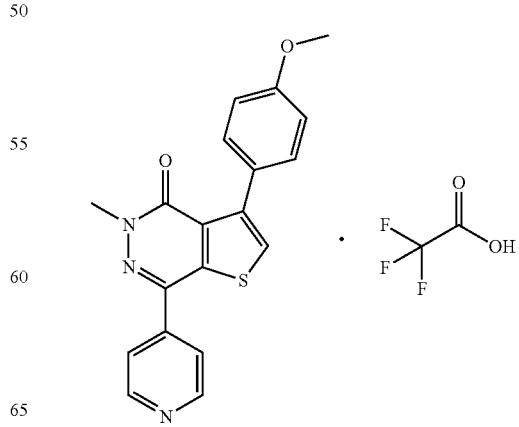

A 4 mL microwave vial was charged with a stir bar, a solution of the product from EXAMPLE 1.1 (23 mg, 0.07 mmol) in dioxane (1 mL), a solution of (4-methoxyphenyl)boronic acid monomer (16 mg, 1.5 eq., 0.11 mmol) in dioxane (1 mL), cesium carbonate (70 mg, 3 eq, 0.21 mmol) in water (0.21 mL) and with silicat resin (27 mg, 0.1 eq, 0.27 mmol loading). This mixture was placed in a parallel dual model microwave system Anton Parr and was allowed to heat at 150° C. for 30 min. After completion of the reaction, the crude product was dissolved in DMSO/MeOH (1:1) and purified by preparative reverse phase HPLC (TFA method) on a Phenomenex Luna C8(2) 5 um 100 Å AXIA column (30 mm×150 mm) A gradient of ACN (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A). The fractions containing the desired product were pooled and the solvent was removed under reduced pressure to give the title compound as a solid. The identity of the product was confirmed by $^1$H NMR and LC/MS. LC-MS: m/z 350.1 (M+H)$^+$.

The compounds of EXAMPLES 23 to 46 were prepared in analogy to the method described in EXAMPLE 22.

| EX. | Name | LC-MS: m/z (M + H)$^+$ |
|---|---|---|
| 23 | 3-(1-benzothiophen-2-yl)-5-methyl-7-(pyridin-4-yl)thieno[2,3-d]pyridazin-4(5H)-one trifluoroacetate | 376 |
| 24 | 5-methyl-3-[3-(1H-pyrazol-1-yl)phenyl]-7-(pyridin-4-yl)thieno[2,3-d]pyridazin-4(5H)-one bis(trifluoroacetate) | 386 |
| 25 | 4-[5-methyl-4-oxo-7-(pyridin-4-yl)-4,5-dihydrothieno[2,3-d]pyridazin-3-yl]benzonitrile trifluoroacetate | 345 |
| 26 | 3-(1-benzothiophen-3-yl)-5-methyl-7-(pyridin-4-yl)thieno[2,3-d]pyridazin-4(5H)-one trifluoroacetate | 376 |
| 27 | 3-(6-fluoropyridin-3-yl)-5-methyl-7-(pyridin-4-yl)thieno[2,3-d]pyridazin-4(5H)-one bis(trifluoroacetate) | 339 |
| 28 | 3-(4-hydroxyphenyl)-5-methyl-7-(pyridin-4-yl)thieno[2,3-d]pyridazin-4(5H)-one trifluoroacetate (salt) | 336 |
| 29 | 3-[5-methyl-4-oxo-7-(pyridin-4-yl)-4,5-dihydrothieno[2,3-d]pyridazin-3-yl]benzonitrile trifluoroacetate | 345 |
| 30 | 3-(3-methoxyphenyl)-5-methyl-7-(pyridin-4-yl)thieno[2,3-d]pyridazin-4(5H)-one trifluoroacetate | 350 |
| 31 | 3-(3-fluorophenyl)-5-methyl-7-(pyridin-4-yl)thieno[2,3-d]pyridazin-4(5H)-one trifluoroacetate | 338 |
| 32 | 5-methyl-3-[3-(morpholin-4-ylcarbonyl)phenyl]-7-(pyridin-4-yl)thieno[2,3-d]pyridazin-4(5H)-one trifluoroacetate | 432 |
| 33 | N-{4-[5-methyl-4-oxo-7-(pyridin-4-yl)-4,5-dihydrothieno[2,3-d]pyridazin-3-yl]phenyl}methanesulfonamide trifluoroacetate | 413 |
| 34 | 5-methyl-7-(pyridin-4-yl)-3-(thiophen-3-yl)thieno[2,3-d]pyridazin-4(5H)-one trifluoroacetate | 326 |
| 35 | 3-(2,3-dihydro-1-benzofuran-5-yl)-5-methyl-7-(pyridin-4-yl)thieno[2,3-d]pyridazin-4(5H)-one trifluoroacetate | 362 |
| 36 | 3-(2-fluorophenyl)-5-methyl-7-(pyridin-4-yl)thieno[2,3-d]pyridazin-4(5H)-one trifluoroacetate | 338 |
| 37 | 5-methyl-3-(1-methyl-1H-pyrazol-4-yl)-7-(pyridin-4-yl)thieno[2,3-d]pyridazin-4(5H)-one trifluoroacetate | 324 |
| 38 | 3-[4-(dimethylamino)phenyl]-5-methyl-7-(pyridin-4-yl)thieno[2,3-d]pyridazin-4(5H)-one bis(trifluoroacetate) | 363 |
| 39 | 3-(2-methoxyphenyl)-5-methyl-7-(pyridin-4-yl)thieno[2,3-d]pyridazin-4(5H)-one trifluoroacetate | 350 |
| 40 | N-cyclopropyl-4-[5-methyl-4-oxo-7-(pyridin-4-yl)-4,5-dihydrothieno[2,3-d]pyridazin-3-yl]benzamide trifluoroacetate | 403 |
| 41 | 3-(1-benzyl-1H-pyrazol-4-yl)-5-methyl-7-(pyridin-4-yl)thieno[2,3-d]pyridazin-4(5H)-one bis(trifluoroacetate) | 400 |
| 42 | 5-methyl-3-{3-[(4-methylpiperazin-1-yl)methyl]phenyl}-7-(pyridin-4-yl)thieno[2,3-d]pyridazin-4(5H)-one tris(trifluoroacetate) | 432 |
| 43 | 5-methyl-3-{4-[(4-methylpiperazin-1-yl)methyl]phenyl}-7-(pyridin-4-yl)thieno[2,3-d]pyridazin-4(5H)-one tris(trifluoroacetate) | 432 |
| 44 | 3-(2-hydroxyphenyl)-5-methyl-7-(pyridin-4-yl)thieno[2,3-d]pyridazin-4(5H)-one trifluoroacetate (salt) | 336 |
| 45 | 5-methyl-3-(4-methylphenyl)-7-(pyridin-4-yl)thieno[2,3-d]pyridazin-4(5H)-one trifluoroacetate | 334 |
| 46 | 3-(1,3-benzodioxol-5-yl)-5-methyl-7-(pyridin-4-yl)thieno[2,3-d]pyridazin-4(5H)-one trifluoroacetate | 364 |

Example 47

5-methyl-7-(piperidin-1-yl)-3-(pyridin-4-yl)thieno[2,3-d]pyridazin-4(5H)-one

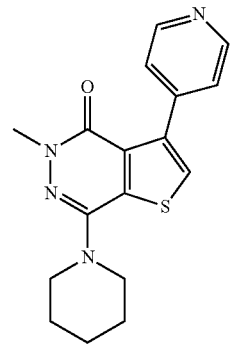 [SMILES: Cn1nc(N2CCCCC2)c2scc(-c3ccncc3)c2c1=O]

A mixture of the product from EXAMPLE I.2 (40.0 mg, 0.114 mmol) in 0.43 mL piperidine (368 mg, 4.32 mmol) was heated in the microwave at 150° C. for a total of 12 h. After completion of the reaction, an excess of water was added and the resulting mixture was extracted two times with EtOAc. The combined extracts were washed once with water, dried over Mg$_2$SO$_4$ and the organic solvent was removed under reduced pressure to leave an orange gum (~40 mg). The crude product was purified using a combi-flash system equipped with a 4 g column. The desired product was eluted with DCM containing increasing amounts of MeOH (1-20%). Fractions containing the pure product were combined and the solvent was evaporated under reduced pressure to give the title compound (7.0 mg, 14.9% yield) as an off-white semi-solid residue after drying in the vacuum oven. LC-MS: m/z 327.1 (M+H)$^+$, R$_t$: 2.06 min.

The compounds of EXAMPLES 48 to 50 were prepared in analogy to the method described in EXAMPLE 47.

| EX. | Name | LC-MS: m/z (M + H)+/ $R_t$ [min] |
|---|---|---|
| 48 | 3-(4-fluorophenyl)-5-methyl-7-(pyridin-4-yl)thieno[2,3-d]pyridazin-4(5H)-one | 329.1/1.64 |
| 49 | 5-methyl-7-(4-methylpiperazin-1-yl)-3-(pyridin-4-yl)thieno[2,3-d]pyridazin-4(5H)-one | 342.1/0.21 |
| 50 | 7-(benzylamino)-5-methyl-3-(pyridin-4-yl)thieno[2,3-d]pyridazin-4(5H)-one bis(trifluoroacetate) | 349.1/1.37 |

Example 51

7-[2-(dimethylamino)ethoxy]-5-methyl-3-(pyridin-4-yl)thieno[2,3-d]pyridazin-4(5H)-one

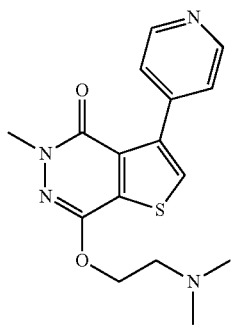

To a solution of N,N-dimethylethanolamine (25.7 mg, 0.288 mmol) in DMF (2 mL) NaH (11.8 mg, 0.295 mmol) was added and stirred at for 20 min at RT under argon. Then, the product from EXAMPLE I.2 (40.0 mg, 0.114 mmol) was added. The reaction mixture was stirred overnight at RT under argon. The reaction suspension was treated with water (20 mL) and the aqueous mixture extracted two times with EtOAc. The combined extracts were washed once with water, dried over $Mg_2SO_4$ and the organic solvent was removed under reduced pressure. The residual gum was triturated in diethyl ether/heptane (1:1) resulting in the formation of an solid which was filtered off and dried in a vacuum oven to give the title compound (11 mg, 23.1% yield) as a off-white solid. LC-MS: m/z 331.2 (M+H)+, $R_t$: 0.41 min.

The compounds of EXAMPLES 52 to 80 were prepared in analogy to the method described in EXAMPLE 51. If necessary, the compounds were purified by preparative HPLC.

| EX. | Name | LC-MS: m/z (M + H)+/ $R_t$ [min] |
|---|---|---|
| 52 | 7-(furan-2-ylmethoxy)-5-methyl-3-(pyridin-4-yl)thieno[2,3-d]pyridazin-4(5H)-one | 340.1/1.38 |
| 53 | 7-(cyclohexyloxy)-5-methyl-3-(pyridin-4-yl)thieno[2,3-d]pyridazin-4(5H)-one trifluoroacetate | 342.1/4.65 |
| 54 | 7-(benzyloxy)-5-methyl-3-(pyridin-4-yl)thieno[2,3-d]pyridazin-4(5H)-one | 350.1/1.84 |
| 55 | 5-methyl-3-(pyridin-4-yl)-7-(pyridin-2-ylmethoxy)thieno[2,3-d]pyridazin-4(5H)-one | 351.1/1.08 |
| 56 | 5-methyl-7-[(1-methyl-1H-imidazol-2-yl)methoxy]-3-(pyridin-4-yl)thieno[2,3-d]pyridazin-4(5H)-one | 354.1/0.41 |
| 57 | 7-(cyclohexylmethoxy)-5-methyl-3-(pyridin-4-yl)thieno[2,3-d]pyridazin-4(5H)-one | 356.2/2.13 |
| 58 | 5-methyl-3-(pyridin-4-yl)-7-(1,3-thiazol-2-ylmethoxy)thieno[2,3-d]pyridazin-4(5H)-one | 357.1/1.43 |
| 59 | 3-({[5-methyl-4-oxo-3-(pyridin-4-yl)-4,5-dihydrothieno[2,3-d]pyridazin-7-yl]oxy}methyl)benzonitrile trifluoroacetate | 375.1/1.43 |
| 60 | 7-(2,3-dihydro-1H-inden-2-yloxy)-5-methyl-3-(pyridin-4-yl)thieno[2,3-d]pyridazin-4(5H)-one trifluoroacetate | 376.1/1.66 |
| 61 | 7-[(3-methoxybenzyl)oxy]-5-methyl-3-(pyridin-4-yl)thieno[2,3-d]pyridazin-4(5H)-one | 380.1/1.53 |
| 62 | 7-[(4-chlorobenzyl)oxy]-5-methyl-3-(pyridin-4-yl)thieno[2,3-d]pyridazin-4(5H)-one | 384.1/1.69 |
| 63 | 7-(1-benzofuran-3-ylmethoxy)-5-methyl-3-(pyridin-4-yl)thieno[2,3-d]pyridazin-4(5H)-one | 390.1/6.22 |
| 64 | 7-(1-benzofuran-7-ylmethoxy)-5-methyl-3-(pyridin-4-yl)thieno[2,3-d]pyridazin-4(5H)-one | 390.1/1.58 |
| 65 | 5-methyl-7-{[3-(propan-2-yl)benzyl]oxy}-3-(pyridin-4-yl)thieno[2,3-d]pyridazin-4(5H)-one trifluoroacetate | 392.1/— |
| 66 | 7-[(4,4-difluorocyclohexyl)methoxy]-5-methyl-3-(pyridin-4-yl)thieno[2,3-d]pyridazin-4(5H)-one | 392.1/1.89 |
| 67 | 3-({[5-methyl-4-oxo-3-(pyridin-4-yl)-4,5-dihydrothieno[2,3-d]pyridazin-7-yl]oxy}methyl)benzamide trifluoroacetate | 393.1/1.17 |
| 68 | 3-({[5-methyl-4-oxo-3-(pyridin-4-yl)-4,5-dihydrothieno[2,3-d]pyridazin-7-yl]oxy}methyl)benzamide | 393.1/1.20 |
| 69 | 7-(1,3-benzodioxol-5-ylmethoxy)-5-methyl-3-(pyridin-4-yl)thieno[2,3-d]pyridazin-4(5H)-one | 394.1/1.50 |
| 70 | 5-methyl-7-[(1-methyl-1H-benzimidazol-2-yl)methoxy]-3-(pyridin-4-yl)thieno[2,3-d]pyridazin-4(5H)-one | 404.2/1.18 |
| 71 | 7-(1,3-benzothiazol-2-ylmethoxy)-5-methyl-3-(pyridin-4-yl)thieno[2,3-d]pyridazin-4(5H)-one trifluoroacetate | 407.1/2.15 |
| 72 | methyl 3-({[5-methyl-4-oxo-3-(pyridin-4-yl)-4,5-dihydrothieno[2,3-d]pyridazin-7-yl]oxy}methyl)benzoate trifluoroacetate | 403.1/1.73 |
| 73 | 5-methyl-7-{[3-(propan-2-yloxy)benzyl]oxy}-3-(pyridin-4-yl)thieno[2,3-d]pyridazin-4(5H)-one | 408.1/1.79 |
| 74 | N-(2-hydroxyphenyl)-2-{[5-methyl-4-oxo-3-(pyridin-4-yl)-4,5-dihydrothieno[2,3-d]pyridazin-7-yl]oxy}acetamide trifluoroacetate | 409.1/1.28 |
| 75 | 7-[(3,5-dimethoxybenzyl)oxy]-5-methyl-3-(pyridin-4-yl)thieno[2,3-d]pyridazin-4(5H)-one | 410.1/1.55 |
| 76 | 7-{[3-(difluoromethoxy)benzyl]oxy}-5-methyl-3-(pyridin-4-yl)thieno[2,3-d]pyridazin-4(5H)-one | 416.1/1.57 |
| 77 | 7-[(3,4-dichlorobenzyl)oxy]-5-methyl-3-(pyridin-4-yl)thieno[2,3-d]pyridazin-4(5H)-one | 418.0/1.88 |
| 78 | 5-methyl-7-[1-(1-methyl-1H-benzimidazol-2-yl)ethoxy]-3-(pyridin-4-yl)thieno[2,3-d]pyridazin-4(5H)-one | 418.1/1.22 |
| 79 | tert-butyl 4-({[5-methyl-4-oxo-3-(pyridin-4-yl)-4,5-dihydrothieno[2,3-d]pyridazin-7-yl]oxy}methyl)piperidine-1-carboxylate | 457.2/2.00 |
| 80 | tert-butyl 5-({[5-methyl-4-oxo-3-(pyridin-4-yl)-4,5-dihydrothieno[2,3-d]pyridazin-7-yl]oxy}methyl)-1,3-dihydro-2H-isoindole-2-carboxylate | 491.2/2.11 |

Example 81

5-methyl-7-phenoxy-3-(pyridin-4-yl)thieno[2,3-d]pyridazin-4(5H)-one

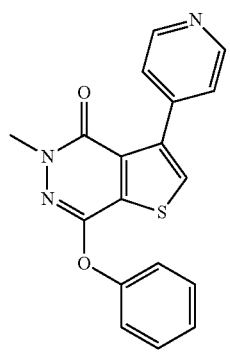 [SMILES: Cn1nc(Oc2ccccc2)c2scc(-c3ccncc3)c2c1=O]

A mixture of the product from EXAMPLE 1.2 (20.0 mg, 0.072 mmol), phenol (13.6 mg, 0.144 mmol) and $Cs_2CO_3$ (46.9 mg, 0.144 mmol) in DMF (1 mL) was stirred and heated in a CEM microwave at 150° C. for 2 h. After completion of the reaction, the mixture was cooled to RT and an excess of water was added. The beige solid which separated was filtered off, washed with water and some heptane and dried in the vacuum oven to give the title compound (15 mg, 62.1% yield) as an beige solid. LC-MS: m/z 336.1 $(M+H)^+$, $R_t$: 1.98 min.

The compounds of EXAMPLES 82 to 93 were prepared in analogy to the method described in EXAMPLE 81. If necessary, the compounds were purified by preparative HPLC.

| EX. | Name | LC-MS: m/z $(M + H)^+$/ $R_t$ [min] |
|---|---|---|
| 82 | 5-methyl-3-(pyridin-4-yl)-7-(pyridin-3-yloxy)thieno[2,3-d]pyridazin-4(5H)-one | 337.1/1.11 |
| 83 | 2-{[5-methyl-4-oxo-3-(pyridin-4-yl)-4,5-dihydrothieno[2,3-d]pyridazin-7-yl]oxy}benzonitrile trifluoroacetate | 361.1/1.37 |
| 84 | 7-(2-methoxyphenoxy)-5-methyl-3-(pyridin-4-yl)thieno[2,3-d]pyridazin-4(5H)-one trifluoroacetate | 366.1/1.41 |
| 85 | 7-(3-methoxyphenoxy)-5-methyl-3-(pyridin-4-yl)thieno[2,3-d]pyridazin-4(5H)-one | 366.1/4.25 |
| 86 | 7-(4-methoxyphenoxy)-5-methyl-3-(pyridin-4-yl)thieno[2,3-d]pyridazin-4(5H)-one | 366.1/1.70 |
| 87 | 7-(3-hydroxy-5-methoxypyridin-2-yl)-5-methyl-3-(pyridin-4-yl)thieno[2,3-d]pyridazin-4(5H)-one bis(trifluoroacetate) (salt) | 367.1/— |
| 88 | 7-[(5-methoxypyridin-3-yl)oxy]-5-methyl-3-(pyridin-4-yl)thieno[2,3-d]pyridazin-4(5H)-one bis(trifluoroacetate) | 367.1/— |
| 89 | 7-(1,3-benzodioxol-5-yloxy)-5-methyl-3-(pyridin-4-yl)thieno[2,3-d]pyridazin-4(5H)-one | 380.1/1.42 |
| 90 | 7-[(2-chloro-5-methylpyridin-3-yl)oxy]-5-methyl-3-(pyridin-4-yl)thieno[2,3-d]pyridazin-4(5H)-one trifluoroacetate | 385.1/1.45 |
| 91 | 7-(3,4-dimethoxyphenoxy)-5-methyl-3-(pyridin-4-yl)thieno[2,3-d]pyridazin-4(5H)-one | 396.1/3.94 |
| 92 | 7-(3,5-dimethoxyphenoxy)-5-methyl-3-(pyridin-4-yl)thieno[2,3-d]pyridazin-4(5H)-one | 396.1/3.74 |
| 93 | 7-{[6-(benzyloxy)pyridin-3-yl]oxy}-5-methyl-3-(pyridin-4-yl)thieno[2,3-d]pyridazin-4(5H)-one bis(trifluoroacetate) | 443.1/1.83 |

Example 94

3-[5-methyl-4-oxo-3-(pyridin-4-yl)-4,5-dihydrothieno[2,3-d]pyridazin-7-yl]benzonitrile

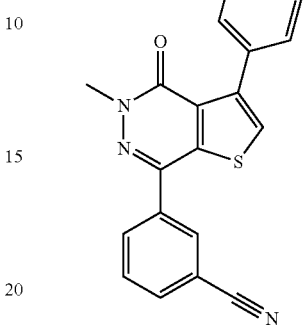

To a solution of the product from EXAMPLE I.2 (80.0 mg, 0.288 mmol) and 3-cyanophenylboronic acid (46.6 mg, 0.317 mmol) in dioxane (3 mL) was added under argon 0.216 mL 2 M aq. $Na_2CO_3$ solution (45.8 mg, 0.432 mmol) and the catalyst $Pd(PPh_3)_4$ (66.6 mg, 0.058 mmol). The resulting solution was stirred at 120° C. in the microwave (200 W) for 2 h under argon. After completion of the reaction, the mixture was cooled to RT and water was added leading to the formation of a solid. The suspension was extracted three times with a mixture of EtOAc and DCM. The combined organic phases were washed one time with water, dried over $Mg_2SO_4$ and the concentrated to dryness under reduced pressure to give a beige solid. The solid was triturated with a small volume of toluene which, filtered off and dried in an vacuum oven to give the title compound (15 mg, 15.1% yield) as an off-white solid. LC-MS: m/z 344.8 $(M+H)^+$, $R_t$: 1.33 min.

The compounds of EXAMPLES 95 to 122 were prepared in analogy to the method described in EXAMPLE 94. For EXAMPLES 99 and 100, the 4,4,5,5-tetramethyl-1,3,2-dioxaborolane derivatives instead of the boronic acids were used as the starting material. If necessary, the compounds were purified by preparative HPLC.

| EX. | Name | LC-MS: m/z $(M + H)^+$/ $R_t$ [min] |
|---|---|---|
| 95 | 4-[5-methyl-4-oxo-3-(pyridin-4-yl)-4,5-dihydrothieno[2,3-d]pyridazin-7-yl]benzonitrile | 345.1/1.82 |
| 96 | 7-(4-methoxyphenyl)-5-methyl-3-(pyridin-4-yl)thieno[2,3-d]pyridazin-4(5H)-one | 350.1/2.00 |
| 97 | 7-(1,3-benzoxazol-6-yl)-5-methyl-3-(pyridin-4-yl)thieno[2,3-d]pyridazin-4(5H)-one | 361.1/— |
| 98 | 2-[5-methyl-4-oxo-3-(pyridin-4-yl)-4,5-dihydrothieno[2,3-d]pyridazin-7-yl]benzamide | 363.1/1.12 |
| 99 | 7-[1-(2-methoxyethyl)-1H-pyrazol-4-yl]-5-methyl-3-(pyridin-4-yl)thieno[2,3-d]pyridazin-4(5H)-one bis(trifluoroacetate) | 368.1/1.20 |
| 100 | 5-methyl-3-(pyridin-4-yl)-7-[1-(2,2,2-trifluoroethyl)-1H-pyrazol-4-yl]thieno[2,3-d]pyridazin-4(5H)-one bis(trifluoroacetate) | 392.1/1.31 |
| 101 | 5-methyl-3-(pyridin-4-yl)-7-[4-(trifluoromethoxy)phenyl]thieno[2,3-d]pyridazin-4(5H)-one | 404.1/1.70 |
| 102 | 7-(3,4-dimethoxyphenyl)-5-methyl-3-(pyridin-4-yl)thieno[2,3-d]pyridazin-4(5H)-one trifluoroacetate | 380/— |

-continued

| EX. | Name | LC-MS: m/z (M + H)+/ $R_t$ [min] |
|---|---|---|
| 103 | 7-(4-fluorophenyl)-5-methyl-3-(pyridin-4-yl)thieno[2,3-d]pyridazin-4(5H)-one trifluoroacetate | 338/— |
| 104 | 7-(2-fluoropyridin-4-yl)-5-methyl-3-(pyridin-4-yl)thieno[2,3-d]pyridazin-4(5H)-one bis(trifluoroacetate) | 339/— |
| 105 | 7-(3-chlorophenyl)-5-methyl-3-(pyridin-4-yl)thieno[2,3-d]pyridazin-4(5H)-one trifluoroacetate | 354/— |
| 106 | 7-(biphenyl-4-yl)-5-methyl-3-(pyridin-4-yl)thieno[2,3-d]pyridazin-4(5H)-one trifluoroacetate | 396/— |
| 107 | 7-(3-hydroxyphenyl)-5-methyl-3-(pyridin-4-yl)thieno[2,3-d]pyridazin-4(5H)-one trifluoroacetate (salt) | 336/— |
| 108 | 5-methyl-7-(4-phenoxyphenyl)-3-(pyridin-4-yl)thieno[2,3-d]pyridazin-4(5H)-one trifluoroacetate | 412/— |
| 109 | 7-(2,4-dichlorophenyl)-5-methyl-3-(pyridin-4-yl)thieno[2,3-d]pyridazin-4(5H)-one trifluoroacetate | 388/— |
| 110 | 7-(4-chlorophenyl)-5-methyl-3-(pyridin-4-yl)thieno[2,3-d]pyridazin-4(5H)-one trifluoroacetate | 354/— |
| 111 | 7-(3,5-dimethoxyphenyl)-5-methyl-3-(pyridin-4-yl)thieno[2,3-d]pyridazin-4(5H)-one trifluoroacetate | 380/— |
| 112 | 5-methyl-3-(pyridin-4-yl)-7-[3-(trifluoromethoxy)phenyl]thieno[2,3-d]pyridazin-4(5H)-one trifluoroacetate | 404/— |
| 113 | 7-(2-methoxyphenyl)-5-methyl-3-(pyridin-4-yl)thieno[2,3-d]pyridazin-4(5H)-one trifluoroacetate | 350/— |
| 114 | 5-methyl-3-(pyridin-4-yl)-7-[3-(trifluoromethyl)phenyl]thieno[2,3-d]pyridazin-4(5H)-one trifluoroacetate | 388/— |
| 115 | 7-(2-fluorophenyl)-5-methyl-3-(pyridin-4-yl)thieno[2,3-d]pyridazin-4(5H)-one trifluoroacetate | 338/— |
| 116 | 7-(3-fluorophenyl)-5-methyl-3-(pyridin-4-yl)thieno[2,3-d]pyridazin-4(5H)-one trifluoroacetate | 338/— |
| 117 | 5-methyl-3-(pyridin-4-yl)-7-[4-(trifluoromethyl)phenyl]thieno[2,3-d]pyridazin-4(5H)-one trifluoroacetate | 388/— |
| 118 | 7-(4-hydroxyphenyl)-5-methyl-3-(pyridin-4-yl)thieno[2,3-d]pyridazin-4(5H)-one trifluoroacetate (salt) | 336/— |
| 119 | 7-[3-(dimethylamino)phenyl]-5-methyl-3-(pyridin-4-yl)thieno[2,3-d]pyridazin-4(5H)-one bis(trifluoroacetate) | 363/— |
| 120 | 5-methyl-7-(2-methylpyridin-4-yl)-3-(pyridin-4-yl)thieno[2,3-d]pyridazin-4(5H)-one bis(trifluoroacetate) | 335/— |
| 121 | 5-methyl-7-(4-methylphenyl)-3-(pyridin-4-yl)thieno[2,3-d]pyridazin-4(5H)-one trifluoroacetate | 334/— |
| 122 | 5-methyl-3-(pyridin-4-yl)-7-[4-(trifluoromethoxy)phenyl]thieno[2,3-d]pyridazin-4(5H)-one trifluoroacetate | 404/— |

Example 123

7-(3-methoxyphenyl)-5-methyl-3-(pyridin-4-yl)thieno[2,3-d]pyridazin-4(5H)-one

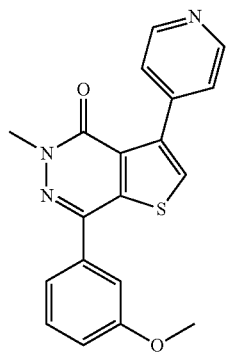 [SMILES: COc1cccc(-c2nn(C)c(=O)c3c(-c4ccncc4)csc23)c1]

A mixture of the product from EXAMPLE I.2 (80.0 mg, 0.288 mmol), 3-methoxyphenylboronic acid (48.1 mg, 0.317 mmol) $K_2CO_3$ (80.0 mg, 0.576 mmol) and the catalyst $PdCl_2$(dppf).$CH_2Cl_2$ (23.5 mg, 0.029 mmol) were stirred at RT under argon. Dioxane (3 mL) and water (0.5 mL) were degassed with argon and added to the mixture of solids. The resulting mixture was stirred at 120° C. in the microwave (200 W) for 2 h under argon. After completion of the reaction, the mixture was cooled to RT and water was added leading to the formation of a solid. The suspension was extracted three times with DCM containing a few drops of MeOH. The combined extracts were washed one time with water, dried over $Mg_2SO_4$ and the concentrated to dryness under reduced pressure to give a dark solid. The crude product was transferred onto a combi-flash system equipped with a 4 g column and eluted with DCM containing increasing amounts of MeOH (2-12%). Fractions containing the desired product were combined, the organic solvent evaporated under reduced pressure and the resulting off-white solid triturated with diethyl ether. The solid was filtered off and dried in a vacuum oven to give the title compound (10 mg, 9.9% yield) as an off-white solid. LC-MS: m/z 350.1 (M+H)+, $R_t$: 1.41 min.

Example 124

7-(1,3-benzodioxol-5-yl)-5-methyl-3-(pyridin-4-yl)thieno[2,3-d]pyridazin-4(5H)-one

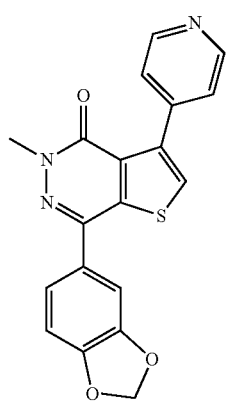 [SMILES: Cn1nc(-c2ccc3c(c2)OCO3)c2scc(-c3ccncc3)c2c1=O]

The title compound was prepared in analogy to the method described in EXAMPLE 123. Yield: 85 mg, 81%. LC-MS: m/z 364.1 (M+H)⁺, R_t: 1.42 min.

Example 125

5-methyl-7-(piperidin-4-ylmethoxy)-3-(pyridin-4-yl)thieno[2,3-d]pyridazin-4(5H)-one bis(trifluoroacetate)

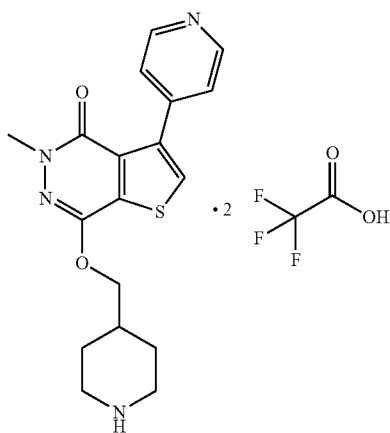 [SMILES: Cn1nc(OCC2CCNCC2)c2scc(-c3ccncc3)c2c1=O ; O=C(O)C(F)(F)F]

The product from EXAMPLE 79 (10.0 mg, 0.022 mmol) was dissolved in DCM (0.5 mL) and 8.44 uL TFA (12.5 mg, 0.110 mmol) was added upon which a white solid was formed. The suspension was stirred overnight at RT. After completion of the reaction, the solvent was removed under reduced pressure. The resulting yellow gum was triturated with diethyl ether, filtered off and dried in a vacuum oven to give the title compound (12 mg, 94% yield) as a yellow solid. LC-MS: m/z 357.2 (M+H)⁺, R_t: 1.06 min.

Example 126

7-(2,3-dihydro-1H-isoindol-5-ylmethoxy)-5-methyl-3-(pyridin-4-yl)thieno[2,3-d]pyridazin-4(5H)-one bis(trifluoroacetate)

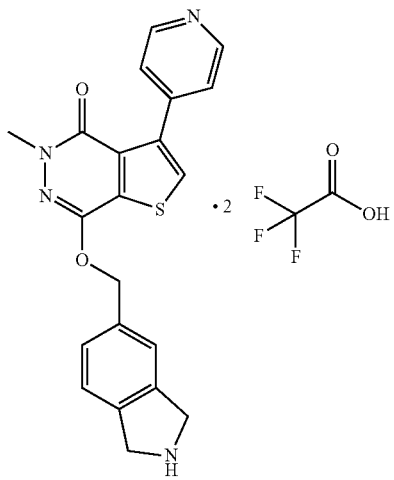 [SMILES: Cn1nc(OCc2ccc3c(c2)CNC3)c2scc(-c3ccncc3)c2c1=O ; O=C(O)C(F)(F)F]

The title compound was prepared from the product of EXAMPLE 80 in analogy to the method described in EXAMPLE 125. Yield: 6.3 mg, 100%. LC-MS: m/z 391.2 (M+H)⁺, R_t: 1.26 min.

EXAMPLES 127 to 129 were prepared from 3-bromo-7-(pyridin-4-yl)-5-(2,2,2-trifluoroethyl)thieno[2,3-d]pyridazin-4(5H)-one (product of EXAMPLE 1.3) in analogy to the method described in EXAMPLE 6 and 94. For EXAMPLE 128 the 4,4,5,5-tetramethyl-1,3,2-dioxaborolane derivative instead of the boronic acid was used as the starting material.

| EX. | Name | LC-MS: m/z (M + H)⁺/ R_t [min] |
|---|---|---|
| 127 | 3-[4-oxo-7-(pyridin-4-yl)-5-(2,2,2-trifluoroethyl)-4,5-dihydrothieno[2,3-d]pyridazin-3-yl]benzonitrile | 390.1/1.44 |
| 128 | 3-(2-methylpyrimidin-5-yl)-7-(pyridin-4-yl)-5-(2,2,2-trifluoroethyl)thieno[2,3-d]pyridazin-4(5H)-one | 404.1/1.51 |
| 129 | 3-[4-oxo-7-(pyridin-4-yl)-5-(2,2,2-trifluoroethyl)-4,5-dihydrothieno[2,3-d]pyridazin-3-yl]benzonitrile | 413.0/1.97 |

Example 130

5-methyl-3,7-di(pyridin-4-yl)thieno[2,3-d]pyridazin-4(5H)-one

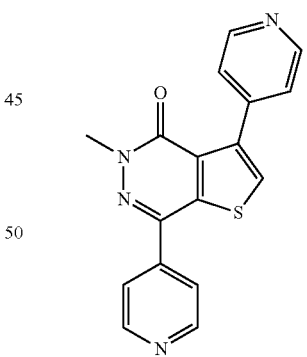

A suspension of the product from EXAMPLE I.4 (170 mg, 0.55 mmol) and methyl-hydrazine (76 mg, 1.65 mmol) in EtOH (8 mL) was irradiated by microwave at 150° C. for 30 min. After removal of solvent, the crude product was purified by preparative HPLC to give the title compound (90 mg, 51% yield) as white solid. LC-MS (Method A): m/z 321.1 (M+H)⁺, R_t: 1.1 min. ¹H NMR (CDCl₃, 400 MHz): δ=8.85-8.83 (m, 2H), 8.76-8.74 (m, 2H), 7.84-7.83 (m, 2H), 7.76 (s, 1H), 7.72-7.71 (m, 2H), 3.95 (s, 3H).

Example 131

3,7-di(pyridin-4-yl)-5-(2,2,2-trifluoroethyl)thieno[2,3-d]pyridazin-4(5H)-one

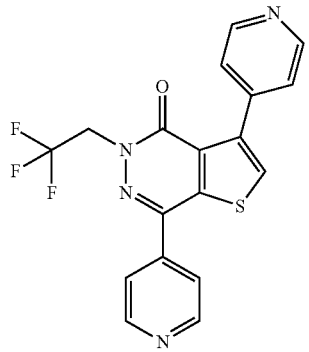 [SMILES: O=c1c2c(-c3ccncc3)csc2c(-c2ccncc2)nn1CC(F)(F)F]

131.1 3,7-di(pyridin-4-yl)-5H-thieno[2,3-d]pyridazin-4(5H)-one

To a solution of the product from EXAMPLE I.4 (100 mg, 0.30 mmol) in EtOH (5 mL) was added $NH_2NH_2 \cdot H_2O$ (0.5 mL). The solution was stirred at RT for 30 min. The solid was filtered, collected and directly used for the next step without further purification (86 mg, 95% yield).

131.2 3,7-di(pyridin-4-yl)-5-(2,2,2-trifluoroethyl)thieno[2,3-d]pyridazin-4(5H)-one To a solution of 3,7-di(pyridin-4-yl)-5H-thieno[2,3-d]pyridazin-4(5H)-one (86.0 mg, 0.30 mmol) and 1,1,1-trifluoro-2-iodoethane (94.5 mg, 0.45 mmol) in DMF (3 mL) was added $Cs_2CO_3$ (196 mg, 0.60 mmol). The mixture was stirred at 30° C. overnight. The solution was filtered and purified by preparative HPLC. LC-MS (Method A): m/z 389 $(M+H)^+$, $R_t$: 1.83 min. $^1H$ NMR ($CDCl_3$, 400 MHz): δ=8.86 (dd, J=4.8, 1.6 Hz, 2H), 8.72 (d, J=6 Hz, 2H), 7.80 (dd, J=4.4 Hz, 1.6 Hz, 2H), 7.73 (s, 1H), 7.49 (dd, J=4.4 Hz, 1.6 Hz, 2H), 4.95 (q, J=8.0 Hz, 2H).

The compounds of EXAMPLES 132 to 144 were prepared in analogy to the method described in EXAMPLE 131. For all examples, either alkyl iodides or alkyl bromides were used as the alkylating agent. The final compounds were purified by preparative HPLC.

| EX. | Name | LC-MS: m/z $(M + H)^+$/ $R_t$ [min] | $^1H$ NMR ($CDCl_3$, 400 MHz) δ: |
|---|---|---|---|
| 132 | 5-tert-butyl-3,7-di(pyridin-4-yl)thieno[2,3-d]pyridazin-4(5H)-one | 363/2.01 | 8.81 (m, 2H), 8.71 (d, J = 5.6 Hz, 2H), 7.84 (dd, J = 4.4 Hz, 1.6 Hz, 2H), 7.59 (s, 1H), 7.52 (dd, J = 4.4 Hz, 1.2 Hz, 2H), 1.77 (s, 9H) |
| 133 | 5-cyclohexyl-3,7-di(pyridin-4-yl)thieno[2,3-d]pyridazin-4(5H)-one | 389/2.08 | 8.85 (br, 2H), 8.69 (br, 2H), 7.86 (s, 2H), 7.64 (s, 1H), 7.53 (s, 2H), 5.11-5.03 (m, 1H), 1.96-1.24 (m, 10H) |
| 134 | 5-cyclopentyl-3,7-di(pyridin-4-yl)thieno[2,3-d]pyridazin-4(5H)-one | 375/1.99 | 8.83 (d, J = 6.0 Hz, 2H), 8.71 (d, J = 5.6 Hz, 2H), 7.84 (dd, J = 4.4 Hz, 1.6 Hz, 2H), 7.65 (s, 1H), 7.52 (dd, J = 4.8 Hz, 1.6 Hz, 2H), 5.60-5.57 (m, 1H), 2.16-1.71 (m, 8H) |
| 135 | 5-(propan-2-yl)-3,7-di(pyridin-4-yl)thieno[2,3-d]pyridazin-4(5H)-one | 349/1.86 | 8.83 (s, 2H), 8.69 (s, 2H), 7.86 (s, 2H), 7.65 (s, 1H), 7.52 (s, 2H), 5.51-5.44 (m, 1H), 1.47 (s, 3H), 1.46 (s, 3H) |
| 136 | 5-ethyl-3,7-di(pyridin-4-yl)thieno[2,3-d]pyridazin-4(5H)-one | 335/1.76 | 8.84 (d, J = 6.0 Hz, 2H), 8.71 (d, J = 5.6 Hz, 2H), 7.83 (dd, J = 4.0 Hz, 1.2 Hz, 2H), 7.67 (s, 1H), 7.53 (dd, J = 4.8 Hz, 1.2 Hz, 2H), 4.38 (q, J = 7.2 Hz, 2H), 1.48 (t, J = 7.2 Hz, 3H) |
| 137 | 5-(2-methylpropyl)-3,7-di(pyridin-4-yl)thieno[2,3-d]pyridazin-4(5H)-one | 363/1.93 | 8.83 (d, J = 6.0 Hz, 2H), 8.71 (d, J = 5.6 Hz, 2H), 7.82 (dd, J = 4.4 Hz, 1.6 Hz, 2H), 7.66 (s, 1H), 7.52 (dd, J = 4.8 Hz, 1.2 Hz, 2H), 4.16 (d, J = 7.6 Hz, 2H), 2.40-2.33 (m, 1H), 1.00 (d, J = 6.4 Hz, 6H) |
| 138 | 5-(2-methoxyethyl)-3,7-di(pyridin-4-yl)thieno[2,3-d]pyridazin-4(5H)-one | 365/1.67 | 8.83 (dd, J = 4.8 Hz, 1.6 Hz, 2H), 8.71 (d, J = 6.0 Hz, 2H), 7.82 (dd, J = 4.4 Hz, 1.6 Hz, 2H), 7.67 (s, 1H), 7.52 (dd, J = 4.4 Hz, 1.6 Hz, 2H), 4.53 (t, J = 5.6 Hz, 2H), 3.87 (t, J = 5.6 Hz, 2H), 3.38 (s, 3H) |
| 139 | 5-propyl-3,7-di(pyridin-4-yl)thieno[2,3-d]pyridazin-4(5H)-one | 349/1.84 | 8.83 (d, J = 6.0 Hz, 2H), 8.71 (d, J = 5.6 Hz, 2H), 7.82 (dd, J = 4.8 Hz, 1.6 Hz, 2H), 7.66 (s, 1H), 7.52 (dd, J = 4.8 Hz, 1.6 Hz, 2H), 4.29 (t, J = 7.6 Hz, 2H), 1.95-1.89 (m, 2H), 1.01 (t, J = 7.2 Hz, 3H) |

| EX. | Name | LC-MS: m/z (M + H)+/ R, [min] | 1H NMR (CDCl3, 400 MHz) δ: |
|---|---|---|---|
| 140 | 3-[4-oxo-3,7-di(pyridin-4-yl)thieno[2,3-d]pyridazin-5(4H)-yl]propanenitrile | 360/1.63 | 8.85 (d, J = 6.0 Hz, 2H), 8.73 (d, J = 5.6 Hz, 2H), 7.83 (dd, J = 4.4 Hz, 2.0 Hz, 2H), 7.73 (s, 1H), 7.50 (d, J = 4.4 Hz, 1.2 Hz, 2H), 4.61 (t, J = 6.4 Hz, 2H), 2.98 (t, J = 6.4 Hz, 2H) |
| 141 | 3,7-di(pyridin-4-yl)-5-(tetrahydrofuran-2-ylmethyl)thieno[2,3-d]pyridazin-4(5H)-one | 391/1.74 | 8.83 (d, J = 6.0 Hz, 2H), 8.70 (d, J = 5.6 Hz, 2H), 7.82 (dd, J = 4.8 Hz, 2.0 Hz, 2H), 7.66 (s, 1H), 7.51 (d, J = 6.0 Hz, 2H), 4.54-4.42 (m, 2H), 4.31 (m, 1H), 3.95 (q, J = 7.6 Hz, 1H), 3.79 (q, J = 8.0 Hz, 1H), 2.13-1.17 (m, 4H) |
| 142 | 3,7-di(pyridin-4-yl)-5-[2-(pyrrolidin-1-yl)ethyl]thieno[2,3-d]pyridazin-4(5H)-one | 404/1.67 | 8.83 (dd, J = 4.4 Hz, 1.6 Hz, 2H), 8.70 (dd, J = 4.4 Hz, 1.6 Hz, 2H), 7.81 (dd, J = 4.4 Hz, 2.0 Hz, 2H), 7.65 (s, 1H), 7.50 (dd, J = 4.4 Hz, 1.6 Hz, 2H), 4.51 (t, J = 6.8 Hz, 2H), 3.00 (s, 2H), 2.65 (s, 4H), 1.79 (s, 4H) |
| 143 | 5-[2-(dimethylamino)ethyl]-3,7-di(pyridin-4-yl)thieno[2,3-d]pyridazin-4(5H)-one | 378/1.63 | 8.83 (dd, J = 4.4 Hz, 1.6 Hz, 2H), 8.70 (dd, J = 4.4 Hz, 1.6 Hz, 2H), 7.81 (dd, J = 4.4 Hz, 1.2 Hz, 2H), 7.65 (s, 1H), 7.50 (dd, J = 4.4 Hz, 1.6 Hz, 2H), 4.49 (t, J = 6.4 Hz, 2H), 2.89 (s, 2H), 2.38 (s, 6H) |
| 144 | 5-[2-(morpholin-4-yl)ethyl]-3,7-di(pyridin-4-yl)thieno[2,3-d]pyridazin-4(5H)-one | 420/1.64 | 8.83 (dd, J = 4.8 Hz, 1.6 Hz, 2H), 8.70 (dd, J = 4.8 Hz, 1.6 Hz, 2H), 7.81 (dd, J = 4.0 Hz, 1.2 Hz, 2H), 7.66 (s, 1H), 7.50 (dd, J = 4.4 Hz, 1.6 Hz, 2H), 4.48 (t, J = 6.8 Hz, 2H), 3.68 (t, J = 4.8 Hz, 4H), 2.87 (t, J = 6.8 Hz, 2H), 2.58 (s, 4H) |

Example 145

5-ethyl-7-(pyridin-4-yl)-3-(pyrimidin-5-yl)thieno[2,3-d]pyridazin-4(5H)-one

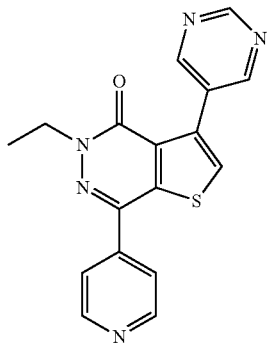 [SMILES: CCn1nc(-c2ccncc2)c2scc(-c3cncnc3)c2c1=O]

145.1 ethyl 2-(pyridin-4-carbonyl)-4-pyrimidin-5-yl-thiophene-3-carboxylate

The title compound was prepared in analogy to the method described in EXAMPLE I.4.

145.2 5-ethyl-7-(pyridin-4-yl)-3-(pyrimidin-5-yl)thieno[2,3-d]pyridazin-4(5H)-one The title compound was prepared from ethyl 2-(pyridin-4-carbonyl)-4-pyrimidin-5-yl-thiophene-3-carboxylate in analogy to the method described in EXAMPLE 131. Yield: 93% (81 mg). LC-MS: m/z 336.1 (M+H)+.

Example 146

5-(cyclopropylmethyl)-7-(pyridin-4-yl)-3-(pyrimidin-5-yl)thieno[2,3-d]pyridazin-4(5H)-one

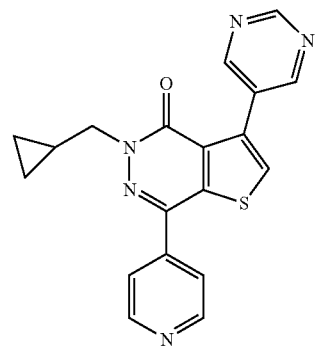 [SMILES: O=c1c2c(-c3cncnc3)csc2c(-c2ccncc2)nn1CC1CC1]

The title compound was prepared in analogy to the method described in EXAMPLE 145. Yield: 66.4% (50 mg). LC-MS: m/z 362.1 (M+H)+.

Example 147

5-methyl-3-(pyridin-4-yl)-7-(pyridin-3-ylmethoxy)thieno[2,3-d]pyridazin-4(5H)-one

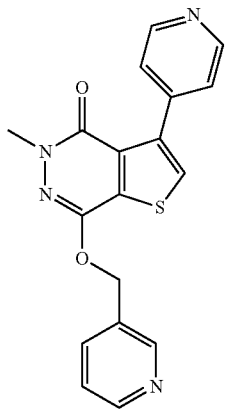 [SMILES: Cn1nc(OCc2cccnc2)c2scc(-c3ccncc3)c2c1=O]

A mixture of the product from EXAMPLE 1.2.5 (40.0 mg, 0.154 mmol), 3-(bromomethyl)pyridine hydrobromide (39.0 mg, 0.154 mmol) and $K_2CO_3$ (46.9 mg, 0.309 mmol) in DMF (1 mL) was stirred at RT for 2 h. After completion of the reaction, 10 mL water was added. The resulting solid was filtered off, washed with water and dried in the vacuum oven to give the title compound (14 mg, 23.3% yield) as pink-tinted solid. LC-MS: m/z 351.1 $(M+H)^+$, $R_t$: 1.15 min.

Biological Tests a) Measurement of PDE Activity

The recombinant PDE proteins are used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH 7.5, 10 mM $MgCl_2$, 0.1% bovine serum albumin) containing enzyme and substrate. The PDE enzymes concentration ranged from 10 pM-250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29° C. The reaction was stopped by addition of lysis buffer from the assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, $IC_{50}$ value of inhibitor can be obtained by plotting inhibitor concentration against PDE activity at that concentration. The results are shown in Table 1.

TABLE 1

| Ex. | $IC_{50}$ [1] |
|---|---|
| 2 | + |
| 3 | + |
| 6 | +++ |
| 11 | ++ |
| 14 | ++ |
| 50 | ++ |
| 52 | ++ |
| 54 | ++ |
| 55 | ++ |
| 56 | + |
| 58 | +++ |
| 59 | +++ |
| 60 | + |
| 61 | ++ |
| 62 | + |
| 63 | ++ |
| 64 | ++ |
| 67 | +++ |
| 69 | ++ |
| 70 | +++ |
| 71 | +++ |
| 72 | +++ |
| 73 | + |
| 75 | +++ |
| 76 | +++ |
| 78 | +++ |
| 81 | + |
| 82 | + |
| 83 | ++ |
| 84 | ++ |
| 85 | ++ |
| 86 | + |
| 88 | +++ |
| 89 | + |
| 90 | +++ |
| 91 | +++ |
| 92 | +++ |
| 94 | ++ |
| 95 | +++ |
| 96 | +++ |
| 97 | +++ |
| 99 | +++ |
| 100 | +++ |
| 102 | +++ |
| 104 | ++ |
| 105 | + |
| 107 | +++ |
| 110 | + |
| 111 | ++ |
| 112 | + |
| 113 | + |
| 114 | ++ |
| 115 | + |
| 116 | + |
| 117 | ++ |
| 119 | +++ |
| 120 | +++ |
| 121 | ++ |
| 123 | ++ |
| 124 | + |
| 126 | + |
| 127 | +++ |
| 128 | + |
| 130 | ++ |
| 131 | +++ |
| 135 | + |
| 136 | +++ |
| 139 | ++ |
| 140 | ++ |
| 145 | +++ |
| 146 | +++ |
| 147 | +++ |

Ex. Example  
[1] +++: $IC_{50} < 100$ nM  
++: 100 nM ≤ $IC_{50}$ ≤ 200 nM  
+: 200 nM < $IC_{50}$ ≤ 500 nM b) Determination of the Microsomal Half-Life:

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/mL) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/(content of microsomal protein in mg/mL)×1000 [mL/min/mg] (modified from references: Di, The Society for Biomoleculur Screening, 2003, 453-462; Obach, DMD, 1999 vol 27. N 11, 1350-1359). The results are shown in Table 2.

TABLE 2

| Ex. | Rat mCl[2)] | Human mCl[2)] |
|---|---|---|
| 2 | + | ++ |
| 3 | ++ | ++ |
| 4 | ++ | ++ |
| 5 | ++ | ++ |
| 6 | ++ | ++ |
| 7 | + | ++ |
| 8 | + | + |
| 10 | ++ | ++ |
| 11 | ++ | ++ |
| 12 | ++ | ++ |
| 13 | + | + |
| 14 | ++ | ++ |
| 15 | ○ | ++ |
| 23 | + | + |
| 24 | + | ○ |
| 25 | ++ | ++ |
| 26 | ○ | + |
| 27 | ++ | ++ |
| 30 | + | + |
| 31 | ++ | + |
| 32 | ++ | ++ |
| 33 | ○ | ++ |
| 34 | + | ++ |
| 35 | + | + |
| 36 | ++ | ++ |
| 37 | + | ++ |
| 39 | ++ | ++ |
| 40 | ++ | ++ |
| 41 | ++ | + |
| 42 | ++ | + |
| 43 | ++ | ++ |
| 47 | + | + |
| 48 | ++ | ++ |
| 49 | ++ | ++ |
| 50 | ++ | ++ |
| 52 | + | ++ |
| 53 | + | ++ |
| 54 | + | ++ |
| 55 | + | ++ |
| 57 | + | + |
| 58 | ++ | ++ |
| 59 | ++ | ++ |
| 61 | + | ++ |
| 62 | ++ | ++ |
| 63 | ++ | ++ |
| 64 | ++ | ++ |
| 65 | + | ○ |
| 66 | ++ | ++ |
| 67 | ++ | ++ |
| 69 | + | ++ |
| 70 | + | + |
| 73 | ++ | ++ |
| 75 | ++ | + |
| 76 | ++ | ++ |
| 77 | ++ | + |
| 78 | + | ++ |
| 79 | + | + |
| 80 | ++ | ++ |
| 81 | ++ | ++ |
| 82 | ++ | ++ |
| 83 | ++ | + |
| 84 | ○ | ++ |
| 85 | ++ | ++ |
| 86 | + | ++ |
| 88 | ++ | ++ |
| 89 | + | ++ |
| 91 | ++ | ++ |
| 92 | ++ | + |
| 94 | ++ | ++ |
| 95 | ++ | ++ |
| 96 | ++ | + |
| 97 | ++ | ++ |
| 98 | ++ | ++ |
| 99 | ++ | ++ |
| 101 | ++ | ++ |
| 123 | ○ | + |
| 124 | + | + |
| 125 | ++ | ++ |
| 127 | ++ | ++ |
| 128 | ++ | ++ |
| 129 | ++ | ++ |
| 130 | ++ | ++ |
| 131 | ++ | ++ |
| 132 | ++ | + |
| 134 | + | ○ |
| 135 | + | ++ |
| 136 | ++ | ++ |
| 139 | ++ | + |
| 141 | ++ | + |
| 145 | ++ | ++ |
| 146 | ++ | ++ |
| 147 | + | + |

Ex. Example
mCl mikrosomal clearance
[2)] ++: <100 µl min$^{-1}$ mg$^{-1}$
+: 100-220 µl min$^{-1}$ mg$^{-1}$
○ not avialable or >220 µl min$^{-1}$ mg$^{-1}$

We claim:
1. A compound of formula I

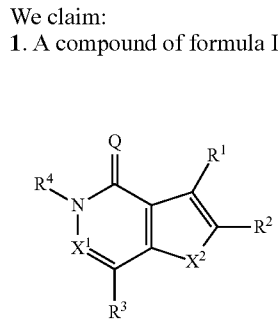

(I)

wherein
Q is O or S;
$X^1$ is N;
$X^2$ is O or S;
$R^1$ is a moiety $Y^1$-$Cyc^1$;
$R^2$ is selected from the group consisting of hydrogen, halogen, OH, $C_1$-$C_4$-alkyl, trimethylsilyl, hydroxy-$C_1$-$C_4$-alkyl, $C_1$-$C_4$-alkoxy-$C_1$-$C_4$-alkyl, $C_1$-$C_4$-alkoxy, $C_1$-$C_4$- alkoxy-$C_1$-$C_4$-alkoxy, $C_2$-$C_4$-alkenyloxy, $C_1$-$C_4$-fluoroalkyl, $C_1$-$C_4$-fluoroalkoxy, $C_3$-$C_7$-cycloalkyl, optionally substituted by 1, 2 or 3 methyl groups, fluorinated $C_3$-$C_7$-cycloalkyl, $C_3$-$C_7$-cycloalkyloxy, CN and $NR^{x1}R^{x2}$;

$R^{x1}$ and $R^{x2}$, independently of each other are selected from the group consisting of hydrogen, $C_1$-$C_4$-alkyl, $C_1$-$C_4$-fluoroalkyl, $C_1$-$C_4$-alkoxy-$C_1$-$C_4$-alkyl, hydroxy-$C_1$-$C_4$-alkyl, and $C_3$-$C_6$-cycloalkyl;

$R^3$ is a moiety $Y^3$-$Cyc^3$;

$R^4$ is unsubstituted $C_1$-$C_4$-alkyl, $C_1$-$C_4$-fluoroalkyl, $C_3$-$C_6$-cycloalkyl, fluorinated $C_3$-$C_7$-cycloalkyl, or $C_1$-$C_4$-alkyl which carries one or two radicals $R^{44}$;

$R^{44}$ is selected from the group consisting of $C_1$-$C_4$-alkoxy, $C_1$-$C_4$-fluoroalkoxy, CN, OH, $NR^{x3}R^{x4}$, $C_3$-$C_6$-cycloalkyl, $C_3$-$C_6$-cycloalkoxy, a 3- to 10-membered saturated, C-bound mono- or bicyclic heterocyclyl, and a 3- to 10-membered saturated, C-bound mono- or bicyclic heterocyclyloxy, where the last four groups of radicals are unsubstituted, partially or completely fluorinated and/or carry 1, 2, or 4 radicals selected from the group consisting of OH, $C_1$-$C_4$-alkyl, $C_1$-$C_4$-fluoroalkyl, $C_1$-$C_4$-alkoxy and $C_1$-$C_4$-fluoroalkoxy, and where C-bound heterocyclyl and C-bound heterocyclyloxy has 1, 2, 3 or 4 heteroatoms or heteroatom containing groups selected from the group consisting of O, N, S, SO and $SO_2$ as ring members;

where $R^{x3}$ and $R^{x4}$, independently of each other, are selected from the group consisting of hydrogen, $C_1$-$C_4$-alkyl, $C_1$-$C_4$-fluoroalkyl, $C_1$-$C_4$-alkoxy-$C_1$-$C_4$-alkyl, hydroxy-$C_1$-$C_4$-alkyl, and $C_3$-$C_6$-cycloalkyl, or $NR^{x3}R^{x4}$ is a saturated N-bound 3- to 7-membered, nitrogen heterocycle which may have 1, 2 or 3 further different or identical heteroatoms or heteroatom containing groups selected from the group consisting of O, N, S, SO and $SO_2$ as ring members and which may carry 1, 2, 3, 4, 5 or 6 substituents selected from the group consisting of halogen, OH, $C_1$-$C_4$-alkyl and $C_1$-$C_4$-alkoxy;

$Y^1$, $Y^3$ independently of each other are selected from the group consisting of a chemical bond, $CH_2$, O, O—$CH_2$, O—$CH(CH_3)$, O—$CH_2$—C(O)—NH, C(O)O, C(O), $NR^y$, $NR^y$—$CH_2$, $S(O)_2$—$NR^y$, C(O)—$NR^y$, S, S(O), $S(O)_2$, C(O)—O—$CH_2$, C(O)—$NR^y$—$CH_2$, 1,2-ethanediyl, 1,2-ethenediyl and 1,2-ethynediyl, where $R^y$ is selected from the group consisting of hydrogen, $C_1$-$C_4$-alkyl, $C_1$-$C_4$-alkylcarbonyl, $C_1$-$C_4$-alkylsulfonyl, and $C_1$-$C_4$-fluoroalkylsulfonyl;

$Cyc^1$, $Cyc^3$ independently of each other are selected from the group consisting of phenyl, naphthyl, $C_3$-$C_8$-cycloalkyl, 3- to 8-membered saturated or partially unsaturated heteromonocyclic radicals, saturated or partially unsaturated 7- to 10 membered heterobicyclic radicals, 5- or 6-membered monocyclic hetaryl, and 8- to 10 membered bicyclic hetaryl, where the saturated or partially unsaturated heteromonocyclic and heterobicyclic radicals have 1, 2, 3 or 4 heteroatoms or heteroatom containing groups as ring members, which are selected from the group consisting of O, S, SO, $SO_2$ and N, and where the 5- or 6-membered monocyclic hetaryl and the 8- to 10-membered bicyclic hetaryl have 1, 2, 3 or 4 heteroatoms as ring members, which are selected from the group consisting of O, S and N, where $C_3$-$C_8$-cycloalkyl, the saturated or partially unsaturated heteromonocyclic and heterobicyclic radicals are unsubstituted or carry 1, 2, 3, 4 or 5 radicals $R^{C1}$ or one radical $Y'$—$R^{C2}$ and 0, 1, 2, 3 or 4 radicals $R^{C1}$;

where phenyl, naphthyl, the saturated or partially unsaturated heteromonocyclic and heterobicyclic radicals and the mono and bicyclic heteroaromatic radicals are unsubstituted or carry 1, 2, 3, 4 or 5 radicals IC or one radical $Y'$—$R^{C2}$ and 0, 1, 2, 3 or 4 radicals $R^{C3}$; where $R^{C1}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^a$, Z—$C(O)OR^b$, Z—$C(O)NR_cR^d$, $NR^gSO_2R^h$, $S(O)_2NR^cR^d$ and Z—$NR^eR^f$, where $R^a$, $R^h$ independently of each other are selected from the group consisting of hydrogen, $C_1$-$C_4$-alkyl and $C_1$-$C_4$-fluoroalkyl, $R^b$, $R^g$ independently of each other are selected from the group consisting of hydrogen, $C_1$-$C_4$-alkyl, $C_2$-$C_4$-alkenyl and $C_1$-$C_4$-fluoroalkyl, $R^c$, $R^d$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, $R^e$, $R^f$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, Z is a covalent bond or $C_1$-$C_4$-alkanediyl, or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from the group consisting of O, S and N;

or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are selected from the group consisting of O, S and N, or two radicals $R^{C1}$ which are bound at the same carbon atom may form an oxygen atom, where the fused and the spiro radicals are unsubstituted or carry 1, 2, 3 or 4 radicals $R^{C4}$;

$Y'$ is a chemical bond, $CH_2$, O, O—$CH_2$, C(O), $S(O)_2$, $NR^{y'}$, $NR^{y'}$—$CH_2$ or $NR^{y'}$—$S(O)_2$, where $R^{y'}$ is selected from the group consisting of hydrogen, $C_1$-$C_4$-alkyl, $C_1$-$C_4$-alkylcarbonyl, $C_1$-$C_4$-alkylsulfonyl and $C_1$-$C_4$-fluoroalkylsulfonyl;

$R^{C2}$ is a carbocyclic or heterocyclic radical selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from the group consisting of O, S and N, and 5- or 6-membered heteroaromatic radicals, having 1, 2 or 3 heteroatoms as ring members, which are selected from the group consisting of O, S and N, where the carbocyclic and the heterocyclic radicals are unsubstituted or carry 1, 2, 3, 4 or 5 radicals $R^{C4}$;

$R^{C3}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-

$C_4$-alkyl, $C_1$-$C_4$-fluoroalkyl, $C_1$-$C_4$-fluoroalkoxy, $C_1$-$C_4$-alkylsulfonyl, C(O)R$^a$, Z—C(O)OR$^b$, Z—C(O)NR$^c$R$^d$, NR$^g$SO$_2$R$^h$, S(O)$_2$NR$^c$R$^d$ and Z—NR$^e$R$^f$, wherein R$^a$, R$^b$, R$^c$, R$^d$, R$^e$, R$^f$, R$^g$ and R$^h$ have the same meaning as defined above, or two radicals R$^{C3}$ which are bound at adjacent carbon atoms may form a saturated or partially unsaturated fused 5- or 6-membered carbocyclic radical or a saturated or partially unsaturated fused 5- or 6-membered heterocyclic radical having 1, 2 or 3 heteroatoms as ring members, which are selected from the group consisting of O, S and N, where the carbocyclic and the heterocyclic radical are unsubstituted or carry 1, 2, 3, 4 or 5 radicals R$^{C4}$;

R$^{C4}$ is selected from the group consisting of hydrogen, halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, C(O)R$^a$, benzyl, Z—C(O)OR$^b$, Z—C(O)NR$^c$R$^d$, S(O)$_2$NR$^c$R$^d$ and Z—NR$^e$R$^f$, where, Z, R$^a$, R$^b$, R$^c$, R$^d$, R$^e$ and R$^f$ are as defined above or two radicals R$^{C4}$ which are bound at the same atom may form an oxygen atom;

or an N-oxide, tautomer, or hydrate thereof, or a pharmaceutically acceptable salt thereof.

2. The compound of claim 1, where
$Y^1$, $Y^3$ independently of each other are selected from the group consisting of a chemical bond, $CH_2$, O, O—$CH_2$, C(O)O, C(O), NR$^y$, NR$^y$—$CH_2$, S(O)$_2$—NR$^y$, C(O)—NR$^y$, S, S(O), S(O)$_2$, C(O)—O—$CH_2$, C(O)—NR$^y$—$CH_2$, 1,2-ethanediyl, 1,2-ethenediyl and 1,2-ethynediyl, where R$^y$ is selected from the group consisting of hydrogen, $C_1$-$C_4$-alkyl, $C_1$-$C_4$-alkylcarbonyl, $C_1$-$C_4$-alkylsulfonyl, and $C_1$-$C_4$-fluoroalkylsulfonyl.

3. The compound of claim 1, where $X^2$ is S.

4. The compound of claim 1, where $Y^1$ is selected from the group consisting of a chemical bond, O, NH, $CH_2$, 1,2-ethenyl, ethynyl, C(O), NHCH$_2$, C(O)NH and C(O)NHCH$_2$.

5. The compound of claim 1, where Cyc$^1$ is selected from the group consisting of saturated 4-, 5-, 6-, 7- or 8-membered heteromonocycles and saturated 7-, 8-, 9- or 10-membered heterobicycles, where the heteromonocycles and the heterobicycles have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5 radicals R$^{C1}$ or one radical Y'—R$^{C2}$ and 0, 1, 2, 3 or 4 radicals R$^{C1}$, where R$^{C1}$, R$^{C2}$ and Y' are as defined in claim 1.

6. The compound of claim 5, where R$^1$ is selected from the group consisting of 1-piperidinyl, 4,4-difluoro-1-piperidinyl, 4-hydroxylpiperidin-1-yl, 4-piperidinyl, 1-methyl-4-piperidinyl, 1-piperazinyl, 4-methyl-1-piperazinyl, 4-(tert.-butyloxycarbonyl) piperazin-1-yl, 1-piperazinylmethyl, 4-methyl-1-piperazinylmethyl, 1-piperazinylcarbonyl, 4-methyl-1-piperazinylcarbonyl, morpholin-4-yl, morpholin-4-ylmethyl, morpholin-4-ylcarbonyl, azepane-1-yl, 1,4-oxazepan-4-yl, thiomorpholin-4-yl, 1-oxothiomorpholin-4-yl, N-(oxetan-3-yl)amino, 1,1-dioxothiomorpholin-4-yl and oxetan-3-ylamino.

7. The compound of claim 1, where Cyc$^1$ is selected from the group consisting of phenyl, 5- or 6 membered monocyclic hetaryl, and 9- or 10 membered bicyclic hetaryl, where hetaryl has one heteroatom, selected from the group consisting of O, S and N as ring member and optionally one or two further nitrogen atoms as ring members, where phenyl and the hetaryl radical are unsubstituted or either carry, independently of each other, 1, 2, 3, 4 or 5 radicals R$^{C3}$ or one radical Y'—R$^{C2}$ and 0, 1, 2, 3 or 4 radicals R$^{C3}$.

8. The compound of claim 7, where R$^1$ is selected from the group consisting of phenyl, 5- or 6-membered monocyclic hetaryl, which is selected from the group consisting of pyridyl, pyrimidinyl, furyl, thienyl, pyrrolyl, imidazolyl, pyrazolyl, oxazolyl and thiazolyl, and 9- or 10-membered bicyclic hetaryl, which is selected from the group consisting of indolyl, quinolinyl, isoquinolinyl, quinazolinyl, 1,3-benzoxazolyl, 1,3-benzothiazolyl, benzimidazolyl, benzotriazolyl, benzopyrazolyl, benzothienyl and benzofuryl, where phenyl, monocyclic and bicyclic hetaryl are unsubstituted or carry 1, 2 or 3 radicals R$^{C3}$ which are selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, C(O)NH$_2$ and NH$_2$, or carry one radical Y'—R$^{C2}$, where Y' is a bond, $CH_2$ or C(O) and R$^{C2}$ is phenyl, pyridyl, 1-imidazolyl, 1-pyrazolyl, 1-piperidinyl, 1-piperazinyl, 4-methyl-1-piperazinyl or 4-morpholinyl, or, if R$^1$ is phenyl, two radicals R$^{C3}$ which are bound to adjacent carbon atoms, together with the phenyl ring to which they are bound, form a bicyclic heterocyclic radical, which is selected from the group consisting of 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

9. The compound of claim 1, where R$^1$ is selected from the group consisting of 4-pyridyl, 3-pyridyl, pyrimidin-5-yl, 3-methoxyphenyl, 4-morpholinyl, morpholin-4-ylmethyl, oxetan-3-ylamino, 3-(1H-pyrazol-1-yl)phenyl, pyridazin-4-yl, 2-methylpyrimidin-5-yl, 2-hydroxyphenyl and 4-hydroxyphenyl.

10. The compound of claim 1, where R$^2$ is selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, and fluorinated cyclopropyl.

11. The compound as claimed in claim 10, where R$^2$ is hydrogen.

12. The compound of claim 1, where $Y^3$ is selected from the group consisting of a chemical bond, O, NH, $CH_2$, C(O), OCH$_2$, NHCH$_2$, C(O)NH and C(O)NHCH$_2$.

13. The compound as claimed in claim 1, where Cyc$^3$ is selected from the group consisting of $C_3$-$C_7$-cycloalkyl, saturated 4-, 5-, 6-, 7- or 8-membered heteromonocycles and saturated 7-, 8-, 9- or 10-membered heterobicycles, where the heteromonocycles and the heterobicycles have one nitrogen or oxygen atom as ring member and may have one further heteroatom or heteroatom group as ring member, which is selected from the group consisting of O, S, S(=O), S(=O)$_2$ and N, where $C_3$-$C_7$-cycloalkyl, the saturated heteromonocycle and the saturated heterobicycle are unsubstituted or carry 1, 2, 3, 4 or 5 radicals R$^{C1}$ or one radical Y'—R$^{C2}$ and 0, 1, 2, 3 or 4 radicals R$^{C1}$, where R$^{C1}$, R$^{C2}$ and Y' are as defined in claim 1.

14. The compound of claim 12, where R$^3$ is selected from the group consisting of cyclohexyloxy, cyclohexylmethyloxy, 4,4-difluoro-1-cyclohexyloxy, 4,4-difluoro-1-cyclohexylmethyloxy, 1-piperidinyl, 4,4-difluoro-1-piperidinyl, 4-hydroxylpiperidin-1-yl, 4-piperidinyl, 1-methyl-4-piperidinyl, 1-piperidinylmethyl, 4,4-difluoro-1-piperidinylmethyl, 4-hydroxylpiperidin-1-ylmethyl, 4-piperidinylmethyloxy, 1-methyl-4-piperidinylmethyloxy, 1-piperazinyl, 4-methyl-1-piperazinyl, 4-(tert.-butyloxycarbonyl)piperazin-1-yl, 1-piperazinylmethyl, 4-methyl-1-piperazinylmethyl, 1-piperazinylmethyloxy, 4-methyl-1-piperazinylmethyloxy, 1-piperazinylcarbonyl, 4-methyl-1-piperazinylcarbonyl, morpholin-4-yl, morpholin-4-ylmethyl, morpholin-4-ylcarbonyl, azepane-1-yl, 1,4-oxazepan-4-yl, thiomorpholin-4-yl, 1-oxothiomorpholin-4-yl, N-(oxetan-3-yl)amino, 1,1-dioxothiomorpholin-4-yl and oxetan-3-ylamino.

15. The compound of claim 1, where $Cyc^3$ is selected from the group consisting of phenyl, 5- or 6 membered monocyclic hetaryl, and 9- or 10 membered bicyclic hetaryl, where hetaryl has one heteroatom, selected from O, S and N as ring member and optionally one or two further nitrogen atoms as ring members, where phenyl and the hetaryl radical are unsubstituted or either carry, independently of each other, 1, 2, 3, 4 or 5 radicals $R^{C3}$ or one radical Y'—$R^{c2}$ and 0, 1, 2, 3 or 4 radicals $R^{C3}$.

16. The compound as claimed in claim 15, where $Y^3$ is a chemical bond, O, NH, $OCH_2$, $OCH(CH_3)$ or $NHCH_2$ and $Cyc^3$ is selected from the group consisting of phenyl, 5- or 6-membered monocyclic hetaryl, which is selected from the group consisting of pyridyl, pyrimidinyl, furyl, thienyl, pyrrolyl, imidazolyl, pyrazolyl, oxazolyl and thiazolyl, and 9- or 10-membered bicyclic hetaryl, which is selected from the group consisting of indolyl, quinolinyl, isoquinolinyl, quinazolinyl, 1,3-benzoxazolyl, 1,3-benzothiazolyl, benzimidazolyl, benzotriazolyl, benzopyrazolyl, benzothienyl and benzofuryl, where phenyl and hetaryl are unsubstituted or carry 1, 2 or 3 radicals $R^{C3}$ which are selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, $C(O)NH_2$ and $NH_2$, or carry one radical Y'—$R^{C2}$, where Y' is a bond, $CH_2$ or C(O) and $R^{C2}$ is phenyl, pyridyl, pyrimidinyl, 1-pyrazolyl, 1-imidazolyl, 1-piperidinyl, 1-piperazinyl, 4-methyl-1-piperazinyl or 4-morpholinyl, or, if $Cyc^3$ is phenyl, two radicals $R^{C3}$ which are bound to adjacent carbon atoms, together with the phenyl ring to which they are bound, form a bicyclic heterocyclic radical, which is selected from the group consisting of 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

17. The compound of claim 1, where $R^3$ is selected from the group consisting of 4-pyridyl, 3,4-dimethoxyphenyl, 1-methyl-1H-imidzaol-4-yl, benzylamino, 1-(2,2,2-trifluoroethyl)-1H-pyrazol-4-yl, 1,3-benzthiazol-2-ylmethoxy, 3,5-dimethoxybenzyloxy, 3,4-dimethoxybenzyloxy, 3-cyanobenzyloxy, 4-cyanobenzyloxy, 3,5-dimethoxyphenoxy, 3,4-dimethoxyphenoxy, 3-cyanophenoxy, 4-cyanophenoxy, 1-(2-methoxyethyl)-1-H-pyrazol-4-yl, 5-methoxypyridin-3-yl, 3-(difluoromethoxy)benzyloxy, 4-(difluoromethoxy)benzyloxy, 3-hydroxyphenyl, 1,3-benzoxazol-6-yl, pyridin-3-ylmethoxy, pyridin-2-ylmethoxy, 2-fluoropyridin-4-yl, 3-(methoxycarbonyl)benzyloxy, 3-(aminocarbonyl)benzyloxy, 2-chloro-6-methylpyridin-3-yloxy, thiazol-2-ylmethoxy, 1-methylbenzimidazol-2-ylmethoxy, 1-piperidinyl, 4-morpholinyl and 4-methypiperazin-1-yl.

18. The compound of claim 1, where $R^4$ is selected from the group consisting of $C_1$-$C_3$-alkyl, $C_1$-$C_2$-fluoroalkyl, and $C_1$-$C_2$-alkyl, which carries one of the radicals $R^{44}$, where $R^{44}$ is selected from the group consisting of methoxy, ethoxy, CN, OH, $C_3$-$C_5$-cycloalkyl, and $NR^{x3}R^{x4}$, where $R^{x3}$ and $R^{x4}$ are independently of each other selected from the group consisting of hydrogen, $C_1$-$C_2$-alkyl, hydroxyl-$C_1$-$C_2$-alkyl, and $C_1$-$C_2$-alkoxy-$C_1$-$C_2$-alkyl, or $NR^{x3}R^{x4}$ is 1-piperidinyl, 1-pyrrolidinyl, 4-morpholinyl, 1-piperazinyl or 4-methyl-1-piperazinyl.

19. The compound of claim 18, where $R^4$ is selected from the group consisting of methyl, ethyl, 2,2,2-trifluoroethyl and cyclopropylmethyl.

20. The compound of claim 1, where Q is O.

21. The compound as claimed in claim 1, which is selected from the group consisting of
5-methyl-3-(oxetan-3-ylamino)-7-(pyridin-4-yl)thieno[2,3-d]pyridazin-4(5H)-one;
5-methyl-3-(morpholin-4-yl)-7-(pyridin-4-yl)thieno[2,3-d]pyridazin-4(5H)-one;
3-(4-hydroxypiperidin-1-yl)-5-methyl-7-(pyridin-4-yl)thieno[2,3-d]pyridazin-4(5H)-one;
tert-butyl 4-[5-methyl-4-oxo-7-(pyridin-4-yl)-4,5-dihydrothieno[2,3-d]pyridazin-3-yl]piperazine-1-carboxylate;
5-methyl-7-(pyridin-4-yl)-3-(pyrimidin-5-yl)thieno[2,3-d]pyridazin-4(5H)-one;
5-methyl-3-(pyridazin-4-yl)-7-(pyridin-4-yl)thieno[2,3-d]pyridazin-4(5H)-one;
3-(4-fluorophenyl)-5-methyl-7-(pyridin-4-yl)thieno[2,3-d]pyridazin-4(5H)-one;
3-[5-methyl-4-oxo-7-(pyridin-4-yl)-4,5-dihydrothieno[2,3-d]pyridazin-3-yl]benzonitrile;
3-(2-methoxypyrimidin-5-yl)-5-methyl-7-(pyridin-4-yl)thieno[2,3-d]pyridazin-4(5H)-one;
5-methyl-3-(piperazin-1-yl)-7-(pyridin-4-yl)thieno[2,3-d]pyridazin-4(5H)-one;
5-methyl-3-(morpholin-4-ylmethyl)-7-(pyridin-4-yl)thieno[2,3-d]pyridazin-4(5H)-one;
5-methyl-3-(pyridin-3-yl)-7-(pyridin-4-yl)thieno[2,3-d]pyridazin-4(5H)-one;
3-(1H-indol-5-yl)-5-methyl-7-(pyridin-4-yl)thieno[2,3-d]pyridazin-4(5H)-one;
5-methyl-3-[(E)-2-phenylethenyl]-7-(pyridin-4-yl)thieno[2,3-d]pyridazin-4(5H)-one;
5-methyl-7-(pyridin-4-yl)-3-(pyridin-3-ylethynyl)thieno[2,3-d]pyridazin-4(5H)-one;
N-benzyl-5-methyl-4-oxo-7-(pyridin-4-yl)-4,5-dihydrothieno[2,3-d]pyridazine-3-carboxamide;
5-methyl-3-[(4-methylpiperazin-1-yl)carbonyl]-7-(pyridin-4-yl) thieno[2,3-d]pyridazin-4(5H)-one;
N-benzyl-N-ethyl-5-methyl-4-oxo-7-(pyridin-4-yl)-4,5-dihydrothieno[2,3-d]pyridazine-3-carboxamide;
3-(4-methoxyphenyl)-5-methyl-7-(pyridin-4-yl)thieno[2,3-d]pyridazin-4(5H)-one;
3-(1-benzothiophen-2-yl)-5-methyl-7-(pyridin-4-yl)thieno[2,3-d]pyridazin-4(5H)-one;
5-methyl-3-[3-(1H-pyrazol-1-yl)phenyl]-7-(pyridin-4-yl)thieno[2,3-d]pyridazin-4(5H)-one;
4-[5-methyl-4-oxo-7-(pyridin-4-yl)-4,5-dihydrothieno[2,3-d]pyridazin-3-yl]benzonitrile;
3-(1-benzothiophen-3-yl)-5-methyl-7-(pyridin-4-yl)thieno[2,3-d]pyridazin-4(5H)-one;
3-(6-fluoropyridin-3-yl)-5-methyl-7-(pyridin-4-yl)thieno[2,3-d]pyridazin-4(5H)-one;
3-(4-hydroxyphenyl)-5-methyl-7-(pyridin-4-yl)thieno[2,3-d]pyridazin-4 (5H)-one;
3-[5-methyl-4-oxo-7-(pyridin-4-yl)-4,5-dihydrothieno[2,3-d]pyridazin-3-yl]benzonitrile;
3-(3-methoxyphenyl)-5-methyl-7-(pyridin-4-yl)thieno[2,3-d]pyridazin-4(5H)-one;

3-(3-fluorophenyl)-5-methyl-7-(pyridin-4-yl)thieno[2,3-d]pyridazin-4(5H)-one;

5-methyl-3-[3-(morpholin-4-ylcarbonyl)phenyl]-7-(pyridin-4-yl)thieno[2,3-d]pyridazin-4(5H)-one;

N-{4-[5-methyl-4-oxo-7-(pyridin-4-yl)-4,5-dihydrothieno[2,3-d]pyridazin-3-yl]phenyl}methane sulfonamide;

5-methyl-7-(pyridin-4-yl)-3-(thiophen-3-yl) thieno[2,3-d]pyridazin-4 (5H)-one;

3-(2,3-dihydro-1-benzofuran-5-yl)-5-methyl-7-(pyridin-4-yl)thieno[2,3-d]pyridazin-4(5H)-one;

3-(2-fluorophenyl)-5-methyl-7-(pyridin-4-yl)thieno[2,3-d]pyridazin-4(5H)-one;

5-methyl-3-(1-methyl-1H-pyrazol-4-yl)-7-(pyridin-4-yl)thieno[2,3-d]pyridazin-4(5H)-one;

3-[4-(dimethylamino)phenyl]-5-methyl-7-(pyridin-4-yl)thieno[2,3-d]pyridazin-4 (5H)-one;

3-(2-methoxyphenyl)-5-methyl-7-(pyridin-4-yl)thieno[2,3-d]pyridazin-4(5H)-one;

N-cyclopropyl-4-[5-methyl-4-oxo-7-(pyridin-4-yl)-4,5-dihydrothieno[2,3-d]pyridazin-3-yl]benzamide;

3-(1-benzyl-1H-pyrazol-4-yl)-5-methyl-7-(pyridin-4-yl)thieno[2,3-d]pyridazin-4(5H)-one;

5-methyl-3-{3-[(4-methylpiperazin-1-yl)methyl]phenyl}-7-(pyridin-4-yl) thieno[2,3-d]pyridazin-4(5H)-one;

5-methyl-3-{4-[(4-methylpiperazin-1-yl)methyl]phenyl}-7-(pyridin-4-yl) thieno[2,3-d]pyridazin-4(5H)-one;

3-(2-hydroxyphenyl)-5-methyl-7-(pyridin-4-yl)thieno[2,3-d]pyridazin-4 (5H)-one;

5-methyl-3-(4-methylphenyl)-7-(pyridin-4-yl)thieno[2,3-d]pyridazin-4(5H)-one;

3-(1,3-benzodioxol-5-yl)-5-methyl-7-(pyridin-4-yl)thieno[2,3-d]pyridazin-4(5H)-one;

5-methyl-7-(piperidin-1-yl)-3-(pyridin-4-yl)thieno[2,3-d]pyridazin-4(5H)-one;

3-(4-fluorophenyl)-5-methyl-7-(pyridin-4-yl)thieno[2,3-d]pyridazin-4(5H)-one;

5-methyl-7-(4-methylpiperazin-1-yl)-3-(pyridin-4-yl)thieno[2,3-d]pyridazin-4(5H)-one;

7-(benzylamino)-5-methyl-3-(pyridin-4-yl)thieno[2,3-d]pyridazin-4 (5H)-one;

7-(furan-2-ylmethoxy)-5-methyl-3-(pyridin-4-yl)thieno[2,3-d]pyridazin-4 (5H)-one;

7-(cyclohexyloxy)-5-methyl-3-(pyridin-4-yl) thieno[2,3-d]pyridazin-4(5H)-one;

7-(benzyloxy)-5-methyl-3-(pyridin-4-yl)thieno[2,3-d]pyridazin-4(5H)-one;

5-methyl-3-(pyridin-4-yl)-7-(pyridin-2-ylmethoxy)thieno[2,3-d]pyridazin-4(5H)-one;

5-methyl-7-[(1-methyl-1H-imidazol-2-yl)methoxy]-3-(pyridin-4-yl) thieno[2,3-d]pyridazin-4(5H)-one;

7-(cyclohexylmethoxy)-5-methyl-3-(pyridin-4-yl)thieno[2,3-d]pyridazin-4 (5H)-one;

5-methyl-3-(pyridin-4-yl)-7-(1,3-thiazol-2-ylmethoxy)thieno[2,3-d]pyridazin-4(5H)-one;

3-({[5-methyl-4-oxo-3-(pyridin-4-yl)-4,5-dihydrothieno[2,3-d]pyridazin-7-yl]oxy}methyl) benzonitrile;

7-(2,3-dihydro-1H-inden-2-yloxy)-5-methyl-3-(pyridin-4-yl)thieno[2,3-d]pyridazin-4(5H)-one;

7-[(3-methoxybenzyl)oxy]-5-methyl-3-(pyridin-4-yl)thieno[2,3-d]pyridazin-4(5H)-one;

7-[(4-chlorobenzyl)oxy]-5-methyl-3-(pyridin-4-yl) thieno[2,3-d]pyridazin-4(5H)-one;

7-(1-benzofuran-3-ylmethoxy)-5-methyl-3-(pyridin-4-yl)thieno[2,3-d]pyridazin-4(5H)-one;

7-(1-benzofuran-7-ylmethoxy)-5-methyl-3-(pyridin-4-yl)thieno[2,3-d]pyridazin-4(5H)-one;

5-methyl-7-{[3-(propan-2-yl)benzyl]oxy}-3-(pyridin-4-yl)thieno[2,3-d]pyridazin-4(5H)-one;

7-[(4,4-difluorocyclohexyl)methoxy]-5-methyl-3-(pyridin-4-yl) thieno[2,3-d]pyridazin-4(5H)-one;

3-({[5-methyl-4-oxo-3-(pyridin-4-yl)-4,5-dihydrothieno[2,3-d]pyridazin-7-yl]oxy}methyl)benzamide;

3-({[5-methyl-4-oxo-3-(pyridin-4-yl)-4,5-dihydrothieno[2,3-d]pyridazin-7-yl]oxy}methyl)benzamide;

7-(1,3-benzodioxol-5-ylmethoxy)-5-methyl-3-(pyridin-4-yl)thieno[2,3-d]pyridazin-4(5H)-one;

5-methyl-7-[(1-methyl-1H-benzimidazol-2-yl)methoxy]-3-(pyridin-4-yl)thieno[2,3-d]pyridazin-4(5H)-one;

7-(1,3-benzothiazol-2-ylmethoxy)-5-methyl-3-(pyridin-4-yl)thieno[2,3-d]pyridazin-4(5H)-one;

methyl 3-({[5-methyl-4-oxo-3-(pyridin-4-yl)-4,5-dihydrothieno[2,3-d]pyridazin-7-yl]oxy}methyl)benzoate;

5-methyl-7-{[3-(propan-2-yloxy)benzyl]oxy}-3-(pyridin-4-yl)thieno[2,3-d]pyridazin-4(5H)-one;

N-(2-hydroxyphenyl)-2-{[5-methyl-4-oxo-3-(pyridin-4-yl)-4,5-dihydrothieno[2,3-d]pyridazin-7-yl]oxy}acetamide;

7-[(3,5-dimethoxybenzyl)oxy]-5-methyl-3-(pyridin-4-yl)thieno[2,3-d]pyridazin-4(5H)-one;

7-{[3-(difluoromethoxy)benzyl]oxy}-5-methyl-3-(pyridin-4-yl) thieno[2,3-d]pyridazin-4(5H)-one;

7-[(3,4-dichlorobenzyl)oxy]-5-methyl-3-(pyridin-4-yl) thieno[2,3-d]pyridazin-4(5H)-one;

5-methyl-7-[1-(1-methyl-1H-benzimidazol-2-yl)ethoxy]-3-(pyridin-4-yl) thieno[2,3-d]pyridazin-4(5H)-one;

tert-butyl 4-({[5-methyl-4-oxo-3-(pyridin-4-yl)-4,5-dihydrothieno[2,3-d]pyridazin-7-yl]oxy}methyl)piperidine-1-carboxylate;

tert-butyl 5-({[5-methyl-4-oxo-3-(pyridin-4-yl)-4,5-dihydrothieno[2,3-d]pyridazin-7-yl]oxy}methyl)-1,3-dihydro-2H-isoindole-2-carboxylate;

5-methyl-7-phenoxy-3-(pyridin-4-yl)thieno[2,3-d]pyridazin-4(5H)-one;

5-methyl-3-(pyridin-4-yl)-7-(pyridin-3-yloxy)thieno[2,3-d]pyridazin-4 (5H)-one;

2-{[5-methyl-4-oxo-3-(pyridin-4-yl)-4,5-dihydrothieno[2,3-d]pyridazin-7-yl]oxy}benzonitrile;

7-(2-methoxyphenoxy)-5-methyl-3-(pyridin-4-yl)thieno[2,3-d]pyridazin-4 (5H)-one;

7-(3-methoxyphenoxy)-5-methyl-3-(pyridin-4-yl)thieno[2,3-d]pyridazin-4 (5H)-one;

7-(4-methoxyphenoxy)-5-methyl-3-(pyridin-4-yl)thieno[2,3-d]pyridazin-4 (5H)-one;

7-(3-hydroxy-5-methoxypyridin-2-yl)-5-methyl-3-(pyridin-4-yl)thieno[2,3-d]pyridazin-4(5H)-one;

7-[(5-methoxypyridin-3-yl)oxy]-5-methyl-3-(pyridin-4-yl)thieno[2,3-d]pyridazin-4(5H)-one;

7-(1,3-benzodioxol-5-yloxy)-5-methyl-3-(pyridin-4-yl)thieno[2,3-d]pyridazin-4(5H)-one;

7-[(2-chloro-5-methylpyridin-3-yl)oxy]-5-methyl-3-(pyridin-4-yl)thieno[2,3-d]pyridazin-4(5H)-one;

7-(3,4-dimethoxyphenoxy)-5-methyl-3-(pyridin-4-yl)thieno[2,3-d]pyridazin-4(5H)-one;

7-(3,5-dimethoxyphenoxy)-5-methyl-3-(pyridin-4-yl)thieno[2,3-d]pyridazin-4(5H)-one;

7-{[6-(benzyloxy)pyridin-3-yl]oxy}-5-methyl-3-(pyridin-4-yl) thieno[2,3-d]pyridazin-4(5H)-one;

3-[5-methyl-4-oxo-3-(pyridin-4-yl)-4,5-dihydrothieno[2,3-d]pyridazin-7-yl]benzonitrile;

4-[5-methyl-4-oxo-3-(pyridin-4-yl)-4,5-dihydrothieno[2,3-d]pyridazin-7-yl]benzonitrile;

7-(4-methoxyphenyl)-5-methyl-3-(pyridin-4-yl)thieno[2,3-d]pyridazin-4(5H)-one;

7-(1,3-benzoxazol-6-yl)-5-methyl-3-(pyridin-4-yl)thieno[2,3-d]pyridazin-4(5H)-one;
2-[5-methyl-4-oxo-3-(pyridin-4-yl)-4,5-dihydrothieno[2,3-d]pyridazin-7-yl]benzamide;
7-[1-(2-methoxyethyl)-1H-pyrazol-4-yl]-5-methyl-3-(pyridin-4-yl)thieno[2,3-d]pyridazin-4(5H)-one;
5-methyl-3-(pyridin-4-yl)-7-[1-(2,2,2-trifluoroethyl)-1H-pyrazol-4-yl]thieno[2,3-d]pyridazin-4(5H)-one;
5-methyl-3-(pyridin-4-yl)-7-[4-(trifluoromethoxy)phenyl]thieno[2,3-d]pyridazin-4(5H)-one;
7-(3,4-dimethoxyphenyl)-5-methyl-3-(pyridin-4-yl)thieno[2,3-d]pyridazin-4(5H)-one;
7-(4-fluorophenyl)-5-methyl-3-(pyridin-4-yl) thieno[2,3-d]pyridazin-4(5H)-one;
7-(2-fluoropyridin-4-yl)-5-methyl-3-(pyridin-4-yl) thieno[2,3-d]pyridazin-4(5H)-one;
7-(3-chlorophenyl)-5-methyl-3-(pyridin-4-yl)thieno[2,3-d]pyridazin-4(5H)-one;
7-(biphenyl-4-yl)-5-methyl-3-(pyridin-4-yl)thieno[2,3-d]pyridazin-4 (5H)-one;
7-(3-hydroxyphenyl)-5-methyl-3-(pyridin-4-yl)thieno[2,3-d]pyridazin-4 (5H)-one;
5-methyl-7-(4-phenoxyphenyl)-3-(pyridin-4-yl) thieno[2,3-d]pyridazin-4(5H)-one;
7-(2,4-dichlorophenyl)-5-methyl-3-(pyridin-4-yl) thieno[2,3-d]pyridazin-4(5H)-one;
7-(4-chlorophenyl)-5-methyl-3-(pyridin-4-yl)thieno[2,3-d]pyridazin-4(5H)-one;
7-(3,5-dimethoxyphenyl)-5-methyl-3-(pyridin-4-yl) thieno[2,3-d]pyridazin-4(5H)-one;
5-methyl-3-(pyridin-4-yl)-7-[3-(trifluoromethoxy)phenyl]thieno[2,3-d]pyridazin-4(5H)-one;
7-(2-methoxyphenyl)-5-methyl-3-(pyridin-4-yl)thieno[2,3-d]pyridazin-4(5H)-one;
5-methyl-3-(pyridin-4-yl)-7-[3-(trifluoromethyl)phenyl] thieno[2,3-d]pyridazin-4(5H)-one;
7-(2-fluorophenyl)-5-methyl-3-(pyridin-4-yl) thieno[2,3-d]pyridazin-4(5H)-one;
7-(3-fluorophenyl)-5-methyl-3-(pyridin-4-yl) thieno[2,3-d]pyridazin-4(5H)-one;
5-methyl-3-(pyridin-4-yl)-7-[4-(trifluoromethyl)phenyl] thieno[2,3-d]pyridazin-4(5H)-one;
7-(4-hydroxyphenyl)-5-methyl-3-(pyridin-4-yl)thieno[2,3-d]pyridazin-4 (5H)-one;
7-[3-(dimethylamino)phenyl]-5-methyl-3-(pyridin-4-yl) thieno[2,3-d]pyridazin-4 (5H)-one;
5-methyl-7-(2-methylpyridin-4-yl)-3-(pyridin-4-yl) thieno[2,3-d]pyridazin-4(5H)-one;
5-methyl-7-(4-methylphenyl)-3-(pyridin-4-yl)thieno[2,3-d]pyridazin-4 (5H)-one;
5-methyl-3-(pyridin-4-yl)-7-[4-(trifluoromethoxy)phenyl]thieno[2,3-d]pyridazin-4(5H)-one;
7-(3-methoxyphenyl)-5-methyl-3-(pyridin-4-yl)thieno[2,3-d]pyridazin-4(5H)-one;
7-(1,3-benzodioxol-5-yl)-5-methyl-3-(pyridin-4-yl) thieno[2,3-d]pyridazin-4(5H)-one;
5-methyl-7-(piperidin-4-ylmethoxy)-3-(pyridin-4-yl) thieno[2,3-d]pyridazin-4(5H)-one;
7-(2,3-dihydro-1H-isoindol-5-ylmethoxy)-5-methyl-3-(pyridin-4-yl) thieno[2,3-d]pyridazin-4(5H)-one;
3-[4-oxo-7-(pyridin-4-yl)-5-(2,2,2-trifluoroethyl)-4,5-dihydrothieno[2,3-d]pyridazin-3-yl]benzonitrile;
3-(2-methylpyrimidin-5-yl)-7-(pyridin-4-yl)-5-(2,2,2-trifluoroethyl) thieno[2,3-d]pyridazin-4(5H)-one;
3-[4-oxo-7-(pyridin-4-yl)-5-(2,2,2-trifluoroethyl)-4,5-dihydrothieno[2,3-d]pyridazin-3-yl]benzonitrile;
5-methyl-3,7-di(pyridin-4-yl) thieno[2,3-d]pyridazin-4(5H)-one;
3,7-di(pyridin-4-yl)-5-(2,2,2-trifluoroethyl) thieno[2,3-d]pyridazin-4(5H)-one;
5-tert-butyl-3,7-di(pyridin-4-yl) thieno[2,3-d]pyridazin-4(5H)-one;
5-cyclohexyl-3,7-di(pyridin-4-yl) thieno[2,3-d]pyridazin-4(5H)-one;
5-cyclopentyl-3,7-di(pyridin-4-yl) thieno[2,3-d]pyridazin-4(5H)-one;
5-(propan-2-yl)-3,7-di(pyridin-4-yl) thieno[2,3-d]pyridazin-4(5H)-one;
5-ethyl-3,7-di(pyridin-4-yl) thieno[2,3-d]pyridazin-4(5H)-one;
5-(2-methylpropyl)-3,7-di(pyridin-4-yl) thieno[2,3-d]pyridazin-4 (5H)-one;
5-(2-methoxyethyl)-3,7-di(pyridin-4-yl)thieno[2,3-d]pyridazin-4(5H)-one;
5-propyl-3,7-di(pyridin-4-yl)thieno[2,3-d]pyridazin-4 (5H)-one;
3-[4-oxo-3,7-di(pyridin-4-yl)thieno[2,3-d]pyridazin-5 (4H)-yl]propanenitrile;
3,7-di(pyridin-4-yl)-5-(tetrahydrofuran-2-ylmethyl) thieno[2,3-d]pyridazin-4(5H)-one;
3,7-di(pyridin-4-yl)-5-[2-(pyrrolidin-1-yl)ethyl]thieno[2,3-d]pyridazin-4(5H)-one;
5-[2-(dimethylamino)ethyl]-3,7-di(pyridin-4-yl)thieno[2,3-d]pyridazin-4(5H)-one;
5-[2-(morpholin-4-yl)ethyl]-3,7-di(pyridin-4-yl)thieno[2,3-d]pyridazin-4(5H)-one;
5-ethyl-7-(pyridin-4-yl)-3-(pyrimidin-5-yl)thieno[2,3-d]pyridazin-4(5H)-one;
5-(cyclopropylmethyl)-7-(pyridin-4-yl)-3-(pyrimidin-5-yl)thieno[2,3-d]pyridazin-4(5H)-one; and
5-methyl-3-(pyridin-4-yl)-7-(pyridin-3-ylmethoxy)thieno[2,3-d]pyridazin-4(5H)-one;

or an N-oxide, tautomer, or hydrate thereof, or a pharmaceutically acceptable salt thereof.

22. The compound selected from the group consisting of
3-bromo-5-methyl-7-(pyridin-4-yl)thieno[2,3-d]pyridazin-4(5H)-one;
7-chloro-5-methyl-3-(pyridin-4-yl)thieno[2,3-d]pyridazin-4(5H)-one;
3-bromo-7-(pyridin-4-yl)-5-(2,2,2-trifluoroethyl)-thieno[2,3-d]pyridazin-4(5H)-one; and
7-hydroxy-5-methyl-3-(pyridin-4-yl)thieno[2,3-d]pyridazin-4(5H)-one;

or an N-oxide, tautomer, or hydrate thereof, or a pharmaceutically acceptable salt thereof.

23. A pharmaceutical composition which comprises at least one compound as claimed in claim 1, and at least one excipient.

* * * * *